(12) United States Patent
Khvorova et al.

(10) Patent No.: US 8,415,466 B2
(45) Date of Patent: Apr. 9, 2013

(54) DUPLEX OLIGONUCLEOTIDES WITH ENHANCED FUNCTIONALITY IN GENE REGULATION

(75) Inventors: Anastasia Khvorova, Northborough, MA (US); Devin Leake, Denver, CO (US); Barbara Robertson, Boulder, CO (US); Annaleen Vermeulen, Lafayette, CO (US); Christina Yamada, Boulder, CO (US)

(73) Assignee: Dharmacon, Inc., Lafayette, CO (US)

( * ) Notice: Subject to any disclaimer, the term of this patent is extended or adjusted under 35 U.S.C. 154(b) by 0 days.

(21) Appl. No.: 13/460,026

(22) Filed: Apr. 30, 2012

(65) Prior Publication Data

US 2012/0259001 A1 Oct. 11, 2012

Related U.S. Application Data

(62) Division of application No. 12/368,856, filed on Feb. 10, 2009, now Pat. No. 8,188, 060.

(60) Provisional application No. 61/027,609, filed on Feb. 11, 2008.

(51) Int. Cl.
*C07H 21/04* (2006.01)
(52) U.S. Cl. .................. 536/24.5; 536/24.1; 536/24.31; 514/44
(58) Field of Classification Search ................ None
See application file for complete search history.

(56) References Cited

U.S. PATENT DOCUMENTS

2007/0117767 A1* 5/2007 Hohjoh ........................ 514/44
2010/0227909 A1* 9/2010 Cleary et al. ................ 514/44 A

* cited by examiner

*Primary Examiner* — Kimberly Chong
(74) *Attorney, Agent, or Firm* — Dorf & Nelson LLP; Scott D. Locke, Esq.

(57) ABSTRACT

Disclosed are methods of enhancing functionality of duplex oligonucleotides and compositions made by the methods. The duplex oligonucleotides include siRNAs, miRNA mimics, and piRNA mimics which contain modified nucleotides and mismatches between the two strands of the molecule at specific nucleotide positions.

10 Claims, 10 Drawing Sheets

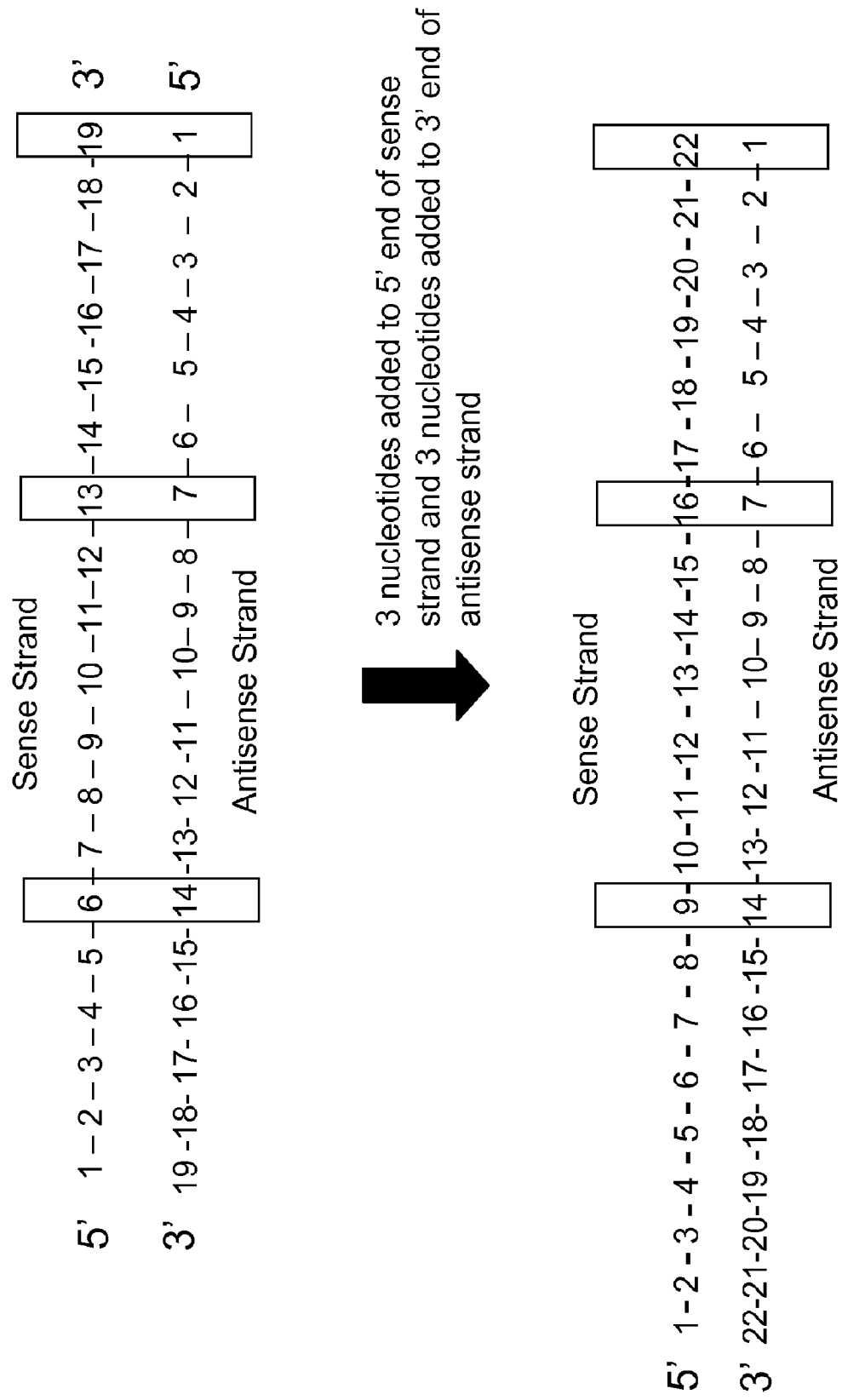

Example of paired mismatch (antisense nucleotide positions 5 and 6)

SEQUENCE LISTING

<160> NUMBER OF SEQ ID NOS: 87

<210> SEQ ID NO 1
<211> LENGTH: 21
<212> TYPE: RNA
<213> ORGANISM: Artificial sequence
<220> FEATURE:
<223> OTHER INFORMATION: Antisense strand sequence
<220> FEATURE:
<221> NAME/KEY: modified_base
<222> LOCATION: (1)..(21)
<223> OTHER INFORMATION: 2'-F on all C and U residues
<220> FEATURE:
<221> NAME/KEY: misc_feature
<222> LOCATION: (1)..(1)
<223> OTHER INFORMATION: Phosphorylation on 5' end of nucleotide
<220> FEATURE:
<221> NAME/KEY: modified_base
<222> LOCATION: (20)..(21)
<223> OTHER INFORMATION: phosphorothioate modified internucleotide
    linkages

<400> SEQUENCE: 1
uggaguguga caauguguu u                                                   21

<210> SEQ ID NO 2
<211> LENGTH: 19
<212> TYPE: RNA
<213> ORGANISM: Artificial sequence
<220> FEATURE:
<223> OTHER INFORMATION: Sense strand sequence
<220> FEATURE:
<221> NAME/KEY: modified_base
<222> LOCATION: (1)..(2)
<223> OTHER INFORMATION: 2'-O-methyl
<220> FEATURE:
<221> NAME/KEY: modified_base
<222> LOCATION: (1)..(19)
<223> OTHER INFORMATION: 2'-O-methyl on all C and U residues
<220> FEATURE:
<221> NAME/KEY: misc_feature
<222> LOCATION: (19)..(19)
<223> OTHER INFORMATION: cholesterol conjugate linked to 3' end of sense
    nucleotide: cholesteryl 5-(bis(4-methoxyphenyl)(phenyl)methoxy)-3
    hydroxypentylcarbamate)

<400> SEQUENCE: 2
acaccauugu cacacucca                                                     19

<210> SEQ ID NO 3
<211> LENGTH: 21
<212> TYPE: RNA
<213> ORGANISM: Artificial sequence
<220> FEATURE:
<223> OTHER INFORMATION: Antisense strand sequence
<220> FEATURE:
<221> NAME/KEY: misc_feature
<222> LOCATION: (1)..(1)
<223> OTHER INFORMATION: phosphorylation on 5' end of nucleotide
<220> FEATURE:
<221> NAME/KEY: modified_base
<222> LOCATION: (1)..(21)
<223> OTHER INFORMATION: 2'-F on all C and U residues
<220> FEATURE:
<221> NAME/KEY: modified_base
<222> LOCATION: (20)..(21)
<223> OTHER INFORMATION: phosphorothioate modified internucleotide
    linkages

<400> SEQUENCE: 3
uaacacuguc ugguaaagau u                                                  21

-continued

```
<210> SEQ ID NO 4
<211> LENGTH: 19
<212> TYPE: RNA
<213> ORGANISM: Artificial sequence
<220> FEATURE:
<223> OTHER INFORMATION: Sense strand sequence
<220> FEATURE:
<221> NAME/KEY: modified_base
<222> LOCATION: (1)..(2)
<223> OTHER INFORMATION: 2'-O-methyl
<220> FEATURE:
<221> NAME/KEY: modified_base
<222> LOCATION: (1)..(19)
<223> OTHER INFORMATION: 2'-O-methyl on all C and U residues
<220> FEATURE:
<221> NAME/KEY: misc_feature
<222> LOCATION: (19)..(19)
<223> OTHER INFORMATION: cholesterol conjugate linked to 3' end of sense
      nucleotide: cholesteryl 5-(bis(4-methoxyphenyl)(phenyl)methoxy)-3
      hydroxypentylcarbamate)

<400> SEQUENCE: 4
ucuuuaccag acaguguua                                                    19

<210> SEQ ID NO 5
<211> LENGTH: 54
<212> TYPE: RNA
<213> ORGANISM: Artificial sequence
<220> FEATURE:
<223> OTHER INFORMATION: miRNA
<220> FEATURE:
<221> NAME/KEY: modified_base
<222> LOCATION: (1)..(54)
<223> OTHER INFORMATION: 2'-O-methyl

<400> SEQUENCE: 5
agcucugaaa agagcuucaa caucagucug auaagcauuc gagauucguc ucga            54

<210> SEQ ID NO 6
<211> LENGTH: 54
<212> TYPE: RNA
<213> ORGANISM: Artificial sequence
<220> FEATURE:
<223> OTHER INFORMATION: miRNA
<220> FEATURE:
<221> NAME/KEY: modified_base
<222> LOCATION: (1)..(54)
<223> OTHER INFORMATION: 2'-O-methyl

<400> SEQUENCE: 6
agcucugaaa agagcuucaa caucagucug auaacguauc gagauucguc ucga            54

<210> SEQ ID NO 7
<211> LENGTH: 54
<212> TYPE: RNA
<213> ORGANISM: Artificial sequence
<220> FEATURE:
<223> OTHER INFORMATION: miRNA
<220> FEATURE:
<221> NAME/KEY: modified_base
<222> LOCATION: (1)..(54)
<223> OTHER INFORMATION: 2'-O-methyl

<400> SEQUENCE: 7
agcucugaaa agagcuucaa caucagucug auuugcuauc gagauucguc ucga            54

<210> SEQ ID NO 8
<211> LENGTH: 54
<212> TYPE: RNA
<213> ORGANISM: Artificial sequence
<220> FEATURE:
```

```
<223> OTHER INFORMATION: miRNA
<220> FEATURE:
<221> NAME/KEY: modified_base
<222> LOCATION: (1)..(54)
<223> OTHER INFORMATION: 2'-O-methyl

<400> SEQUENCE: 8
agcucugaaa agagcuucaa caucagucug uaaagcuauc gagauucguc ucga      54

<210> SEQ ID NO 9
<211> LENGTH: 54
<212> TYPE: RNA
<213> ORGANISM: Artificial sequence
<220> FEATURE:
<223> OTHER INFORMATION: miRNA
<220> FEATURE:
<221> NAME/KEY: modified_base
<222> LOCATION: (1)..(54)
<223> OTHER INFORMATION: 2'-O-methyl

<400> SEQUENCE: 9
agcucugaaa agagcuucaa caucagucac auaagcuauc gagauucguc ucga      54

<210> SEQ ID NO 10
<211> LENGTH: 54
<212> TYPE: RNA
<213> ORGANISM: Artificial sequence
<220> FEATURE:
<223> OTHER INFORMATION: miRNA
<220> FEATURE:
<221> NAME/KEY: modified_base
<222> LOCATION: (1)..(54)
<223> OTHER INFORMATION: 2'-O-methyl

<400> SEQUENCE: 10
agcucugaaa agagcuucaa caucagagug auaagcuauc gagauucguc ucga      54

<210> SEQ ID NO 11
<211> LENGTH: 54
<212> TYPE: RNA
<213> ORGANISM: Artificial sequence
<220> FEATURE:
<223> OTHER INFORMATION: miRNA
<220> FEATURE:
<221> NAME/KEY: modified_base
<222> LOCATION: (1)..(54)
<223> OTHER INFORMATION: 2'-O-methyl

<400> SEQUENCE: 11
agcucugaaa agagcuucaa caucucucug auaagcuauc gagauucguc ucga      54

<210> SEQ ID NO 12
<211> LENGTH: 54
<212> TYPE: RNA
<213> ORGANISM: Artificial sequence
<220> FEATURE:
<223> OTHER INFORMATION: miRNA
<220> FEATURE:
<221> NAME/KEY: modified_base
<222> LOCATION: (1)..(54)
<223> OTHER INFORMATION: 2'-O-methyl

<400> SEQUENCE: 12
agcucugaaa agagcuucaa caagagucug auaagcuauc gagauucguc ucga      54

<210> SEQ ID NO 13
<211> LENGTH: 54
<212> TYPE: RNA
<213> ORGANISM: Artificial sequence
<220> FEATURE:
```

```
<223> OTHER INFORMATION: miRNA
<220> FEATURE:
<221> NAME/KEY: modified_base
<222> LOCATION: (1)..(54)
<223> OTHER INFORMATION: 2'-O-methyl

<400> SEQUENCE: 13
agcucugaaa agagcuucaa guucagucug auaagcuauc gagauucguc ucga        54

<210> SEQ ID NO 14
<211> LENGTH: 54
<212> TYPE: RNA
<213> ORGANISM: Artificial sequence
<220> FEATURE:
<223> OTHER INFORMATION: miRNA
<220> FEATURE:
<221> NAME/KEY: modified_base
<222> LOCATION: (1)..(54)
<223> OTHER INFORMATION: 2'-O-methyl

<400> SEQUENCE: 14
agcucugaaa agagcuucuu caucagucug auaagcuauc gagauucguc ucga        54

<210> SEQ ID NO 15
<211> LENGTH: 54
<212> TYPE: RNA
<213> ORGANISM: Artificial sequence
<220> FEATURE:
<223> OTHER INFORMATION: miRNA
<220> FEATURE:
<221> NAME/KEY: modified_base
<222> LOCATION: (1)..(54)
<223> OTHER INFORMATION: 2'-O-methyl

<400> SEQUENCE: 15
agcucugaaa agagcuagaa caucagucug auaagcuauc gagauucguc ucga        54

<210> SEQ ID NO 16
<211> LENGTH: 21
<212> TYPE: RNA
<213> ORGANISM: Artificial sequence
<220> FEATURE:
<223> OTHER INFORMATION: Antisense strand sequence
<220> FEATURE:
<221> NAME/KEY: misc_feature
<222> LOCATION: (1)..(1)
<223> OTHER INFORMATION: phosphorylation on 5' end of nucleotide
<220> FEATURE:
<221> NAME/KEY: modified_base
<222> LOCATION: (1)..(21)
<223> OTHER INFORMATION: 2'-F on all C and U residues
<220> FEATURE:
<221> NAME/KEY: modified_base
<222> LOCATION: (20)..(21)
<223> OTHER INFORMATION: phosphorothioate modified internucleotide
      linkages

<400> SEQUENCE: 16
uggaauguaa agaaguaugu u                                            21

<210> SEQ ID NO 17
<211> LENGTH: 19
<212> TYPE: RNA
<213> ORGANISM: Artificial sequence
<220> FEATURE:
<223> OTHER INFORMATION: Sense strand sequence
<220> FEATURE:
<221> NAME/KEY: modified_base
<222> LOCATION: (1)..(2)
<223> OTHER INFORMATION: 2'-O-methyl
<220> FEATURE:
<221> NAME/KEY: modified_base
```

<222> LOCATION: (1)..(19)
<223> OTHER INFORMATION: 2'-O-methyl on all C and U residues
<220> FEATURE:
<221> NAME/KEY: misc_feature
<222> LOCATION: (19)..(19)
<223> OTHER INFORMATION: cholesterol conjugate linked to 3' end of sense
      nucleotide: cholesteryl 5-(bis(4-methoxyphenyl)(phenyl)methoxy)-3
      hydroxypentylcarbamate)

<400> SEQUENCE: 17
cauacuucuu uacauucca                                              19

<210> SEQ ID NO 18
<211> LENGTH: 19
<212> TYPE: RNA
<213> ORGANISM: Artificial sequence
<220> FEATURE:
<223> OTHER INFORMATION: Sense strand sequence
<220> FEATURE:
<221> NAME/KEY: modified_base
<222> LOCATION: (1)..(2)
<223> OTHER INFORMATION: 2'-O-methyl
<220> FEATURE:
<221> NAME/KEY: modified_base
<222> LOCATION: (1)..(19)
<223> OTHER INFORMATION: 2'-O-methyl on all C and U residues
<220> FEATURE:
<221> NAME/KEY: misc_feature
<222> LOCATION: (19)..(19)
<223> OTHER INFORMATION: cholesterol conjugate linked to 3' end of sense
      nucleotide: cholesteryl 5-(bis(4-methoxyphenyl)(phenyl)methoxy)-3
      hydroxypentylcarbamate)

<400> SEQUENCE: 18
cauacaucuu uacauucca                                              19

<210> SEQ ID NO 19
<211> LENGTH: 19
<212> TYPE: RNA
<213> ORGANISM: Artificial sequence
<220> FEATURE:
<223> OTHER INFORMATION: Sense strand sequence
<220> FEATURE:
<221> NAME/KEY: modified_base
<222> LOCATION: (1)..(2)
<223> OTHER INFORMATION: 2'-O-methyl
<220> FEATURE:
<221> NAME/KEY: modified_base
<222> LOCATION: (1)..(19)
<223> OTHER INFORMATION: 2'-O-methyl on all C and U residues
<220> FEATURE:
<221> NAME/KEY: misc_feature
<222> LOCATION: (19)..(19)
<223> OTHER INFORMATION: cholesterol conjugate linked to 3' end of sense
      nucleotide: cholesteryl 5-(bis(4-methoxyphenyl)(phenyl)methoxy)-3
      hydroxypentylcarbamate)

<400> SEQUENCE: 19
cauacaucuu uacauuccu                                              19

<210> SEQ ID NO 20
<211> LENGTH: 19
<212> TYPE: RNA
<213> ORGANISM: Artificial sequence
<220> FEATURE:
<223> OTHER INFORMATION: Sense strand sequence
<220> FEATURE:
<221> NAME/KEY: modified_base
<222> LOCATION: (1)..(2)
<223> OTHER INFORMATION: 2'-O-methyl
<220> FEATURE:
<221> NAME/KEY: modified_base
<222> LOCATION: (1)..(19)
<223> OTHER INFORMATION: 2'-O-methyl on all C and U residues

```
<220> FEATURE:
<221> NAME/KEY: misc_feature
<222> LOCATION: (19)..(19)
<223> OTHER INFORMATION: cholesterol conjugate linked to 3' end of sense
      nucleotide: cholesteryl 5-(bis(4-methoxyphenyl)(phenyl)methoxy)-3
      hydroxypentylcarbamate)

<400> SEQUENCE: 20
cauacaucuu uagauuccu                                                  19

<210> SEQ ID NO 21
<211> LENGTH: 21
<212> TYPE: RNA
<213> ORGANISM: Artificial sequence
<220> FEATURE:
<223> OTHER INFORMATION: Antisense strand sequence
<220> FEATURE:
<221> NAME/KEY: misc_feature
<222> LOCATION: (1)..(1)
<223> OTHER INFORMATION: phosphorylation on 5' end of nucleotide
<220> FEATURE:
<221> NAME/KEY: modified_base
<222> LOCATION: (1)..(21)
<223> OTHER INFORMATION: 2'-F on all C and U residues
<220> FEATURE:
<221> NAME/KEY: modified_base
<222> LOCATION: (20)..(21)
<223> OTHER INFORMATION: phosphorothioate modified internucleotide
      linkages

<400> SEQUENCE: 21
uaaggugcau cuagugcagu u                                               21

<210> SEQ ID NO 22
<211> LENGTH: 19
<212> TYPE: RNA
<213> ORGANISM: Artificial sequence
<220> FEATURE:
<223> OTHER INFORMATION: Sense strand sequence
<220> FEATURE:
<221> NAME/KEY: modified_base
<222> LOCATION: (1)..(2)
<223> OTHER INFORMATION: 2'-O-methyl
<220> FEATURE:
<221> NAME/KEY: modified_base
<222> LOCATION: (1)..(19)
<223> OTHER INFORMATION: 2'-O-methyl on all C and U residues
<220> FEATURE:
<221> NAME/KEY: misc_feature
<222> LOCATION: (19)..(19)
<223> OTHER INFORMATION: cholesterol conjugate linked to 3' end of sense
      nucleotide: cholesteryl 5-(bis(4-methoxyphenyl)(phenyl)methoxy)-3
      hydroxypentylcarbamate)

<400> SEQUENCE: 22
cugcacuaga ugcaccuua                                                  19

<210> SEQ ID NO 23
<211> LENGTH: 19
<212> TYPE: RNA
<213> ORGANISM: Artificial sequence
<220> FEATURE:
<223> OTHER INFORMATION: Sense strand sequence
<220> FEATURE:
<221> NAME/KEY: modified_base
<222> LOCATION: (1)..(2)
<223> OTHER INFORMATION: 2'-O-methyl
<220> FEATURE:
<221> NAME/KEY: modified_base
<222> LOCATION: (1)..(19)
<223> OTHER INFORMATION: 2'-O-methyl on all C and U residues
<220> FEATURE:
<221> NAME/KEY: misc_feature
<222> LOCATION: (19)..(19)
```

```
<223> OTHER INFORMATION: cholesterol conjugate linked to 3' end of sense
      nucleotide: cholesteryl 5-(bis(4-methoxyphenyl)(phenyl)methoxy)-3
      hydroxypentylcarbamate)

<400> SEQUENCE: 23
cugcaguaga ugcaccuua                                                19

<210> SEQ ID NO 24
<211> LENGTH: 19
<212> TYPE: RNA
<213> ORGANISM: Artificial sequence
<220> FEATURE:
<223> OTHER INFORMATION: Sense strand sequence
<220> FEATURE:
<221> NAME/KEY: modified_base
<222> LOCATION: (1)..(2)
<223> OTHER INFORMATION: 2'-O-methyl
<220> FEATURE:
<221> NAME/KEY: modified_base
<222> LOCATION: (1)..(19)
<223> OTHER INFORMATION: 2'-O-methyl on all C and U residues
<220> FEATURE:
<221> NAME/KEY: misc_feature
<222> LOCATION: (19)..(19)
<223> OTHER INFORMATION: cholesterol conjugate linked to 3' end of sense
      nucleotide: cholesteryl 5-(bis(4-methoxyphenyl)(phenyl)methoxy)-3
      hydroxypentylcarbamate)

<400> SEQUENCE: 24
cugcaguaga ugcaccuuu                                                19

<210> SEQ ID NO 25
<211> LENGTH: 19
<212> TYPE: RNA
<213> ORGANISM: Artificial sequence
<220> FEATURE:
<223> OTHER INFORMATION: Sense strand sequence
<220> FEATURE:
<221> NAME/KEY: modified_base
<222> LOCATION: (1)..(2)
<223> OTHER INFORMATION: 2'-O-methyl
<220> FEATURE:
<221> NAME/KEY: modified_base
<222> LOCATION: (1)..(19)
<223> OTHER INFORMATION: 2'-O-methyl on all C and U residues
<220> FEATURE:
<221> NAME/KEY: misc_feature
<222> LOCATION: (19)..(19)
<223> OTHER INFORMATION: cholesterol conjugate linked to 3' end of sense
      nucleotide: cholesteryl 5-(bis(4-methoxyphenyl)(phenyl)methoxy)-3
      hydroxypentylcarbamate)

<400> SEQUENCE: 25
cugcaguaga uggaccuuu                                                19

<210> SEQ ID NO 26
<211> LENGTH: 21
<212> TYPE: RNA
<213> ORGANISM: Artificial sequence
<220> FEATURE:
<223> OTHER INFORMATION: Antisense strand sequence
<220> FEATURE:
<221> NAME/KEY: misc_feature
<222> LOCATION: (1)..(1)
<223> OTHER INFORMATION: phosphorylation on 5' end of nucleotide
<220> FEATURE:
<221> NAME/KEY: modified_base
<222> LOCATION: (1)..(21)
<223> OTHER INFORMATION: 2'-F on all C and U residues
<220> FEATURE:
<221> NAME/KEY: modified_base
<222> LOCATION: (20)..(21)
<223> OTHER INFORMATION: phosphorothioate modified internucleotide
      linkages
```

```
<400> SEQUENCE: 26
uauugcacuu gucccggccu u                                              21

<210> SEQ ID NO 27
<211> LENGTH: 19
<212> TYPE: RNA
<213> ORGANISM: Artificial sequence
<220> FEATURE:
<223> OTHER INFORMATION: Sense strand sequence
<220> FEATURE:
<221> NAME/KEY: modified_base
<222> LOCATION: (1)..(2)
<223> OTHER INFORMATION: 2'-O-methyl
<220> FEATURE:
<221> NAME/KEY: modified_base
<222> LOCATION: (1)..(19)
<223> OTHER INFORMATION: 2'-O-methyl on all C and U residues
<220> FEATURE:
<221> NAME/KEY: misc_feature
<222> LOCATION: (19)..(19)
<223> OTHER INFORMATION: cholesterol conjugate linked to 3' end of sense
      nucleotide: cholesteryl 5-(bis(4-methoxyphenyl)(phenyl)methoxy)-3
      hydroxypentylcarbamate)

<400> SEQUENCE: 27
ggccgggaca agugcaaua                                                 19

<210> SEQ ID NO 28
<211> LENGTH: 19
<212> TYPE: RNA
<213> ORGANISM: Artificial sequence
<220> FEATURE:
<223> OTHER INFORMATION: Sense strand sequence
<220> FEATURE:
<221> NAME/KEY: modified_base
<222> LOCATION: (1)..(2)
<223> OTHER INFORMATION: 2'-O-methyl
<220> FEATURE:
<221> NAME/KEY: modified_base
<222> LOCATION: (1)..(19)
<223> OTHER INFORMATION: 2'-O-methyl on all C and U residues
<220> FEATURE:
<221> NAME/KEY: misc_feature
<222> LOCATION: (19)..(19)
<223> OTHER INFORMATION: cholesterol conjugate linked to 3' end of sense
      nucleotide: cholesteryl 5-(bis(4-methoxyphenyl)(phenyl)methoxy)-3
      hydroxypentylcarbamate)

<400> SEQUENCE: 28
ggccgcgaca agugcaaua                                                 19

<210> SEQ ID NO 29
<211> LENGTH: 19
<212> TYPE: RNA
<213> ORGANISM: Artificial sequence
<220> FEATURE:
<223> OTHER INFORMATION: Sense strand sequence
<220> FEATURE:
<221> NAME/KEY: modified_base
<222> LOCATION: (1)..(2)
<223> OTHER INFORMATION: 2'-O-methyl
<220> FEATURE:
<221> NAME/KEY: modified_base
<222> LOCATION: (1)..(19)
<223> OTHER INFORMATION: 2'-O-methyl on all C and U residues
<220> FEATURE:
<221> NAME/KEY: misc_feature
<222> LOCATION: (19)..(19)
<223> OTHER INFORMATION: cholesterol conjugate linked to 3' end of sense
      nucleotide: cholesteryl 5-(bis(4-methoxyphenyl)(phenyl)methoxy)-3
      hydroxypentylcarbamate)

<400> SEQUENCE: 29
```

```
ggccgcgaca agugcaauu                                                    19

<210> SEQ ID NO 30
<211> LENGTH: 19
<212> TYPE: RNA
<213> ORGANISM: Artificial sequence
<220> FEATURE:
<223> OTHER INFORMATION: Sense strand sequence
<220> FEATURE:
<221> NAME/KEY: modified_base
<222> LOCATION: (1)..(2)
<223> OTHER INFORMATION: 2'-O-methyl
<220> FEATURE:
<221> NAME/KEY: modified_base
<222> LOCATION: (1)..(19)
<223> OTHER INFORMATION: 2'-O-methyl on all C and U residues
<220> FEATURE:
<221> NAME/KEY: misc_feature
<222> LOCATION: (19)..(19)
<223> OTHER INFORMATION: cholesterol conjugate linked to 3' end of sense
      nucleotide: cholesteryl 5-(bis(4-methoxyphenyl)(phenyl)methoxy)-3
      hydroxypentylcarbamate)

<400> SEQUENCE: 30
ggccgcgaca agagcaauu                                                    19

<210> SEQ ID NO 31
<211> LENGTH: 21
<212> TYPE: RNA
<213> ORGANISM: Artificial sequence
<220> FEATURE:
<223> OTHER INFORMATION: Antisense strand sequence
<220> FEATURE:
<221> NAME/KEY: misc_feature
<222> LOCATION: (1)..(1)
<223> OTHER INFORMATION: phosphorylation on 5' end of nucleotide
<220> FEATURE:
<221> NAME/KEY: modified_base
<222> LOCATION: (1)..(21)
<223> OTHER INFORMATION: 2'-F on all C and U residues
<220> FEATURE:
<221> NAME/KEY: modified_base
<222> LOCATION: (20)..(21)
<223> OTHER INFORMATION: phosphorothioate modified internucleotide
      linkages

<400> SEQUENCE: 31
ugagguagua aguuguauuu u                                                 21

<210> SEQ ID NO 32
<211> LENGTH: 19
<212> TYPE: RNA
<213> ORGANISM: Artificial sequence
<220> FEATURE:
<223> OTHER INFORMATION: Sense strand sequence
<220> FEATURE:
<221> NAME/KEY: modified_base
<222> LOCATION: (1)..(2)
<223> OTHER INFORMATION: 2'-O-methyl
<220> FEATURE:
<221> NAME/KEY: modified_base
<222> LOCATION: (1)..(19)
<223> OTHER INFORMATION: 2'-O-methyl on all C and U residues
<220> FEATURE:
<221> NAME/KEY: misc_feature
<222> LOCATION: (19)..(19)
<223> OTHER INFORMATION: cholesterol conjugate linked to 3' end of sense
      nucleotide: cholesteryl 5-(bis(4-methoxyphenyl)(phenyl)methoxy)-3
      hydroxypentylcarbamate)

<400> SEQUENCE: 32
aauacaacuu acuaccuca                                                    19
```

```
<210> SEQ ID NO 33
<211> LENGTH: 19
<212> TYPE: RNA
<213> ORGANISM: Artificial sequence
<220> FEATURE:
<223> OTHER INFORMATION: Sense strand sequence
<220> FEATURE:
<221> NAME/KEY: modified_base
<222> LOCATION: (1)..(2)
<223> OTHER INFORMATION: 2'-O-methyl
<220> FEATURE:
<221> NAME/KEY: modified_base
<222> LOCATION: (1)..(19)
<223> OTHER INFORMATION: 2'-O-methyl on all C and U residues
<220> FEATURE:
<221> NAME/KEY: misc_feature
<222> LOCATION: (19)..(19)
<223> OTHER INFORMATION: cholesterol conjugate linked to 3' end of sense
      nucleotide: cholesteryl 5-(bis(4-methoxyphenyl)(phenyl)methoxy)-3
      hydroxypentylcarbamate)

<400> SEQUENCE: 33
aauacuacuu acuaccuca                                                    19

<210> SEQ ID NO 34
<211> LENGTH: 19
<212> TYPE: RNA
<213> ORGANISM: Artificial sequence
<220> FEATURE:
<223> OTHER INFORMATION: Sense strand sequence
<220> FEATURE:
<221> NAME/KEY: modified_base
<222> LOCATION: (1)..(2)
<223> OTHER INFORMATION: 2'-O-methyl
<220> FEATURE:
<221> NAME/KEY: modified_base
<222> LOCATION: (1)..(19)
<223> OTHER INFORMATION: 2'-O-methyl on all C and U residues
<220> FEATURE:
<221> NAME/KEY: misc_feature
<222> LOCATION: (19)..(19)
<223> OTHER INFORMATION: cholesterol conjugate linked to 3' end of sense
      nucleotide: cholesteryl 5-(bis(4-methoxyphenyl)(phenyl)methoxy)-3
      hydroxypentylcarbamate)

<400> SEQUENCE: 34
aauacuacuu acuaccucu                                                    19

<210> SEQ ID NO 35
<211> LENGTH: 19
<212> TYPE: RNA
<213> ORGANISM: Artificial sequence
<220> FEATURE:
<223> OTHER INFORMATION: Sense strand sequence
<220> FEATURE:
<221> NAME/KEY: modified_base
<222> LOCATION: (1)..(2)
<223> OTHER INFORMATION: 2'-O-methyl
<220> FEATURE:
<221> NAME/KEY: modified_base
<222> LOCATION: (1)..(19)
<223> OTHER INFORMATION: 2'-O-methyl on all C and U residues
<220> FEATURE:
<221> NAME/KEY: misc_feature
<222> LOCATION: (19)..(19)
<223> OTHER INFORMATION: cholesterol conjugate linked to 3' end of sense
      nucleotide: cholesteryl 5-(bis(4-methoxyphenyl)(phenyl)methoxy)-3
      hydroxypentylcarbamate)

<400> SEQUENCE: 35
aauacuacuu acaaccucu                                                    19

<210> SEQ ID NO 36
```

-continued

```
<211> LENGTH: 21
<212> TYPE: RNA
<213> ORGANISM: Artificial sequence
<220> FEATURE:
<223> OTHER INFORMATION: Antisense strand sequence
<220> FEATURE:
<221> NAME/KEY: misc_feature
<222> LOCATION: (1)..(1)
<223> OTHER INFORMATION: phosphorylation on 5' end of nucleotide
<220> FEATURE:
<221> NAME/KEY: modified_base
<222> LOCATION: (1)..(21)
<223> OTHER INFORMATION: 2'-F on all C and U residues
<220> FEATURE:
<221> NAME/KEY: modified_base
<222> LOCATION: (20)..(21)
<223> OTHER INFORMATION: phosphorothioate modified internucleotide
      linkages

<400> SEQUENCE: 36
agcagcauug uacagggcuu u                                              21

<210> SEQ ID NO 37
<211> LENGTH: 19
<212> TYPE: RNA
<213> ORGANISM: Artificial sequence
<220> FEATURE:
<223> OTHER INFORMATION: Sense strand sequence
<220> FEATURE:
<221> NAME/KEY: modified_base
<222> LOCATION: (1)..(2)
<223> OTHER INFORMATION: 2'-O-methyl
<220> FEATURE:
<221> NAME/KEY: modified_base
<222> LOCATION: (1)..(19)
<223> OTHER INFORMATION: 2'-O-methyl on all C and U residues
<220> FEATURE:
<221> NAME/KEY: misc_feature
<222> LOCATION: (19)..(19)
<223> OTHER INFORMATION: cholesterol conjugate linked to 3' end of sense
      nucleotide: cholesteryl 5-(bis(4-methoxyphenyl)(phenyl)methoxy)-3
      hydroxypentylcarbamate)

<400> SEQUENCE: 37
agcccuguac aaugcugcu                                                 19

<210> SEQ ID NO 38
<211> LENGTH: 19
<212> TYPE: RNA
<213> ORGANISM: Artificial sequence
<220> FEATURE:
<223> OTHER INFORMATION: Sense strand sequence
<220> FEATURE:
<221> NAME/KEY: modified_base
<222> LOCATION: (1)..(2)
<223> OTHER INFORMATION: 2'-O-methyl
<220> FEATURE:
<221> NAME/KEY: modified_base
<222> LOCATION: (1)..(19)
<223> OTHER INFORMATION: 2'-O-methyl on all C and U residues
<220> FEATURE:
<221> NAME/KEY: misc_feature
<222> LOCATION: (19)..(19)
<223> OTHER INFORMATION: cholesterol conjugate linked to 3' end of sense
      nucleotide: cholesteryl 5-(bis(4-methoxyphenyl)(phenyl)methoxy)-3
      hydroxypentylcarbamate)

<400> SEQUENCE: 38
agcccaguac aaugcugcu                                                 19

<210> SEQ ID NO 39
<211> LENGTH: 19
<212> TYPE: RNA
<213> ORGANISM: Artificial sequence
```

```
<220> FEATURE:
<223> OTHER INFORMATION: Sense strand sequence
<220> FEATURE:
<221> NAME/KEY: modified_base
<222> LOCATION: (1)..(2)
<223> OTHER INFORMATION: 2'-O-methyl
<220> FEATURE:
<221> NAME/KEY: modified_base
<222> LOCATION: (1)..(19)
<223> OTHER INFORMATION: 2'-O-methyl on all C and U residues
<220> FEATURE:
<221> NAME/KEY: misc_feature
<222> LOCATION: (19)..(19)
<223> OTHER INFORMATION: cholesterol conjugate linked to 3' end of sense
      nucleotide: cholesteryl 5-(bis(4-methoxyphenyl)(phenyl)methoxy)-3
      hydroxypentylcarbamate)

<400> SEQUENCE: 39
agcccaguac aaugcugca                                                   19

<210> SEQ ID NO 40
<211> LENGTH: 19
<212> TYPE: RNA
<213> ORGANISM: Artificial sequence
<220> FEATURE:
<223> OTHER INFORMATION: Sense strand sequence
<220> FEATURE:
<221> NAME/KEY: modified_base
<222> LOCATION: (1)..(2)
<223> OTHER INFORMATION: 2'-O-methyl
<220> FEATURE:
<221> NAME/KEY: modified_base
<222> LOCATION: (1)..(19)
<223> OTHER INFORMATION: 2'-O-methyl on all C and U residues
<220> FEATURE:
<221> NAME/KEY: misc_feature
<222> LOCATION: (19)..(19)
<223> OTHER INFORMATION: cholesterol conjugate linked to 3' end of sense
      nucleotide: cholesteryl 5-(bis(4-methoxyphenyl)(phenyl)methoxy)-3
      hydroxypentylcarbamate)

<400> SEQUENCE: 40
agcccaguac aaagcugca                                                   19

<210> SEQ ID NO 41
<211> LENGTH: 21
<212> TYPE: RNA
<213> ORGANISM: Artificial sequence
<220> FEATURE:
<223> OTHER INFORMATION: Antisense strand sequence
<220> FEATURE:
<221> NAME/KEY: misc_feature
<222> LOCATION: (1)..(1)
<223> OTHER INFORMATION: phosphorylation on 5' end of nucleotide
<220> FEATURE:
<221> NAME/KEY: modified_base
<222> LOCATION: (1)..(21)
<223> OTHER INFORMATION: 2'-F on all C and U residues
<220> FEATURE:
<221> NAME/KEY: modified_base
<222> LOCATION: (21)..(21)
<223> OTHER INFORMATION: phosphorothioate modified internucleotide
      linkages

<400> SEQUENCE: 41
cagugcaaug uuaaaagggu u                                                21

<210> SEQ ID NO 42
<211> LENGTH: 19
<212> TYPE: RNA
<213> ORGANISM: Artificial sequence
<220> FEATURE:
<223> OTHER INFORMATION: Sense strand sequence
<220> FEATURE:
```

```
<221> NAME/KEY: modified_base
<222> LOCATION: (1)..(2)
<223> OTHER INFORMATION: 2'-O-methyl
<220> FEATURE:
<221> NAME/KEY: modified_base
<222> LOCATION: (1)..(19)
<223> OTHER INFORMATION: 2'-O-methyl on all C and U residues
<220> FEATURE:
<221> NAME/KEY: misc_feature
<222> LOCATION: (19)..(19)
<223> OTHER INFORMATION: cholesterol conjugate linked to 3' end of sense
      nucleotide: cholesteryl 5-(bis(4-methoxyphenyl)(phenyl)methoxy)-3
      hydroxypentylcarbamate)

<400> SEQUENCE: 42
cccuuuuaac auugcacug                                             19

<210> SEQ ID NO 43
<211> LENGTH: 19
<212> TYPE: RNA
<213> ORGANISM: Artificial sequence
<220> FEATURE:
<223> OTHER INFORMATION: Sense strand sequence
<220> FEATURE:
<221> NAME/KEY: modified_base
<222> LOCATION: (1)..(2)
<223> OTHER INFORMATION: 2'-O-methyl
<220> FEATURE:
<221> NAME/KEY: modified_base
<222> LOCATION: (1)..(19)
<223> OTHER INFORMATION: 2'-O-methyl on all C and U residues
<220> FEATURE:
<221> NAME/KEY: misc_feature
<222> LOCATION: (19)..(19)
<223> OTHER INFORMATION: cholesterol conjugate linked to 3' end of sense
      nucleotide: cholesteryl 5-(bis(4-methoxyphenyl)(phenyl)methoxy)-3
      hydroxypentylcarbamate)

<400> SEQUENCE: 43
cccuuauaac auugcacug                                             19

<210> SEQ ID NO 44
<211> LENGTH: 19
<212> TYPE: RNA
<213> ORGANISM: Artificial sequence
<220> FEATURE:
<223> OTHER INFORMATION: Sense strand sequence
<220> FEATURE:
<221> NAME/KEY: modified_base
<222> LOCATION: (1)..(2)
<223> OTHER INFORMATION: 2'-O-methyl
<220> FEATURE:
<221> NAME/KEY: modified_base
<222> LOCATION: (1)..(19)
<223> OTHER INFORMATION: 2'-O-methyl on all C and U residues
<220> FEATURE:
<221> NAME/KEY: misc_feature
<222> LOCATION: (19)..(19)
<223> OTHER INFORMATION: cholesterol conjugate linked to 3' end of sense
      nucleotide: cholesteryl 5-(bis(4-methoxyphenyl)(phenyl)methoxy)-3
      hydroxypentylcarbamate)

<400> SEQUENCE: 44
cccuuauaac auugcacuc                                             19

<210> SEQ ID NO 45
<211> LENGTH: 19
<212> TYPE: RNA
<213> ORGANISM: Artificial sequence
<220> FEATURE:
<223> OTHER INFORMATION: Sense strand sequence
<220> FEATURE:
<221> NAME/KEY: modified_base
<222> LOCATION: (1)..(2)
```

```
<223> OTHER INFORMATION: 2'-O-methyl
<220> FEATURE:
<221> NAME/KEY: modified_base
<222> LOCATION: (1)..(19)
<223> OTHER INFORMATION: 2'-O-methyl on all C and U residues
<220> FEATURE:
<221> NAME/KEY: misc_feature
<222> LOCATION: (19)..(19)
<223> OTHER INFORMATION: cholesterol conjugate linked to 3' end of sense
      nucleotide: cholesteryl 5-(bis(4-methoxyphenyl)(phenyl)methoxy)-3
      hydroxypentylcarbamate)

<400> SEQUENCE: 45
cccuuauaac auagcacuc                                               19

<210> SEQ ID NO 46
<211> LENGTH: 21
<212> TYPE: RNA
<213> ORGANISM: Artificial sequence
<220> FEATURE:
<223> OTHER INFORMATION: Antisense strand sequence
<220> FEATURE:
<221> NAME/KEY: misc_feature
<222> LOCATION: (1)..(1)
<223> OTHER INFORMATION: phosphorylation on 5' end of nucleotide
<220> FEATURE:
<221> NAME/KEY: modified_base
<222> LOCATION: (1)..(21)
<223> OTHER INFORMATION: 2'-F on all C and U residues
<220> FEATURE:
<221> NAME/KEY: modified_base
<222> LOCATION: (20)..(21)
<223> OTHER INFORMATION: phosphorothioate modified internucleotide
      linkages

<400> SEQUENCE: 46
uugguccccu ucaaccagcu u                                            21

<210> SEQ ID NO 47
<211> LENGTH: 19
<212> TYPE: RNA
<213> ORGANISM: Artificial sequence
<220> FEATURE:
<223> OTHER INFORMATION: Sense strand sequence
<220> FEATURE:
<221> NAME/KEY: modified_base
<222> LOCATION: (1)..(2)
<223> OTHER INFORMATION: 2'-O-methyl
<220> FEATURE:
<221> NAME/KEY: modified_base
<222> LOCATION: (1)..(19)
<223> OTHER INFORMATION: 2'-O-methyl on all C and U residues
<220> FEATURE:
<221> NAME/KEY: misc_feature
<222> LOCATION: (19)..(19)
<223> OTHER INFORMATION: cholesterol conjugate linked to 3' end of sense
      nucleotide: cholesteryl 5-(bis(4-methoxyphenyl)(phenyl)methoxy)-3
      hydroxypentylcarbamate)

<400> SEQUENCE: 47
gcugguugaa ggggaccaa                                               19

<210> SEQ ID NO 48
<211> LENGTH: 19
<212> TYPE: RNA
<213> ORGANISM: Artificial sequence
<220> FEATURE:
<223> OTHER INFORMATION: Sense strand sequence
<220> FEATURE:
<221> NAME/KEY: modified_base
<222> LOCATION: (1)..(2)
<223> OTHER INFORMATION: 2'-O-methyl
<220> FEATURE:
<221> NAME/KEY: modified_base
```

```
<222> LOCATION: (1)..(19)
<223> OTHER INFORMATION: 2'-O-methyl on all C and U residues
<220> FEATURE:
<221> NAME/KEY: misc_feature
<222> LOCATION: (19)..(19)
<223> OTHER INFORMATION: cholesterol conjugate linked to 3' end of sense
      nucleotide: cholesteryl 5-(bis(4-methoxyphenyl)(phenyl)methoxy)-3
      hydroxypentylcarbamate)

<400> SEQUENCE: 48
gcuggaugaa ggggaccaa                                                    19

<210> SEQ ID NO 49
<211> LENGTH: 19
<212> TYPE: RNA
<213> ORGANISM: Artificial sequence
<220> FEATURE:
<223> OTHER INFORMATION: Sense strand sequence
<220> FEATURE:
<221> NAME/KEY: modified_base
<222> LOCATION: (1)..(2)
<223> OTHER INFORMATION: 2'-O-methyl
<220> FEATURE:
<221> NAME/KEY: modified_base
<222> LOCATION: (1)..(19)
<223> OTHER INFORMATION: 2'-O-methyl on all C and U residues
<220> FEATURE:
<221> NAME/KEY: misc_feature
<222> LOCATION: (19)..(19)
<223> OTHER INFORMATION: cholesterol conjugate linked to 3' end of sense
      nucleotide: cholesteryl 5-(bis(4-methoxyphenyl)(phenyl)methoxy)-3
      hydroxypentylcarbamate)

<400> SEQUENCE: 49
gcuggaugaa ggggaccau                                                    19

<210> SEQ ID NO 50
<211> LENGTH: 19
<212> TYPE: RNA
<213> ORGANISM: Artificial sequence
<220> FEATURE:
<223> OTHER INFORMATION: Sense strand sequence
<220> FEATURE:
<221> NAME/KEY: modified_base
<222> LOCATION: (1)..(2)
<223> OTHER INFORMATION: 2'-O-methyl
<220> FEATURE:
<221> NAME/KEY: modified_base
<222> LOCATION: (1)..(19)
<223> OTHER INFORMATION: 2'-O-methyl on all C and U residues
<220> FEATURE:
<221> NAME/KEY: misc_feature
<222> LOCATION: (19)..(19)
<223> OTHER INFORMATION: cholesterol conjugate linked to 3' end of sense
      nucleotide: cholesteryl 5-(bis(4-methoxyphenyl)(phenyl)methoxy)-3
      hydroxypentylcarbamate)

<400> SEQUENCE: 50
gcuggaugaa ggcgaccau                                                    19

<210> SEQ ID NO 51
<211> LENGTH: 21
<212> TYPE: RNA
<213> ORGANISM: Artificial sequence
<220> FEATURE:
<223> OTHER INFORMATION: Antisense strand sequence
<220> FEATURE:
<221> NAME/KEY: misc_feature
<222> LOCATION: (1)..(1)
<223> OTHER INFORMATION: phosphorylation on 5' end of nucleotide
<220> FEATURE:
<221> NAME/KEY: modified_base
<222> LOCATION: (1)..(21)
<223> OTHER INFORMATION: 2'-F on all C and U residues
```

```
<220> FEATURE:
<221> NAME/KEY: modified_base
<222> LOCATION: (20)..(21)
<223> OTHER INFORMATION: phosphorothioate modified internucleotide
      linkages

<400> SEQUENCE: 51
aacauucaac cugucggugu u                                              21

<210> SEQ ID NO 52
<211> LENGTH: 19
<212> TYPE: RNA
<213> ORGANISM: Artificial sequence
<220> FEATURE:
<223> OTHER INFORMATION: Sense strand sequence
<220> FEATURE:
<221> NAME/KEY: modified_base
<222> LOCATION: (1)..(2)
<223> OTHER INFORMATION: 2'-O-methyl
<220> FEATURE:
<221> NAME/KEY: modified_base
<222> LOCATION: (1)..(19)
<223> OTHER INFORMATION: 2'-O-methyl on all C and U residues
<220> FEATURE:
<221> NAME/KEY: misc_feature
<222> LOCATION: (19)..(19)
<223> OTHER INFORMATION: cholesterol conjugate linked to 3' end of sense
      nucleotide: cholesteryl 5-(bis(4-methoxyphenyl)(phenyl)methoxy)-3
      hydroxypentylcarbamate)

<400> SEQUENCE: 52
caccgacagg uugaauguu                                                 19

<210> SEQ ID NO 53
<211> LENGTH: 19
<212> TYPE: RNA
<213> ORGANISM: Artificial sequence
<220> FEATURE:
<223> OTHER INFORMATION: Sense strand sequence
<220> FEATURE:
<221> NAME/KEY: modified_base
<222> LOCATION: (1)..(2)
<223> OTHER INFORMATION: 2'-O-methyl
<220> FEATURE:
<221> NAME/KEY: modified_base
<222> LOCATION: (1)..(19)
<223> OTHER INFORMATION: 2'-O-methyl on all C and U residues
<220> FEATURE:
<221> NAME/KEY: misc_feature
<222> LOCATION: (19)..(19)
<223> OTHER INFORMATION: cholesterol conjugate linked to 3' end of sense
      nucleotide: cholesteryl 5-(bis(4-methoxyphenyl)(phenyl)methoxy)-3
      hydroxypentylcarbamate)

<400> SEQUENCE: 53
caccgucagg uugaauguu                                                 19

<210> SEQ ID NO 54
<211> LENGTH: 19
<212> TYPE: RNA
<213> ORGANISM: Artificial sequence
<220> FEATURE:
<223> OTHER INFORMATION: Sense strand sequence
<220> FEATURE:
<221> NAME/KEY: modified_base
<222> LOCATION: (1)..(2)
<223> OTHER INFORMATION: 2'-O-methyl
<220> FEATURE:
<221> NAME/KEY: modified_base
<222> LOCATION: (1)..(19)
<223> OTHER INFORMATION: 2'-O-methyl on all C and U residues
<220> FEATURE:
<221> NAME/KEY: misc_feature
<222> LOCATION: (19)..(19)
```

```
<223> OTHER INFORMATION: cholesterol conjugate linked to 3' end of sense
      nucleotide: cholesteryl 5-(bis(4-methoxyphenyl)(phenyl)methoxy)-3
      hydroxypentylcarbamate)

<400> SEQUENCE: 54
caccgucagg uugaaugua                                                    19

<210> SEQ ID NO 55
<211> LENGTH: 19
<212> TYPE: RNA
<213> ORGANISM: Artificial sequence
<220> FEATURE:
<223> OTHER INFORMATION: Sense strand sequence
<220> FEATURE:
<221> NAME/KEY: modified_base
<222> LOCATION: (1)..(2)
<223> OTHER INFORMATION: 2'-O-methyl
<220> FEATURE:
<221> NAME/KEY: modified_base
<222> LOCATION: (1)..(19)
<223> OTHER INFORMATION: 2'-O-methyl on all C and U residues
<220> FEATURE:
<221> NAME/KEY: misc_feature
<222> LOCATION: (19)..(19)
<223> OTHER INFORMATION: cholesterol conjugate linked to 3' end of sense
      nucleotide: cholesteryl 5-(bis(4-methoxyphenyl)(phenyl)methoxy)-3
      hydroxypentylcarbamate)

<400> SEQUENCE: 55
caccgucagg uucaaugua                                                    19

<210> SEQ ID NO 56
<211> LENGTH: 21
<212> TYPE: RNA
<213> ORGANISM: Artificial sequence
<220> FEATURE:
<223> OTHER INFORMATION: Antisense strand sequence
<220> FEATURE:
<221> NAME/KEY: misc_feature
<222> LOCATION: (1)..(1)
<223> OTHER INFORMATION: phosphorylation on 5' end of nucleotide
<220> FEATURE:
<221> NAME/KEY: modified_base
<222> LOCATION: (1)..(21)
<223> OTHER INFORMATION: 2'-F on all C and U residues
<220> FEATURE:
<221> NAME/KEY: modified_base
<222> LOCATION: (20)..(21)
<223> OTHER INFORMATION: phosphorothioate modified internucleotide
      linkages

<400> SEQUENCE: 56
uagguaguuu cauguuguuu u                                                 21

<210> SEQ ID NO 57
<211> LENGTH: 19
<212> TYPE: RNA
<213> ORGANISM: Artificial sequence
<220> FEATURE:
<223> OTHER INFORMATION: Sense strand sequence
<220> FEATURE:
<221> NAME/KEY: modified_base
<222> LOCATION: (1)..(2)
<223> OTHER INFORMATION: 2'-O-methyl
<220> FEATURE:
<221> NAME/KEY: modified_base
<222> LOCATION: (1)..(19)
<223> OTHER INFORMATION: 2'-O-methyl on all C and U residues
<220> FEATURE:
<221> NAME/KEY: misc_feature
<222> LOCATION: (19)..(19)
<223> OTHER INFORMATION: cholesterol conjugate linked to 3' end of sense
      nucleotide: cholesteryl 5-(bis(4-methoxyphenyl)(phenyl)methoxy)-3
      hydroxypentylcarbamate)
```

```
<400> SEQUENCE: 57
aacaacauga aacuaccua                                              19

<210> SEQ ID NO 58
<211> LENGTH: 19
<212> TYPE: RNA
<213> ORGANISM: Artificial sequence
<220> FEATURE:
<223> OTHER INFORMATION: Sense strand sequence
<220> FEATURE:
<221> NAME/KEY: Artificial sequence
<222> LOCATION: (1)..(2)
<223> OTHER INFORMATION: 2'-O-methyl
<220> FEATURE:
<221> NAME/KEY: modified_base
<222> LOCATION: (1)..(19)
<223> OTHER INFORMATION: 2'-O-methyl on all C and U residues
<220> FEATURE:
<221> NAME/KEY: misc_feature
<222> LOCATION: (19)..(19)
<223> OTHER INFORMATION: cholesterol conjugate linked to 3' end of sense
      nucleotide: cholesteryl 5-(bis(4-methoxyphenyl)(phenyl)methoxy)-3
      hydroxypentylcarbamate)

<400> SEQUENCE: 58
aacaagauga aacuaccua                                              19

<210> SEQ ID NO 59
<211> LENGTH: 19
<212> TYPE: RNA
<213> ORGANISM: Artificial sequence
<220> FEATURE:
<223> OTHER INFORMATION: Sense strand sequence
<220> FEATURE:
<221> NAME/KEY: modified_base
<222> LOCATION: (1)..(2)
<223> OTHER INFORMATION: 2'-O-methyl
<220> FEATURE:
<221> NAME/KEY: modified_base
<222> LOCATION: (1)..(19)
<223> OTHER INFORMATION: 2'-O-methyl on all C and U residues
<220> FEATURE:
<221> NAME/KEY: misc_feature
<222> LOCATION: (19)..(19)
<223> OTHER INFORMATION: cholesterol conjugate linked to 3' end of sense
      nucleotide: cholesteryl 5-(bis(4-methoxyphenyl)(phenyl)methoxy)-3
      hydroxypentylcarbamate)

<400> SEQUENCE: 59
aacaagauga aacuaccuu                                              19

<210> SEQ ID NO 60
<211> LENGTH: 19
<212> TYPE: RNA
<213> ORGANISM: Artificial sequence
<220> FEATURE:
<223> OTHER INFORMATION: Sense strand sequence
<220> FEATURE:
<221> NAME/KEY: modified_base
<222> LOCATION: (1)..(2)
<223> OTHER INFORMATION: 2'-O-methyl
<220> FEATURE:
<221> NAME/KEY: modified_base
<222> LOCATION: (1)..(19)
<223> OTHER INFORMATION: 2'-O-methyl on all C and U residues
<220> FEATURE:
<221> NAME/KEY: misc_feature
<222> LOCATION: (19)..(19)
<223> OTHER INFORMATION: cholesterol conjugate linked to 3' end of sense
      nucleotide: cholesteryl 5-(bis(4-methoxyphenyl)(phenyl)methoxy)-3
      hydroxypentylcarbamate)

<400> SEQUENCE: 60
```
aacaagauga aaguaccuu                                         19

<210> SEQ ID NO 61
<211> LENGTH: 21
<212> TYPE: RNA
<213> ORGANISM: Artificial sequence
<220> FEATURE:
<223> OTHER INFORMATION: Antisense strand sequence
<220> FEATURE:
<221> NAME/KEY: misc_feature
<222> LOCATION: (1)..(1)
<223> OTHER INFORMATION: phosphorylation on 5' end of nucleotide
<220> FEATURE:
<221> NAME/KEY: modified_base
<222> LOCATION: (1)..(21)
<223> OTHER INFORMATION: 2'-F on all C and U residues
<220> FEATURE:
<221> NAME/KEY: modified_base
<222> LOCATION: (20)..(21)
<223> OTHER INFORMATION: phosphorothioate modified internucleotide
      linkages

<400> SEQUENCE: 61
uccuucauuc caccggaguu u                                      21

<210> SEQ ID NO 62
<211> LENGTH: 19
<212> TYPE: RNA
<213> ORGANISM: Artificial sequence
<220> FEATURE:
<223> OTHER INFORMATION: Sense strand sequence
<220> FEATURE:
<221> NAME/KEY: modified_base
<222> LOCATION: (1)..(2)
<223> OTHER INFORMATION: 2'-O-methyl
<220> FEATURE:
<221> NAME/KEY: modified_base
<222> LOCATION: (1)..(19)
<223> OTHER INFORMATION: 2'-O-methyl on all C and U residues
<220> FEATURE:
<221> NAME/KEY: misc_feature
<222> LOCATION: (19)..(19)
<223> OTHER INFORMATION: cholesterol conjugate linked to 3' end of sense
      nucleotide: cholesteryl 5-(bis(4-methoxyphenyl)(phenyl)methoxy)-3
      hydroxypentylcarbamate)

<400> SEQUENCE: 62
acuccggugg aaugaagga                                         19

<210> SEQ ID NO 63
<211> LENGTH: 19
<212> TYPE: RNA
<213> ORGANISM: Artificial sequence
<220> FEATURE:
<223> OTHER INFORMATION: Sense strand sequence
<220> FEATURE:
<221> NAME/KEY: modified_base
<222> LOCATION: (1)..(2)
<223> OTHER INFORMATION: 2'-O-methyl
<220> FEATURE:
<221> NAME/KEY: modified_base
<222> LOCATION: (1)..(19)
<223> OTHER INFORMATION: 2'-O-methyl on all C and U residues
<220> FEATURE:
<221> NAME/KEY: misc_feature
<222> LOCATION: (19)..(19)
<223> OTHER INFORMATION: cholesterol conjugate linked to 3' end of sense
      nucleotide: cholesteryl 5-(bis(4-methoxyphenyl)(phenyl)methoxy)-3
      hydroxypentylcarbamate)

<400> SEQUENCE: 63
acucccgugg aaugaagga                                         19

<210> SEQ ID NO 64
<211> LENGTH: 19
<212> TYPE: RNA
<213> ORGANISM: Artificial sequence
<220> FEATURE:
<223> OTHER INFORMATION: Sense strand sequence
<220> FEATURE:
<221> NAME/KEY: modified_base
<222> LOCATION: (1)..(2)
<223> OTHER INFORMATION: 2'-O-methyl
<220> FEATURE:
<221> NAME/KEY: modified_base
<222> LOCATION: (1)..(19)
<223> OTHER INFORMATION: 2'-O-methyl on all C and U residues
<220> FEATURE:
<221> NAME/KEY: misc_feature
<222> LOCATION: (19)..(19)
<223> OTHER INFORMATION: cholesterol conjugate linked to 3' end of sense
    nucleotide: cholesteryl 5-(bis(4-methoxyphenyl)(phenyl)methoxy)-3
    hydroxypentylcarbamate)

<400> SEQUENCE: 64
acucccgugg aaugaaggu                                              19

<210> SEQ ID NO 65
<211> LENGTH: 19
<212> TYPE: RNA
<213> ORGANISM: Artificial sequence
<220> FEATURE:
<223> OTHER INFORMATION: Sense strand sequence
<220> FEATURE:
<221> NAME/KEY: modified_base
<222> LOCATION: (1)..(2)
<223> OTHER INFORMATION: 2'-O-methyl
<220> FEATURE:
<221> NAME/KEY: modified_base
<222> LOCATION: (1)..(19)
<223> OTHER INFORMATION: 2'-O-methyl on all C and U residues
<220> FEATURE:
<221> NAME/KEY: misc_feature
<222> LOCATION: (19)..(19)
<223> OTHER INFORMATION: cholesterol conjugate linked to 3' end of sense
    nucleotide: cholesteryl 5-(bis(4-methoxyphenyl)(phenyl)methoxy)-3
    hydroxypentylcarbamate)

<400> SEQUENCE: 65
acucccgugg aaagaaggu                                              19

<210> SEQ ID NO 66
<211> LENGTH: 21
<212> TYPE: RNA
<213> ORGANISM: Artificial sequence
<220> FEATURE:
<223> OTHER INFORMATION: Antisense strand sequence
<220> FEATURE:
<221> NAME/KEY: misc_feature
<222> LOCATION: (1)..(1)
<223> OTHER INFORMATION: phosphorylation on 5' end of nucleotide
<220> FEATURE:
<221> NAME/KEY: modified_base
<222> LOCATION: (1)..(21)
<223> OTHER INFORMATION: 2'-F on all C and U residues
<220> FEATURE:
<221> NAME/KEY: modified_base
<222> LOCATION: (20)..(21)
<223> OTHER INFORMATION: phosphorothioate modified internucleotide
    linkages

<400> SEQUENCE: 66
uggaauguaa ggaagugugu u                                           21

<210> SEQ ID NO 67
<211> LENGTH: 19

```
-continued

<212> TYPE: RNA
<213> ORGANISM: Artificial sequence
<220> FEATURE:
<223> OTHER INFORMATION: Sense strand sequence
<220> FEATURE:
<221> NAME/KEY: modified_base
<222> LOCATION: (1)..(2)
<223> OTHER INFORMATION: 2'-O-methyl
<220> FEATURE:
<221> NAME/KEY: modified_base
<222> LOCATION: (1)..(19)
<223> OTHER INFORMATION: 2'-O-methyl on all C and U residues
<220> FEATURE:
<221> NAME/KEY: misc_feature
<222> LOCATION: (19)..(19)
<223> OTHER INFORMATION: cholesterol conjugate linked to 3' end of sense
      nucleotide: cholesteryl 5-(bis(4-methoxyphenyl)(phenyl)methoxy)-3
      hydroxypentylcarbamate)

<400> SEQUENCE: 67
cacacuuccu uacauucca                                                    19

<210> SEQ ID NO 68
<211> LENGTH: 19
<212> TYPE: RNA
<213> ORGANISM: Artificial sequence
<220> FEATURE:
<223> OTHER INFORMATION: Sense strand sequence
<220> FEATURE:
<221> NAME/KEY: modified_base
<222> LOCATION: (1)..(2)
<223> OTHER INFORMATION: 2'-O-methyl
<220> FEATURE:
<221> NAME/KEY: modified_base
<222> LOCATION: (1)..(19)
<223> OTHER INFORMATION: 2'-O-methyl on all C and U residues
<220> FEATURE:
<221> NAME/KEY: misc_feature
<222> LOCATION: (19)..(19)
<223> OTHER INFORMATION: cholesterol conjugate linked to 3' end of sense
      nucleotide: cholesteryl 5-(bis(4-methoxyphenyl)(phenyl)methoxy)-3
      hydroxypentylcarbamate)

<400> SEQUENCE: 68
cacacauccu uacauucca                                                    19

<210> SEQ ID NO 69
<211> LENGTH: 19
<212> TYPE: RNA
<213> ORGANISM: Artificial sequence
<220> FEATURE:
<223> OTHER INFORMATION: Sense strand sequence
<220> FEATURE:
<221> NAME/KEY: modified_base
<222> LOCATION: (1)..(2)
<223> OTHER INFORMATION: 2'-O-methyl
<220> FEATURE:
<221> NAME/KEY: modified_base
<222> LOCATION: (1)..(19)
<223> OTHER INFORMATION: 2'-O-methyl on all C and U residues
<220> FEATURE:
<221> NAME/KEY: misc_feature
<222> LOCATION: (19)..(19)
<223> OTHER INFORMATION: cholesterol conjugate linked to 3' end of sense
      nucleotide: cholesteryl 5-(bis(4-methoxyphenyl)(phenyl)methoxy)-3
      hydroxypentylcarbamate)

<400> SEQUENCE: 69
cacacauccu uacauuccu                                                    19

<210> SEQ ID NO 70
<211> LENGTH: 19
<212> TYPE: RNA
<213> ORGANISM: Artificial sequence
```

```
<220> FEATURE:
<223> OTHER INFORMATION: Sense strand sequence
<220> FEATURE:
<221> NAME/KEY: modified_base
<222> LOCATION: (1)..(2)
<223> OTHER INFORMATION: 2'-O-methyl
<220> FEATURE:
<221> NAME/KEY: modified_base
<222> LOCATION: (1)..(19)
<223> OTHER INFORMATION: 2'-O-methyl on all C and U residues
<220> FEATURE:
<221> NAME/KEY: misc_feature
<222> LOCATION: (19)..(19)
<223> OTHER INFORMATION: cholesterol conjugate linked to 3' end of sense
      nucleotide: cholesteryl 5-(bis(4-methoxyphenyl)(phenyl)methoxy)-3
      hydroxypentylcarbamate)

<400> SEQUENCE: 70
cacacauccu uagauuccu                                                     19

<210> SEQ ID NO 71
<211> LENGTH: 21
<212> TYPE: RNA
<213> ORGANISM: Artificial sequence
<220> FEATURE:
<223> OTHER INFORMATION: Antisense strand sequence
<220> FEATURE:
<221> NAME/KEY: misc_feature
<222> LOCATION: (1)..(1)
<223> OTHER INFORMATION: phosphorylation on 5' end of nucleotide
<220> FEATURE:
<221> NAME/KEY: modified_base
<222> LOCATION: (1)..(21)
<223> OTHER INFORMATION: 2'-F on all C and U residues
<220> FEATURE:
<221> NAME/KEY: modified_base
<222> LOCATION: (20)..(21)
<223> OTHER INFORMATION: phosphorothioate modified internucleotide
      linkages

<400> SEQUENCE: 71
cugugcgugu gacagcggcu u                                                  21

<210> SEQ ID NO 72
<211> LENGTH: 19
<212> TYPE: RNA
<213> ORGANISM: Artificial sequence
<220> FEATURE:
<223> OTHER INFORMATION: Sense strand sequence
<220> FEATURE:
<221> NAME/KEY: modified_base
<222> LOCATION: (1)..(2)
<223> OTHER INFORMATION: 2'-O-methyl
<220> FEATURE:
<221> NAME/KEY: modified_base
<222> LOCATION: (1)..(19)
<223> OTHER INFORMATION: 2'-O-methyl on all C and U residues
<220> FEATURE:
<221> NAME/KEY: misc_feature
<222> LOCATION: (19)..(19)
<223> OTHER INFORMATION: cholesterol conjugate linked to 3' end of sense
      nucleotide: cholesteryl 5-(bis(4-methoxyphenyl)(phenyl)methoxy)-3
      hydroxypentylcarbamate)

<400> SEQUENCE: 72
gccgcuguca cacgcacag                                                     19

<210> SEQ ID NO 73
<211> LENGTH: 19
<212> TYPE: RNA
<213> ORGANISM: Artificial sequence
<220> FEATURE:
<223> OTHER INFORMATION: Sense strand sequence
<220> FEATURE:
```

```
<221> NAME/KEY: modified_base
<222> LOCATION: (1)..(2)
<223> OTHER INFORMATION: 2'-O-methyl
<220> FEATURE:
<221> NAME/KEY: modified_base
<222> LOCATION: (1)..(19)
<223> OTHER INFORMATION: 2'-O-methyl on all C and U residues
<220> FEATURE:
<221> NAME/KEY: misc_feature
<222> LOCATION: (19)..(19)
<223> OTHER INFORMATION: cholesterol conjugate linked to 3' end of sense
      nucleotide: cholesteryl 5-(bis(4-methoxyphenyl)(phenyl)methoxy)-3
      hydroxypentylcarbamate)

<400> SEQUENCE: 73
gccgcaguca cacgcacag                                                  19

<210> SEQ ID NO 74
<211> LENGTH: 19
<212> TYPE: RNA
<213> ORGANISM: Artificial sequence
<220> FEATURE:
<223> OTHER INFORMATION: Sense strand sequence
<220> FEATURE:
<221> NAME/KEY: modified_base
<222> LOCATION: (1)..(2)
<223> OTHER INFORMATION: 2'-O-methyl
<220> FEATURE:
<221> NAME/KEY: modified_base
<222> LOCATION: (1)..(19)
<223> OTHER INFORMATION: 2'-O-methyl on all C and U residues
<220> FEATURE:
<221> NAME/KEY: misc_feature
<222> LOCATION: (19)..(19)
<223> OTHER INFORMATION: cholesterol conjugate linked to 3' end of sense
      nucleotide: cholesteryl 5-(bis(4-methoxyphenyl)(phenyl)methoxy)-3
      hydroxypentylcarbamate)

<400> SEQUENCE: 74
gccgcaguca cacgcacac                                                  19

<210> SEQ ID NO 75
<211> LENGTH: 19
<212> TYPE: RNA
<213> ORGANISM: Artificial sequence
<220> FEATURE:
<223> OTHER INFORMATION: Sense strand sequence
<220> FEATURE:
<221> NAME/KEY: modified_base
<222> LOCATION: (1)..(2)
<223> OTHER INFORMATION: 2'-O-methyl
<220> FEATURE:
<221> NAME/KEY: modified_base
<222> LOCATION: (1)..(19)
<223> OTHER INFORMATION: 2'-O-methyl on all C and U residues
<220> FEATURE:
<221> NAME/KEY: misc_feature
<222> LOCATION: (19)..(19)
<223> OTHER INFORMATION: cholesterol conjugate linked to 3' end of sense
      nucleotide: cholesteryl 5-(bis(4-methoxyphenyl)(phenyl)methoxy)-3
      hydroxypentylcarbamate)

<400> SEQUENCE: 75
gccgcaguca caggcacac                                                  19

<210> SEQ ID NO 76
<211> LENGTH: 21
<212> TYPE: RNA
<213> ORGANISM: Artificial sequence
<220> FEATURE:
<223> OTHER INFORMATION: Antisense strand sequence
<220> FEATURE:
<221> NAME/KEY: misc_feature
<222> LOCATION: (1)..(1)
```

```
<223> OTHER INFORMATION: phosphorylation on 5' end of nucleotide
<220> FEATURE:
<221> NAME/KEY: modified_base
<222> LOCATION: (1)..(21)
<223> OTHER INFORMATION: 2'-F on all C and U residues
<220> FEATURE:
<221> NAME/KEY: modified_base
<222> LOCATION: (20)..(21)
<223> OTHER INFORMATION: phosphorothioate modified internucleotide
      linkages

<400> SEQUENCE: 76
aaaagcuggg uugagagggu u                                          21

<210> SEQ ID NO 77
<211> LENGTH: 19
<212> TYPE: RNA
<213> ORGANISM: Artificial sequence
<220> FEATURE:
<223> OTHER INFORMATION: Sense strand sequence
<220> FEATURE:
<221> NAME/KEY: modified_base
<222> LOCATION: (1)..(2)
<223> OTHER INFORMATION: 2'-O-methyl
<220> FEATURE:
<221> NAME/KEY: modified_base
<222> LOCATION: (1)..(19)
<223> OTHER INFORMATION: 2'-O-methyl on all C and U residues
<220> FEATURE:
<221> NAME/KEY: misc_feature
<222> LOCATION: (19)..(19)
<223> OTHER INFORMATION: cholesterol conjugate linked to 3' end of sense
      nucleotide: cholesteryl 5-(bis(4-methoxyphenyl)(phenyl)methoxy)-3
      hydroxypentylcarbamate)

<400> SEQUENCE: 77
cccucucaac ccagcuuuu                                             19

<210> SEQ ID NO 78
<211> LENGTH: 19
<212> TYPE: RNA
<213> ORGANISM: Artificial sequence
<220> FEATURE:
<223> OTHER INFORMATION: Sense strand sequence
<220> FEATURE:
<221> NAME/KEY: modified_base
<222> LOCATION: (1)..(2)
<223> OTHER INFORMATION: 2'-O-methyl
<220> FEATURE:
<221> NAME/KEY: modified_base
<222> LOCATION: (1)..(19)
<223> OTHER INFORMATION: 2'-O-methyl on all C and U residues
<220> FEATURE:
<221> NAME/KEY: misc_feature
<222> LOCATION: (19)..(19)
<223> OTHER INFORMATION: cholesterol conjugate linked to 3' end of sense
      nucleotide: cholesteryl 5-(bis(4-methoxyphenyl)(phenyl)methoxy)-3
      hydroxypentylcarbamate)

<400> SEQUENCE: 78
cccucacaac ccagcuuuu                                             19

<210> SEQ ID NO 79
<211> LENGTH: 19
<212> TYPE: RNA
<213> ORGANISM: Artificial sequence
<220> FEATURE:
<223> OTHER INFORMATION: Sense strand sequence
<220> FEATURE:
<221> NAME/KEY: modified_base
<222> LOCATION: (1)..(2)
<223> OTHER INFORMATION: 2'-O-methyl
<220> FEATURE:
<221> NAME/KEY: modified_base
```

```
<222> LOCATION: (1)..(19)
<223> OTHER INFORMATION: 2'-O-methyl on all C and U residues
<220> FEATURE:
<221> NAME/KEY: misc_feature
<222> LOCATION: (19)..(19)
<223> OTHER INFORMATION: cholesterol conjugate linked to 3' end of sense
      nucleotide: cholesteryl 5-(bis(4-methoxyphenyl)(phenyl)methoxy)-3
      hydroxypentylcarbamate)

<400> SEQUENCE: 79
cccucacaac ccagcuuua                                                  19

<210> SEQ ID NO 80
<211> LENGTH: 19
<212> TYPE: RNA
<213> ORGANISM: Artificial sequence
<220> FEATURE:
<223> OTHER INFORMATION: Sense strand sequence
<220> FEATURE:
<221> NAME/KEY: modified_base
<222> LOCATION: (1)..(2)
<223> OTHER INFORMATION: 2'-O-methyl
<220> FEATURE:
<221> NAME/KEY: modified_base
<222> LOCATION: (1)..(19)
<223> OTHER INFORMATION: 2'-O-methyl on all C and U residues
<220> FEATURE:
<221> NAME/KEY: misc_feature
<222> LOCATION: (19)..(19)
<223> OTHER INFORMATION: cholesterol conjugate linked to 3' end of sense
      nucleotide: cholesteryl 5-(bis(4-methoxyphenyl)(phenyl)methoxy)-3
      hydroxypentylcarbamate)

<400> SEQUENCE: 80
cccucacaac ccugcuuua                                                  19

<210> SEQ ID NO 81
<211> LENGTH: 21
<212> TYPE: RNA
<213> ORGANISM: Artificial sequence
<220> FEATURE:
<223> OTHER INFORMATION: Antisense strand sequence
<220> FEATURE:
<221> NAME/KEY: misc_feature
<222> LOCATION: (1)..(1)
<223> OTHER INFORMATION: phosphorylation on 5' end of nucleotide
<220> FEATURE:
<221> NAME/KEY: modified_base
<222> LOCATION: (1)..(21)
<223> OTHER INFORMATION: 2'-F on all C and U residues
<220> FEATURE:
<221> NAME/KEY: modified_base
<222> LOCATION: (20)..(21)
<223> OTHER INFORMATION: phosphorothioate modified internucleotide
      linkages

<400> SEQUENCE: 81
uuuguucguu cggcucgcgu u                                               21

<210> SEQ ID NO 82
<211> LENGTH: 19
<212> TYPE: RNA
<213> ORGANISM: Artificial sequence
<220> FEATURE:
<223> OTHER INFORMATION: Sense strand sequence
<220> FEATURE:
<221> NAME/KEY: modified_base
<222> LOCATION: (1)..(2)
<223> OTHER INFORMATION: 2'-O-methyl
<220> FEATURE:
<221> NAME/KEY: modified_base
<222> LOCATION: (1)..(19)
<223> OTHER INFORMATION: 2'-O-methyl on all C and U residues
<220> FEATURE:
```

```
<221> NAME/KEY: misc_feature
<222> LOCATION: (19)..(19)
<223> OTHER INFORMATION: cholesterol conjugate linked to 3' end of sense
      nucleotide: cholesteryl 5-(bis(4-methoxyphenyl)(phenyl)methoxy)-3
      hydroxypentylcarbamate)

<400> SEQUENCE: 82
cgcgagccga acgaacaaa                                                      19

<210> SEQ ID NO 83
<211> LENGTH: 19
<212> TYPE: RNA
<213> ORGANISM: Artificial sequence
<220> FEATURE:
<223> OTHER INFORMATION: Sense strand sequence
<220> FEATURE:
<221> NAME/KEY: modified_base
<222> LOCATION: (1)..(2)
<223> OTHER INFORMATION: 2'-O-methyl
<220> FEATURE:
<221> NAME/KEY: modified_base
<222> LOCATION: (1)..(19)
<223> OTHER INFORMATION: 2'-O-methyl on all C and U residues
<220> FEATURE:
<221> NAME/KEY: misc_feature
<222> LOCATION: (19)..(19)
<223> OTHER INFORMATION: cholesterol conjugate linked to 3' end of sense
      nucleotide: cholesteryl 5-(bis(4-methoxyphenyl)(phenyl)methoxy)-3
      hydroxypentylcarbamate)

<400> SEQUENCE: 83
cgcgacccga acgaacaaa                                                      19

<210> SEQ ID NO 84
<211> LENGTH: 19
<212> TYPE: RNA
<213> ORGANISM: Artificial sequence
<220> FEATURE:
<223> OTHER INFORMATION: Sense strand sequence
<220> FEATURE:
<221> NAME/KEY: modified_base
<222> LOCATION: (1)..(2)
<223> OTHER INFORMATION: 2'-O-methyl
<220> FEATURE:
<221> NAME/KEY: modified_base
<222> LOCATION: (1)..(19)
<223> OTHER INFORMATION: 2'-O-methyl on all C and U residues
<220> FEATURE:
<221> NAME/KEY: misc_feature
<222> LOCATION: (19)..(19)
<223> OTHER INFORMATION: cholesterol conjugate linked to 3' end of sense
      nucleotide: cholesteryl 5-(bis(4-methoxyphenyl)(phenyl)methoxy)-3
      hydroxypentylcarbamate)

<400> SEQUENCE: 84
cgcgacccga acgaacaau                                                      19

<210> SEQ ID NO 85
<211> LENGTH: 19
<212> TYPE: RNA
<213> ORGANISM: Artificial sequence
<220> FEATURE:
<223> OTHER INFORMATION: Sense strand sequence
<220> FEATURE:
<221> NAME/KEY: modified_base
<222> LOCATION: (1)..(2)
<223> OTHER INFORMATION: 2'-O-methyl
<220> FEATURE:
<221> NAME/KEY: modified_base
<222> LOCATION: (1)..(19)
<223> OTHER INFORMATION: 2'-O-methyl on all C and U residues
<220> FEATURE:
<221> NAME/KEY: misc_feature
<222> LOCATION: (19)..(19)
```

```
<223> OTHER INFORMATION: cholesterol conjugate linked to 3' end of sense
      nucleotide: cholesteryl 5-(bis(4-methoxyphenyl)(phenyl)methoxy)-3
      hydroxypentylcarbamate)

<400> SEQUENCE: 85
cgcgacccga accaacaau                                                   19

<210> SEQ ID NO 86
<211> LENGTH: 22
<212> TYPE: RNA
<213> ORGANISM: Artificial sequence
<220> FEATURE:
<223> OTHER INFORMATION: Antisense strand sequence

<400> SEQUENCE: 86
uggaguguga caaugguguu ug                                               22

<210> SEQ ID NO 87
<211> LENGTH: 54
<212> TYPE: RNA
<213> ORGANISM: Artificial sequence
<220> FEATURE:
<223> OTHER INFORMATION: miRNA
<220> FEATURE:
<221> NAME/KEY: modified_base
<222> LOCATION: (1)..(54)
<223> OTHER INFORMATION: 2'-O-methyl

<400> SEQUENCE: 87
agcucugaaa agagcucaaa caccauuguc acuguccauc gagagcuuuc ucga            54
```

DUPLEX OLIGONUCLEOTIDES WITH ENHANCED FUNCTIONALITY IN GENE REGULATION

CROSS-REFERENCE TO RELATED APPLICATIONS

This application is a divisional application of U.S. Ser. No. 12/368,856, filed Feb. 10, 2009, which claims the benefit of U.S. Provisional Patent Application Ser. No. 61/027,609, filed Feb. 11, 2008, entitled "Duplex Oligonucleotides with Enhanced Functionality in Gene Regulation," the entire contents of both applications are incorporated by reference in their entireties.

FIELD OF THE DISCLOSURE

The disclosure relates to methods and compositions for gene regulation using RNA interference (RNAi). In particular, the disclosure relates to duplex oligonucleotide complexes, including siRNAs, miRNA mimics, and piRNA mimics, which contain modified nucleotides and mismatches between the two strands of the molecule at specific nucleotide positions.

BACKGROUND

Synthetic duplex oligonucleotides, in particular short interfering RNAs (siRNAs), small hairpin RNAs (shRNAs), Piwi-interacting RNA (piRNA) mimics, and microRNA (miRNA) mimics, modulate gene expression via the RNA interference pathway (RNAi), leading to the cleavage of specific messenger RNAs (mRNAs). In the case of miRNA mimics, translational repression of specific mRNAs may take place in addition to, or instead of, cleavage of the mRNA.

Two factors that affect overall performance of synthetic duplex oligonucleotides are stability against nuclease degradation and the annealing strength. Chemical modifications have been identified that alter stability and annealing. Addition of O-alkyl (e.g., O-methyl) groups or halogens to the 2' position of the ribose ring, and/or inter-nucleotide modifications to an oligonucleotide impedes degradation of these molecules by nucleases. At the same time, addition of 2'-O-alkyl groups can augment binding affinity and thus functionality.

Chemical modifications that can be added to the sense strand of an siRNA or miRNA mimic that enhance the stability and/or functionality of the duplex. See United States Patent Application Publication No. 2007/0269889, incorporated herein by reference in its entirety. These modifications, which comprise 2'-O-methyl modification of some or all of the nucleotides of the sense strand, minimize the nuclease sensitivity of the strand and enhance the entry of the antisense strand into the RNA interference silencing complex (RISC).

The inventors have now observed that addition of 2'-O-methyl modifications to the sense strand of e.g. miRNA mimics can, in some circumstances, have negative effects on that molecule. As these effects may be detrimental to the functionality of the molecule, it is desirable to identify modifications that can compensate for the negative properties.

SUMMARY OF THE DISCLOSURE

In a first aspect, the disclosure provides a duplex oligonucleotide complex comprising:

a. a sense strand that ranges in size from about 16 to about 31 nucleotides in which about 40% to about 90% of the nucleotides of the sense strand are chemically modified;

b. an antisense strand that ranges in size from about 16 to about 31 nucleotides in which about 40% to about 90% of the nucleotides of the antisense strand are chemically modified nucleotides;

c. at least one of:

a mismatch between nucleotide 1 on the antisense strand and the opposite nucleotide on the sense strand; and a mismatch between nucleotide 7 on the antisense strand and the opposite nucleotide on the sense strand.

The antisense strand has significant levels of complementarity to both the sense strand and a target gene, and the sense strand and the antisense strand form a duplex. In one embodiment, there is a mismatch between nucleotide 1 on the antisense strand and the opposite nucleotide on the sense strand. In another embodiment, there is a mismatch between nucleotide 7 on the antisense strand and the opposite nucleotide on the sense strand. In another embodiment there is a mismatch between nucleotide 1 on the antisense strand and the opposite nucleotide on the sense strand and also a mismatch between nucleotide 14 on the antisense strand and the opposite nucleotide on the sense strand. In another embodiment there is a mismatch between nucleotide 1 on the antisense strand and the opposite nucleotide on the sense strand and also a mismatch between nucleotide 7 on the antisense strand and the opposite nucleotide on the sense strand. In another embodiment there is a mismatch between nucleotide 7 on the antisense strand and the opposite nucleotide on the sense strand and also a mismatch between nucleotide 14 on the antisense strand and the opposite nucleotide on said sense strand. In another embodiment there is a mismatch between nucleotide 1 on the antisense strand and the opposite nucleotide on the sense strand, a mismatch between nucleotide 7 on the antisense strand and the opposite nucleotide on the sense strand, and a mismatch between nucleotide 14 on the antisense strand and the opposite nucleotide on the sense strand. The nucleotide positions in these embodiments are counted from the 5' end of the respective strands, not including any overhangs which may be present.

In one embodiment, the duplex oligonucleotide complex is a miRNA mimic, a siRNA, or a piRNA mimic.

In another embodiment of the first aspect of the disclosure, nucleotides 1 and 2 and all C nucleotides and all U nucleotides on the sense strand (counting from the 5' end and not including any overhang which may be present) are 2' O-methyl modified and all C nucleotides and all U nucleotides on the antisense strand are 2' F modified.

In another embodiment, a conjugate moiety selected from the group consisting of cholesterol, cholestanol, stigmasterol, cholanic acid, and ergosterol is attached to the sense strand via a linker molecule that is from about 3 to about 9 atoms in length. Preferably, the linker molecule is 5 to 8 atoms in length. Preferably, the linker molecule attaches the conjugate moiety to the 3' end of said sense strand. More preferably, the conjugate moiety is cholesterol, the linker molecule is 5 atoms in length, and the sense strand has the structure:

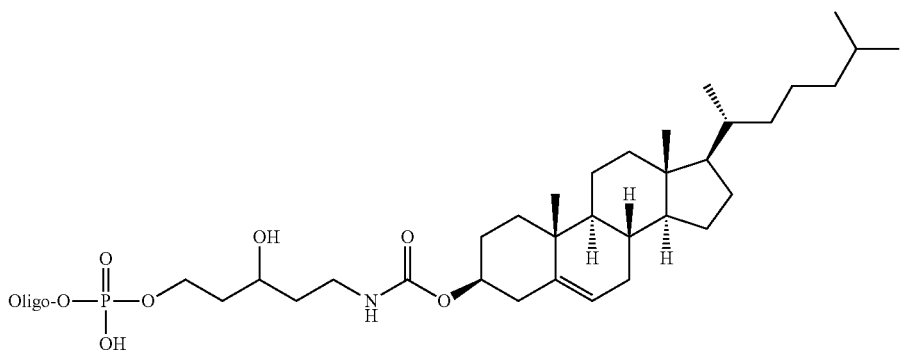

In another embodiment, the duplex oligonucleotide complex has a phosphate group at the 5' end of the antisense strand. In a yet further embodiment, the duplex oligonucleotide complex comprises an overhang at the 3' end of the antisense strand. Preferably, the overhang comprises phosphorothioate linkages.

In another embodiment, the disclosure provides a duplex oligonucleotide complex comprising:
  a. a sense strand that ranges in size from about 16 to about 31 nucleotides wherein nucleotides 1 and 2 and all C nucleotides and all U nucleotides are 2'O-methyl modified;
  b. an antisense strand that ranges in size from about 16 to about 31 nucleotides wherein all C nucleotides and all U nucleotides are 2' F modified, wherein the antisense strand has significant levels of complementarity to both the sense strand and a target gene and wherein the sense strand and the antisense strand form a duplex;
  c. a cholesterol molecule attached to the 3' end of the sense strand via a C5 linker molecule wherein the cholesterol-linker-sense strand has the structure:

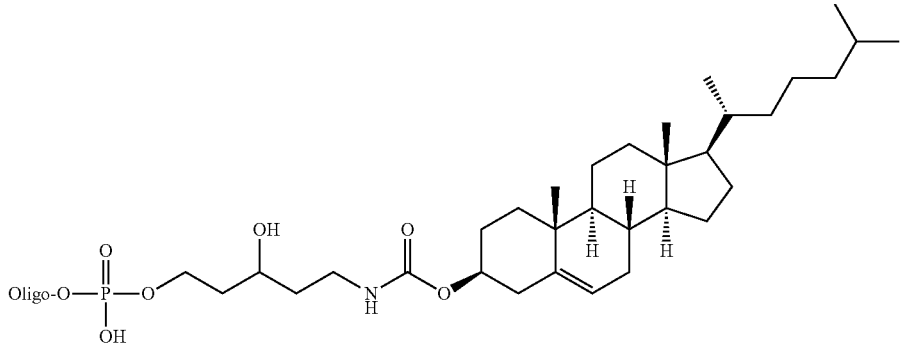

d. a phosphate group at the 5' end of the antisense strand;
  e. at least one of:
    a mismatch between nucleotide 1 on said antisense strand and the opposite nucleotide on said sense strand; and
    a mismatch between nucleotide 7 on said antisense strand and the opposite nucleotide on said sense strand; and
  f. a 2 nucleotide overhang at the 3' end of the antisense strand comprising phosphorothioate linkages.

In a second aspect, the disclosure provides a method for inhibiting expression of a target gene in a cell, the method comprising delivering to the cell a duplex oligonucleotide complex according to any of the aforementioned embodiments of the first aspect of the disclosure. In one embodiment, the duplex oligonucleotide complex is delivered to the cell by reverse transfection. In another embodiment, the duplex oligonucleotide complex is delivered to the cell in vivo.

In a third aspect, the disclosure provides a cell comprising a duplex oligonucleotide complex according to any of the aforementioned embodiments of the first aspect of the disclosure.

In a fourth aspect, the disclosure provides a pharmaceutical composition comprising a duplex oligonucleotide complex according to any of the aforementioned embodiments of the first aspect of the disclosure and further comprising at least one pharmaceutically acceptable carrier or diluent.

These and other aspects of the disclosure are now described in detail.

BRIEF DESCRIPTION OF THE DRAWINGS

FIG. 1C provides a schematic drawing showing the positions of mismatches in 19 bp and 22 bp duplexes. Additional nucleotides are added to the 5' and 3' termini of the sense and antisense oligonucleotides, respectively.

DETAILED DESCRIPTION OF THE DISCLOSURE

Definitions

Figure 1A:
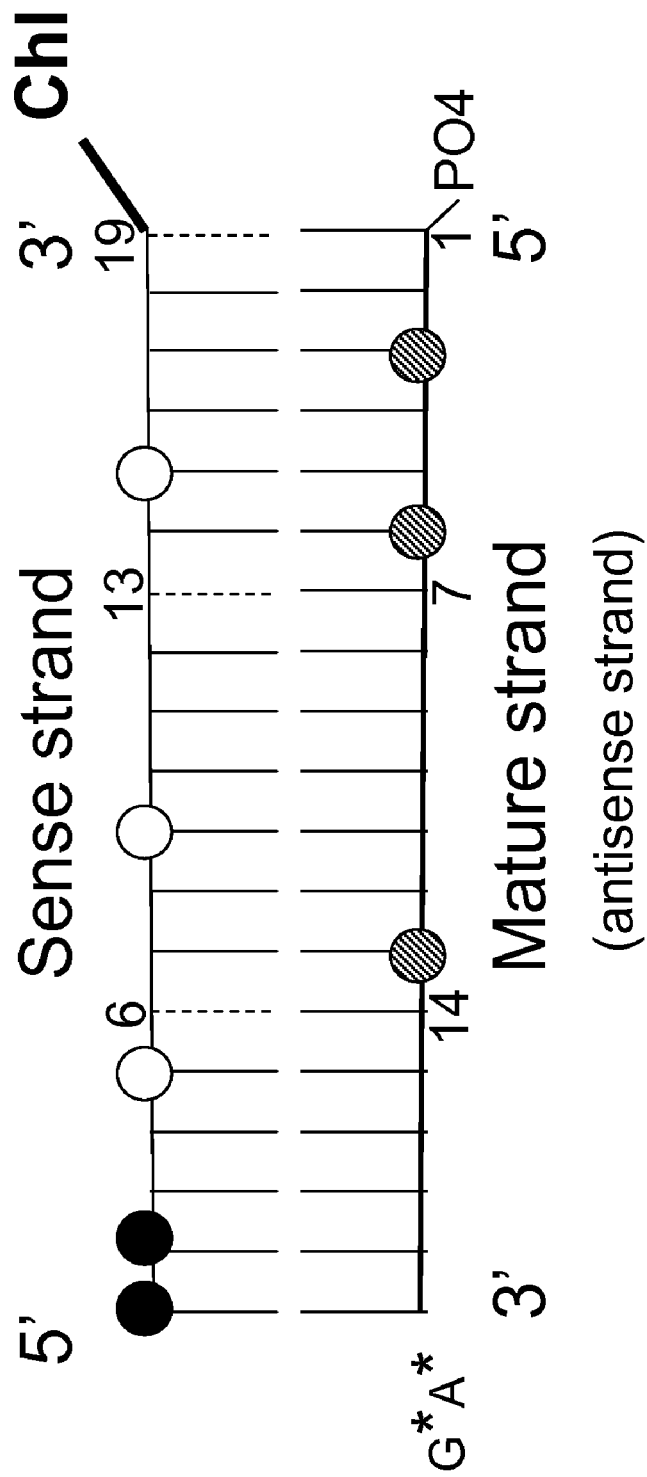
FIG. 1A provides a schematic drawing showing a preferred configuration of a mismatch-containing duplex molecule of the disclosure as it is applied to an siRNA. In this example, the sense strand contains (1) 2'-O-methyl modifications of positions 1 and 2 (black circles), (2) 2'-O-methyl modification of some or all Cs and/or Us (white circles), (3) an optional 3' cholesterol group (Ch1) linked to the oligonucleotide strand. One preferred linker consists of a C5 (e.g., cholesteryl 5-(bis(4-methoxyphenyl)(phenyl)methoxy)-3 hydroxypentylcarbamate) linker. (4) 2' F modifications on some or all Cs and/or Us on the mature (antisense) strand (hatched circles).

The term "nucleotide" refers to a ribonucleotide or a deoxyribonucleotide or modified form thereof, as well as an analog thereof. Nucleotides include species that comprise purines, e.g., adenine, hypoxanthine, guanine, and their derivatives and analogs, as well as pyrimidines, e.g., cytosine, uracil, thymine, and their derivatives and analogs. Preferably, a "nucleotide" comprises a cytosine, uracil, thymine, adenine, or guanine moiety. Further, the term nucleotide also includes those species that have a detectable label, such as for example a radioactive or fluorescent moiety, or mass label attached to the nucleotide.

The term "chemically modified nucleotide" refers to a nucleotide having modifications in the chemical structure of the base, sugar and/or phosphate, including, but not limited to, 5-position pyrimidine modifications, 8-position purine modifications, modifications at cytosine exocyclic amines, and substitution of 5-bromo-uracil; and 2'-position sugar modifications, including but not limited to, sugar-modified ribonucleotides in which the 2'-OH is replaced by a group such as an H, OR, R, halo, SH, SR, $NH_2$, NHR, $NR_2$, or CN, wherein R is an alkyl moiety as defined herein. Nucleotide analogs are also meant to include nucleotides with bases such as inosine, queuosine, xanthine, sugars such as 2'-methyl ribose, non-natural phosphodiester internucleotide linkages such as methylphosphonates, phosphorothioates and peptides.

Modified bases refer to nucleotide bases such as, for example, adenine, guanine, cytosine, thymine, and uracil, xanthine, inosine, and queuosine that have been modified by the replacement or addition of one or more atoms or groups. Some examples of types of modifications that can comprise nucleotides that are modified with respect to the base moieties, include but are not limited to, alkylated, halogenated, thiolated, aminated, amidated, or acetylated bases, in various combinations. More specific modified bases include, for example, 5-propynyluridine, 5-propynylcytidine, 6-methyladenine, 6-methylguanine, N,N,-dimethyladenine, 2-propyladenine, 2-propylguanine, 2-aminoadenine, 1-methylinosine, 3-methyluridine, 5-methylcytidine, 5-methyluridine and other nucleotides having a modification at the 5 position, 5-(2-amino)propyluridine, 5-halocytidine, 5-halouridine, 4-acetylcytidine, 1-methyladenosine, 2-methyladenosine, 3-methylcytidine, 6-methyluridine, 2-methylguanosine, 7-methylguanosine, 2,2-dimethylguanosine, 5-methylaminoethyluridine, 5-methyloxyuridine, deazanucleotides such as 7-deaza-adenosine, 6-azouridine, 6-azocytidine, 6-azothymidine, 5-methyl-2-thiouridine, other thio bases such as 2-thiouridine and 4-thiouridine and 2-thiocytidine, dihydrouridine, pseudouridine, queuosine, archaeosine, naphthyl and substituted naphthyl groups, any O- and N-alkylated purines and pyrimidines such as N6-methyladenosine, 5-methylcarbonylmethyluridine, uridine 5-oxyacetic acid, pyridine-4-one, pyridine-2-one, phenyl and modified phenyl groups such as aminophenol or 2,4,6-trimethoxy benzene, modified cytosines that act as G-clamp nucleotides, 8-substituted adenines and guanines, 5-substituted uracils and thymines, azapyrimidines, carboxyhydroxyalkyl nucleotides, carboxyalkylaminoalkyl nucleotides, and alkylcarbonylalkylated nucleotides. Modified nucleotides also include those nucleotides that are modified with respect to the sugar moiety, as well as nucleotides having sugars or analogs thereof that are not ribosyl. For example, the sugar moieties may be, or be based on, mannoses, arabinoses, glucopyranoses, galactopyranoses, 4-thioribose, and other sugars, heterocycles, or carbocycles. The term nucleotide is also meant to include what are known in the art as universal bases. By way of example, universal bases include but are not limited to 3-nitropyrrole, 5-nitroindole, or nebularine.

The phrase "2' carbon modification" refers to a nucleotide unit having a sugar moiety that is modified at the 2' position of the sugar subunit. A "2' carbon sense modification" refers to a modification at the 2' carbon position of a nucleotide on the sense strand or within a sense region of polynucleotide. A "2' carbon antisense modification" refers to a modification at the 2' carbon position of a nucleotide on the antisense strand or within an antisense region of polynucleotide. An example of a 2' carbon antisense modification can be e.g., 2' F modification of all Cs and Us.

The phrase "2'-O-alkyl modified nucleotide" refers to a nucleotide unit having a sugar moiety, for example a deoxyribosyl moiety that is modified at the 2' position such that an oxygen atom is attached both to the carbon atom located at the 2' position of the sugar and to an alkyl group. In various embodiments, the alkyl moiety consists essentially of carbons and hydrogens. A particularly preferred embodiment is one wherein the alkyl moiety is methyl moiety. A "2'-O-alkyl modified nucleotide" is modified at this position such that an oxygen atom is attached both to the carbon atom located at the 2' position of the sugar and to an alkyl group, e.g., 2'-O-methyl, 2'-O-ethyl, 2'-O-propyl, 2'-O-isopropyl, 2'-O-butyl, 2-O-isobutyl, 2'-O-ethyl-O-methyl(-OCH$_2$CH$_2$OCH$_3$), and 2'-O-ethyl-OH(—OCH$_2$CH$_2$OH).

The term "duplex" refers to a region of double-stranded structure formed by two antiparallel polynucleotide strands as a result of base-pairing between the strands. A duplex may be formed between two separate polynucleotides, or the strands may be contained with a single polynucleotide sequence e.g. a hairpin structure where the "loop" portion of the hairpin allows the two strands to adopt an antiparallel configuration relative to each other. A duplex structure may be interrupted by, e.g., mismatches and loops. For example, where two antiparallel strands are the same length but are not 100% complementary in sequence, duplex regions will be interrupted by regions where Watson-Crick base-pairing does not occur due to the presence of mismatches.

The term "hairpin" refers to a stem-loop structure. The stem results from two sequences of nucleic acid or modified nucleic acid annealing together to generate a duplex. The loop is a single stranded region that lies between the two strands comprising the stem.

The term "mature strand" (also referred to as the "antisense strand," "targeting strand" or "guide strand") refers to the strand of a fully processed miRNA, a piRNA, or an siRNA that enters RISC(RNA Induced Silencing Complex). In some cases, miRNAs have a single mature strand that can vary in length between about 16-31 nucleotides in length. In other instances, miRNAs can have two mature strands, and again, the length of the strands can vary between about 16 and about 31 nucleotides. In the present disclosure, the terms mature strand and antisense strand are used interchangeably.

The terms "microRNA inhibitor", "miR inhibitor", or "inhibitor" are synonymous and refer to polynucleotides or modified polynucleotides that interfere with the ability of specific miRNAs, piRNAs, or siRNAs to silence their intended targets. Inhibitors can adopt a variety of configurations including single stranded, double stranded, and hairpin designs (see PCT/US2007/004223, published as WO/2007/095387, incorporated herein by reference in its entirety). miRNA inhibitors also include modified nucleotides including but not limited to 2'-O-methyl modified and LNA modified molecules.

The term "microRNA mimic" refers to synthetic non-coding RNAs that are capable of entering the RNAi pathway and regulating gene expression. miRNA mimics imitate the function of endogenous microRNAs (miRNAs) and can be designed as mature, double stranded molecules or mimic precursors (e.g., pri- or pre-miRNAs). miRNA mimics can be comprised of modified or unmodified RNA, DNA, RNA-DNA hybrids, or alternative nucleic acid chemistries (e.g., locked nucleic acids (LNAs) or 2'-O, 4'-C ethylene bridged nucleic acids (ENAs)). For mature, double stranded miRNA mimics, the length of the duplex region can vary between about 16 and 31 nucleotides and chemical modification patterns can include the following: the sense strand contains 2'-O-methyl modifications of nucleotides 1 and 2 (counting from the 5' end of the sense oligonucleotide) and all the Cs and Us. In addition, the sense strand can comprise a conjugate that enhances functionality, delivery, or specificity. The antisense strand modifications may comprise 2' F modification of all the Cs and Us, phosphorylation of the 5' end of the oligonucleotide, and stabilized internucleotide linkages associated with a 2 nucleotide 3' overhang.

In the context of this document, the terms "micro RNA reporter" or "miR reporter", or "reporter" refer to a vector or plasmid construct that encodes one or more reporter genes including but not limited to firefly luciferase, *Renilla* luciferase, secreted alkaline phosphatase, green fluorescent protein, yellow fluorescent protein, or others, and has miRNA target sites (also referred to as "miRNA recognition elements (MREs), piRNA recognition sites (PREs), or siRNA recognition elements (SREs) inserted into the 5' UTR, ORF, and/or 3' UTR of one or more of the reporter genes.

The term "mismatch" includes a situation in which Watson-Crick base pairing does not take place between a nucleotide of a sense strand and a nucleotide of an antisense strand, where the nucleotides are flanked by a duplex comprising base pairs in the 5' direction of the mismatch beginning directly after (in the 5' direction) the mismatched position and in the 3' direction of the mismatch beginning directly after (in the 3' direction) the mismatched position. An example of a mismatch would be an A across from a G, a C across from an A, a U across from a C, an A across from an A, a G across from a G, a C across from a C, and so on. Mismatches are also meant to include an abasic residue across from a nucleotide or modified nucleotide, an acyclic residue across from a nucleotide or modified nucleotide, a gap, or an unpaired loop. In its broadest sense, a mismatch as used herein includes any alteration at a given position that decreases the thermodynamic stability at or in the vicinity of the position where the alteration appears, such that the thermodynamic stability of the duplex at the particular position is less than the thermodynamic stability of a Watson-Crick base pair at that position. Preferred mismatches include a G across from an A, and an A across from a C. A particularly preferred mismatch comprises an A across from an A, G across from a G, C across from a C, and U across from a U.

The term "overhang" refers to terminal non-base pairing nucleotide(s) resulting from one strand or region extending beyond the terminus of the complementary strand to which the first strand or region forms a duplex. One or both of two polynucleotides or polynucleotide regions that are capable of forming a duplex through hydrogen bonding of base pairs may have a 5' and/or 3' end that extends beyond the 3' and/or 5' end of complementarity shared by the two polynucleotides or regions. The single-stranded region extending beyond the 3' and/or 5' end of the duplex is referred to as an overhang. Typically, the overhang is between 1-6 nucleotides, in length and preferably at the 3' end of antisense strand. The nucleotides in the overhang can be modified for stability by the methods well known in the art.

The phrase "passive transfection" refers to the process whereby modified oligonucleotides can be introduced into cells in a lipid-independent manner i.e. without the participation of a separate lipid-containing transfection agent.

The term "piRNAs" refers to Piwi-interacting RNAs, a class of small RNAs that are believed to be involved in transcriptional silencing (see Lau, N. C. et al (2006) Science, 313:305-306).

The phrase "RNA interference" and the term "RNAi" are synonymous and refer to the process by which a polynucleotide or siRNA comprising at least one ribonucleotide unit exerts an effect on a biological process. The process includes, but is not limited to, gene silencing by degrading mRNA, attenuating translation, interactions with tRNA, rRNA, hnRNA, cDNA and genomic DNA, as well as methylation of DNA with ancillary proteins.

The term "siRNA" and the phrase "short interfering RNA" refer to unimolecular nucleic acids and to nucleic acids comprised of two separate strands that are capable of performing RNAi and that have a duplex region that is between 14 and 30 base pairs in length. Additionally, the term siRNA and the phrase "short interfering RNA" include nucleic acids that also contain moieties other than ribonucleotide moieties, including, but not limited to, modified nucleotides, modified internucleotide linkages, non-nucleotides, deoxynucleotides and analogs of the aforementioned nucleotides.

By "significant levels of complementarity to the sense strand as well as a target gene" is meant that the antisense strand possesses sufficient complementarity with the sense strand to allow a duplex to form, and also possesses sufficient complementarity with a target gene to allow RNA interference to occur following Dicer processing of the duplex oligonucleotide complex. The antisense strand preferably exhibits at least 80% complementary to the sense strand and to the target gene i.e. substantial complementarity.

siRNAs can be duplexes, and can also comprise short hairpin RNAs (shRNAs), RNAs with loops as long as, for example, 4 to 23 or more nucleotides, RNAs with stem loop bulges, micro-RNAs, and short temporal RNAs. RNAs having loops or hairpin loops can include structures where the loops are connected to the stem by linkers such as flexible linkers. Flexible linkers can be comprised of a wide variety of chemical structures, as long as they are of sufficient length and materials to enable effective intramolecular hybridization of the stem elements. Typically, the length to be spanned is at least about 10-24 atoms.

When the siRNAs are hairpins, the sense strand and antisense strand are part of one longer molecule.

The Duplex

The mismatches of the disclosure (described in detail below in the section entitled "Mismatches") can be added to siRNAs, piRNA mimics, or miRNA mimics which are double stranded oligonucleotides. Duplex lengths to which these modifications can be added can vary between about 16 and about 31 base pairs, although longer and shorter duplex lengths are also contemplated. Thus, for example, the sense and antisense strands may form a duplex that is 16, 17, 18, 19, 20, 21, 22, 23, 24, 25, 26, 27, 28, 29, 30, or 31 base pairs in length (not including any overhang(s) which may be present). Preferably the duplex length is between 18 and 24 base pairs.

The antisense strand of the duplex has has significant levels of complementarity to both the sense strand and a target gene. By "significant levels of complementarity to both the sense strand and a target gene" is meant that the antisense strand possesses sufficient complementarity with the sense strand to allow a duplex to form, and also possesses sufficient complementarity with a target gene to allow RNA interference to occur following Dicer processing of the duplex oligonucleotide complex. The antisense strand preferably exhibits at least 60% complementarity to the sense strand and to the target gene, more preferably at least 70% complementarity, even more preferably at least 80% complementary. i.e. substantial complementarity. Higher and lower levels of complementarity are also contemplated. Note that the level of complementarity of the antisense strand to the sense strand does not need to be equal to the level of complementarity of the antisense strand to the target gene. Indeed, in the presence of the mismatches disclosed below the antisense strand may have a higher level of complementarity to the target gene than to the sense strand; however, it is also contemplated that in some embodiments the antisense strand has a higher level of complementarity to the sense strand than to the target gene.

In the case of siRNAs, the sequences of the sense and/or antisense strands of the duplex oligonucleotide can be selected by a variety of methods known to the art including random (non-rationally designed) selection based on the sequence of the gene and rational design methods (using any one of a number of art-recognized algorithms and/or neural networks) as long as the sequence can effectively silence a target gene. Detailed descriptions of the criteria for the rational design of siRNA antisense strands for efficient gene silencing can be found in WO 2004/045543, WO 2006/006948, WO 2005/078095, WO 2005/097992, and WO 2005/090606, each of which is incorporated herein by reference in its entirety. siRNAs of the disclosure can target any sequence including protein encoding sequences (e.g., open reading frames, ORFs), and non-coding sequences (e.g., 3' UTRs, 5' UTRs, intronic regions, promoter regions, microRNAs, piRNAs, enhancer regions, repetitive sequences, and more). In contrast, microRNA and piRNA mimics of the disclosure generally target a subset of genes and tools for predicting miRNA targets can be found in any number of publications including but not limited to Griffith-Jones, S. et al., Nucleic Acids Research, 2007, incorporated herein by reference in its entirety.

The duplex formed by the sense and the antisense strands can comprise at least one overhang, with each overhang comprising at least one nucleotide. By way of non-limiting example, overhang(s) can be located:

at the 5' end of the sense strand;
    at the 3' end of the sense strand;
    at the 5' and 3' end of the sense strand;
    at the 5' end of the antisense strand;
    at the 3' end of the antisense strand;
    at the 5' and 3' end of the antisense strand;
    at the 5' end of the sense strand and the 5' end of the antisense strand; or
    at the 3' end of the sense strand and the 3' end of the antisense strand In preferred embodiments, an overhang is present at the 3' end of the antisense strand. More preferably, the overhang on the 3' end of the antisense strand is a 2 nucleotide overhang. The selection of the bases for nucleotides in the overhang is made in an arbitrary manner i.e., the overhang nucleotides may or may not base pair with a target mRNA. Alternatively, the sequence of the overhang can be selected to pair with a particular target or can mimic (in the case of miRNA mimics) sequences that are flanking the mature miRNA sequence in the pri- or pre-miRNA. For convenience and simplicity, a 2 nucleotide overhang is usually a UU overhang (although AA, GG, CC, AC, CA, AG, GA, GC, and CG 2 nucleotide overhangs, and others, are also contemplated, see Vermeulen et al, (2005) RNA 11(5):674-682, incorporated herein by reference in its entirety). The nucleotides and/or the internucleotide linkages in the overhang may be modified with any of the nucleotide or internucleotide linkage modifications. Preferably, the internucleotide linkages in the overhang comprises phosphorothioate linkages. In one particularly preferred embodiment, the antisense strand comprises a 2 nucleotide UU overhang located at the 3' end of the antisense strand with a phosphorothioate linkage linking the 3' terminal U to the immediately 5' second U nucleotide, and with a phosphorothioate linkage linking the second U nucleotide to the next nucleotide (in the 5' direction) in the antisense strand.

The sense and antisense strands of the disclosure are comprised of RNA, DNA, RNA-DNA hybrids, and/or analogs of RNA and/or DNA such as locked nucleic acids, (LNAs), ethylene-bridged nucleic acids (ENAs), and more. In addition, a broad range of modifications, including chemically modified nucleotides, can be included in the sense and antisense strands to enhance stability, Dicer or RISC processing, functionality, and/or specificity. Modifications can also be used to minimize the innate immune response that cells typically have against dsRNAs (see Reynolds, A. et al (2006) RNA. 12(6):988-930). Such modifications can be added to the internucleotide linkage, the sugar backbone, and/or the base. A compatible list of modifications can be found in US Patent Application Publication No: 2005/0223427, WO2004/090105 and US Patent Application Publication No: US 2007/0269889, each of which is incorporated herein by reference in its entirety.

In one instance, the sense strand contains 2' carbon modifications, preferably 2'-O-alkyl modifications (such as 2'-O-methyl modifications) of some or all of the nucleotides. More preferably, the sense strand contains 2'-O-alkyl modifications of (1) nucleotides 1 and 2 (counting from the 5' end of the sense oligonucleotide but not including any 5' overhang which may be present), and (2) some or all of the Cs and Us, most preferably all of the Cs and Us. Preferable antisense strand modifications comprise 2' carbon modifications (including 2'-O-alkyl modifications such as 2'-O-methyl modifications), preferably 2' halogen modifications (e.g., 2' F modifications) on some or all of the nucleotides. More preferably, the antisense strand comprises 2' halogen modifications of some or all of the Cs and Us (more preferably on all of the Cs and Us), phosphorylation of the 5' end of the oligonucleotide, and stabilized internucleotide linkages (such as phosphorthioate linkages) associated with a 2 nucleotide 3' overhang. While these are the preferred set of modifications, alternatives that provide similar attributes can be incorporated into the design.

In addition, the sense and/or antisense strands can contain one or more conjugate moieties and/or labels that enhance delivery, functionality, or utility of the duplex. Conjugate moieties of the disclosure (also referred to simply as "conjugates") can vary widely and target entry into the cell by a variety of means. For instance, conjugate moieties can be lipid in nature and deliver their payload (e.g. siRNA or other nucleic acid), by inserting themselves into the membrane and being absorbed into the cell by one of several mechanisms including endocytosis. As such, lipid-based conjugate moieties can include cationic lipids, neutral lipids, sphingolipids, and fatty acids including stearic, oleic, elaidic, linoleic, linoleaidic, linolenic, and myristic acids. Alternatively, the conjugate moieties can be proteinaceous in nature including peptides that are membrane translocating (e.g. TAT, penetratin, MAP) or cationic (e.g. poly(lys), poly(arg), poly(his), poly (lys/arg/his), or protamine).

Alternatively, the conjugate moiety can be a small molecule that, for instance, targets a particular receptor or (again) is capable of inserting itself into the membrane or being absorbed by endocytic pathways. Thus, small molecules based on adamantanes, polyaromatic hydrocarbons (e.g. napthalenes, phenanthrenes, or pyrenes), macrocyles, steroids, or other chemical scaffolds, are all potential conjugates for the disclosure.

In yet another alternative, conjugate moieties can be based on cationic polymers. Numerous studies have demonstrated that cationic polymers such as cationic albumin can greatly enhance delivery to particular cell types and/or tissues (e.g. brain delivery, see Lu, W. et. al. (2005) J of Control Release 107:428-448). Given the benefits of these molecules, the conjugate moieties can be cationic polymers such as polyethyleneimine, dendrimers, poly(alkylpyridinium) salts, or cationic albumin.

In some cases, the conjugate moieties are ligands for receptors or can associate with molecules that (in turn) associate with receptors. Included in this class are bile acids, small molecule drug ligands, vitamins, aptamers, carbohydrates, peptides (including but not limited to hormones, proteins, protein fragments, antibodies or antibody fragments), viral proteins (e.g. capsids), toxins (e.g. bacterial toxins), and more. Also included are conjugates that are steroidal in nature e.g. cholesterol, cholestanol, cholanic acid, stigmasterol, pregnolone, progesterones, corticosterones, aldosterones, testosterones, estradiols, ergosterols, and more), Preferred conjugate moieties of the disclosure are cholesterol (CHOL), cholestanol (CHLN), cholanic acid (CHLA), stigmasterol (STIG), and ergosterol (ERGO). In certain preferred embodiments, the conjugate moiety is cholesterol.

In the case of cholesterol, the molecule can associate with one or more proteins or protein complexes in e.g. the blood (e.g. albumin, LDLs, HDLs, IDLs, VLDLs, chylomicron remnants, and chylomicrons) and be delivered to the cell through association with the appropriate receptor for that complex (e.g. the LDLR, low density lipoprotein receptor). The example of delivery via the cholesterol-LDL association is particularly attractive since the opportunity for dozens or hundreds of siRNA to be delivered in a single LDL particle is feasible. For that reason, the inventors can envision packaging cholesterol conjugated duplexes conjugated to derivatives of cholesterol, in one or more natural carriers (e.g. LDLs) in vitro, and using this as an in vivo delivery system.

In yet another embodiment, the molecules that target a particular receptor are modified to eliminate the possible loss of conjugated siRNAs to other sources. For instance, when cholesterol-conjugated siRNAs are placed in the presence of normal serum, a significant fraction of this material will associate with the albumin and/or other proteins in the serum, thus making the oligonucleotide duplex unavailable for e.g. interactions with LDLs. For this reason, the conjugate moieties of the disclosure can be modified in such a way that they continue to bind or associate with their intended target (e.g. LDLs) but have lesser affinities with unintended binding partners (e.g. serum albumin).

Preferably the conjugate moiety is attached to the sense and/or antisense strand using a linker. Though not wishing to be limited by definitions or conventions, in this application the length of the linker is described by counting the number atoms that represents the shortest distance between the atom that joins the conjugate moiety to the linker and the oxygen atom of the terminal phosphate moiety associated with the oligonucleotide through which the linker is attached to the oligonucleotide. For example, in embodiments where the conjugate moiety is joined to the linker via a carbamate linkage, the length of the linker is described as the number of atoms that represents the shortest distance between the nitrogen atom of the carbamate linkage and the oxygen atom of the phosphate linkage. In cases where ring structures are present, counting the atoms around the ring that represent the shortest path is preferred.

Linkers/linker chemistries that are based on ω-amino-1,3-diols, ω-amino-1,2-diols, hydroxyprolinols, ω-amino-alkanols, diethanolamines, ω-hydroxy-1,3-diols, ω-hydroxy-1,2-diols, ω-thio-1,3-diols, ω-thio-1,2-diols, ω-carboxy-1,3-diols, ω-carboxy-1,2-diols, ω-hydroxy-alkanols, ω-thio-alkanols, ω-carboxy-alkanols, functionalized oligoethylene glycols, allyl amine, acrylic acid, alyl alcohol, propargyl amine, propargyl alcohol, and more, can be applied in this context to generate linkers of the appropriate length.

In some embodiments a linker not only provides a site of attachment to the conjugate moiety, but also provides functional sites for attachment to the support and for initiation of oligonucleotide synthesis. Preferably, these sites are hydroxyl groups; most preferably, they are a primary hydroxyl group and a secondary hydroxyl group, to allow them to be chemically distinguished during synthesis of the conjugate-modified solid support. One hydroxyl group, preferably the primary hydroxyl group, is protected with a protecting group that can be removed as the first step in the synthesis of the oligonucleotide, according to methods well understood by those of ordinary skill in the art. Preferably, this protecting group is chromophoric and can be used to estimate the amount of the conjugate moiety attached to the solid support; most preferably, the group is chosen from triphenylmethyl (Tr), monomethoxytriphenylmethyl (MMTr), dimethoxytriphenylmethyl (DMTr) and trimethoxytriphenylmethyl (TMTr). Another hydroxyl group, preferably a secondary hydroxyl group, is derivatized with a functionalized tether that can covalently react with a functional group on the solid synthesis support, according to methods well understood by those of ordinary skill in the art. Preferable tethers are, by way of example, dicarboxylic acids such as succinic, glutaric, terephthalic, oxalic, diglycolic, and hydroquinone-O,O'-diacetic. One of the carboxylic acid functionalities of the tether is reacted with the hydroxyl to provide an ester linkage that is cleavable using basic reagents (hydroxide, carbonate or amines), while the other carboxylic acid functionality is reacted with the synthesis support, usually through formation of an amide bond with an amine functionality on the support.

The linker may also confer other desirable properties on the oligonucleotide conjugate: improved aqueous solubility, optimal distance of separation between the conjugate moiety and the oligonucleotide, flexibility (or lack thereof), specific orientation, branching, and others.

Preferably, the chemical bond between the linker and the conjugate moiety is a carbamate linkage; however, alternative chemistries are also within the scope of the disclosure. Examples of functional groups on linkers which form a chemical bond with a conjugate moiety include, but are not limited to, hydroxyl, amine, carboxylic acid, carboxylic acid halide, carboxylic acid active ester, carbonyl, chlorocarbonyl, imidazolylcarbonyl, thiol, maleimide, haloalkyl, sulfonyl, allyl and propargyl. Examples of chemical bonds that are formed between a linker and a cojugate include, but are not limited to, those based on carbamates, ethers, esters, amides, disulfides, thioethers, phosphodiesters, phosphorothioates, phorphorodithioate, sulfonamides, sulfonates, fulfones, sulfoxides, ureas, hydrazide, oxime, photolabile linkages, C—C bond forming groups such as Diels-Alder cyclo-addition pairs or ring-closing metathesis pairs, and Michael reaction pairs. In general, the conjugate moiety will have an appropriate functional group either naturally or chemically installed; the linker will then be synthesized with a functional group chosen to efficiently and stably react with the functional group on the conjugate moiety.

Linkers that have the same length, but are capable of associating with two or more conjugates, are also specifically contemplated.

In another embodiment, the linker may be a nucleoside derivative. The nucleoside may be, for example, a ribonucleoside, 2'-deoxyribonucleoside, or 2'-modified-2'-deoxyribonucleoside, such as 2'-O-methyl or 2'-fluoro. The nucleoside may be, for example, an arabinonucleoside or a 2'-modified arabinonucleoside. Using methods well known to those of ordinary skill in the art, purine and pyrimidine nucleosides may be modified at particular sites on the base to provide linkers and functional groups for attachment of conjugate moieties. For example, pyrimidine nucleosides, such as uridine and cytidine, may be modified at the 5-position of the uracil or cytosine base using mercuric acetate, a palladium catalyst, and an allylic reagent such as allylamine, allyl alcohol, or acrylic acid. Alternatively, 5-iodopyrimidines may be modified at the 5-position with a palladium catalyst and a propargylic reagent such as propargyl amine, propargyl alcohol or propargylic acid. Alternatively, uridine may be modified at the 4-position through activation with triazole or a sulfonyl chloride and subsequent reaction with a diamine, amino alcohol or amino acid. Cytidine may be similarly modified at the 4-position by treatment with bisulfite and subsequent reaction with a diamine, amino alcohol or amino acid. Purines may be likewise modified at the 7, 8 or 9 positions using similar types of reaction sequences.

In preferred embodiments, the linker is from about 3 to about 9 atoms in length. Thus, the linker may be 3, 4, 5, 6, 7, 8, or 9 atoms in length. Preferably, the linker is 5, 6, 7, or 8 atoms in length. More preferably, the linker is 5 or 8 atoms in length. Most preferably the linker is a straight chain C5 linker i.e., there are 5 carbon atoms between the atom that joins the conjugate moiety to the linker and the oxygen atom of the terminal phosphate moiety associated with the oligonucleotide through which the linker is attached to the oligonucleotide. Thus, where the conjugate moiety is joined to a C5 linker via a carbamate linkage, there are 5 carbon atoms between the nitrogen atom of the carbamate linkage and the oxygen atom of the phosphate linkage.

In one preferred embodiment, the conjugate moiety is cholesterol and the linker is a C5 linker (a 5 atom linker) attached to the cholesterol via a carbamate group, thus forming a Chol-05 conjugate-linker (e.g. cholesteryl 5-(bis(4-methoxyphenyl)(phenyl)methoxy)-3 hydroxypentylcarbamate)). When attached via a phosphodiester linkage to the 5' and/or 3' terminus of a sense and/or antisense oligonucleotide of a duplex, the resulting conjugate-linker-oligonucleotide can have the structure:

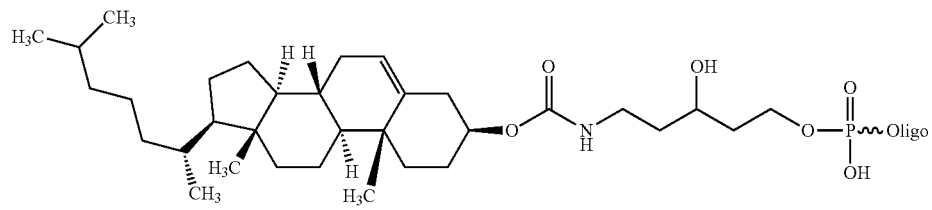

In another preferred embodiment, the conjugate moiety is cholesterol and the linker is a C3 linker attached to the cholesterol via a carbamate group, thus forming a Chol-C3 conjugate-linker. When attached via a phosphodiester linkage to the 5' and/or 3' terminus of a sense and/or antisense oligonucleotide, the resulting conjugate-linker-oligonucleotide can have the structure:

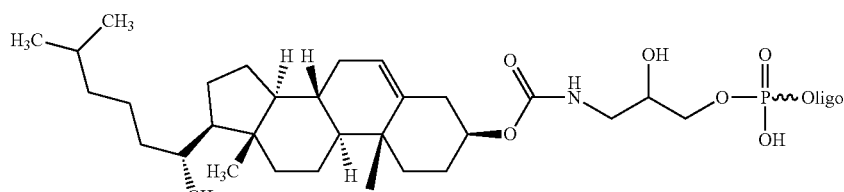

In another preferred embodiment, the conjugate moiety is cholesterol and the linker is a C8 linker (a 8 atom linker) attached to the cholesterol via a carbamate group, thus forming a Chol-C8 conjugate-linker. When attached via a phosphodiester linkage to the 5' and/or 3' terminus of a sense and/or antisense oligonucleotide, the resulting conjugate-linker-oligonucleotide can have the structure:

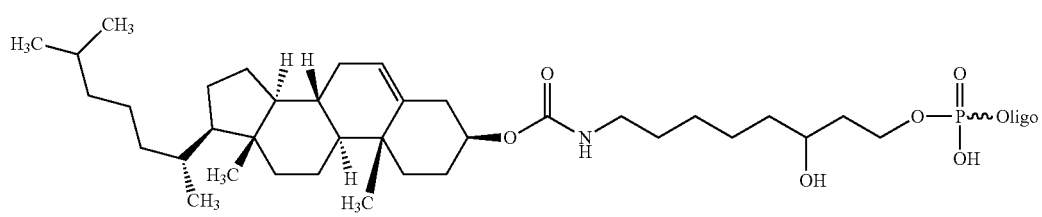

In another preferred embodiment, the conjugate moiety is cholesterol and the linker is a PRO linker (a 4 atom linker) attached to the cholesterol via a carbamate group, thus forming a Chol-PRO conjugate-linker. When attached via a phosphodiester linkage to the 5' and/or 3' terminus of a sense and/or antisense oligonucleotide, the resulting conjugate-linker-oligonucleotide can have the structure:

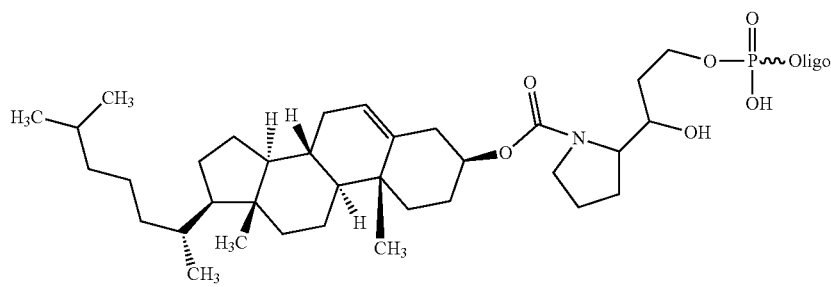

In another preferred embodiment, the conjugate moiety is cholesterol and the linker is a PIP linker (a 6 atom linker) attached to the cholesterol via a carbamate group, thus forming a Chol-PIP conjugate-linker. When attached via a phosphodiester linkage to the 5' and/or 3' terminus of a sense and/or antisense oligonucleotide, the resulting conjugate-linker-oligonucleotide can have the structure:

In another preferred embodiment, the conjugate moiety is cholesterol and the linker is a C6-HP (also referred to as "HP6") linker (a 9 atom linker) attached to the cholesterol via a carbamate group, thus forming a Chol-C6-HP conjugate-linker. When attached via a phosphodiester linkage to the 5' and/or 3' terminus of a sense and/or antisense oligonucleotide, the resulting conjugate-linker-oligonucleotide can have the structure:

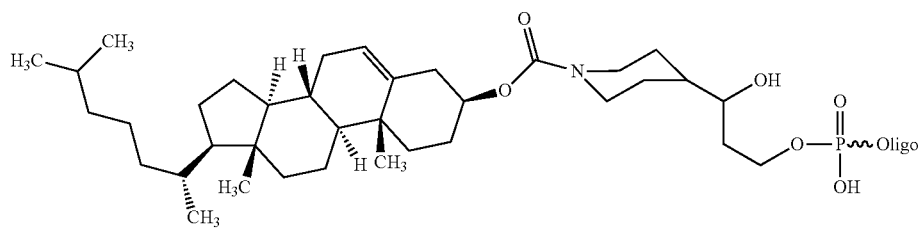

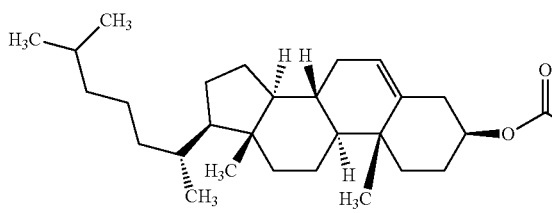 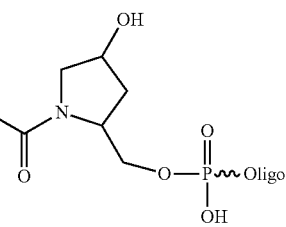

It is explicitly contemplated that the C5, C3, C8, PRO, C6-HP and PIP linkers in the foregoing embodiments can be used with conjugate moieties other than cholesterol, including, for example, cholestanol (CHLN), cholanic acid (CHLA), stigmasterol (STIG), and ergosterol (ERGO). It will also be understood that while the C5, C3, C8, PRO, C6-HP, and PIP linkers exemplified above are shown with a carbamate group attaching the conjugate to the linker, other attachment chemistries may be used (see below). Finally, while the C5, C3, C8, PRO, C6-HP, and PIP linkers in the foregoing embodiments are shown attached to oligonucleotides via a phosphodiester linkage, it will be appreciated that other sites of attachment to oligonucleotides, and other chemistries for attachment to oligonucleotides, may be used (see below).

In some embodiments, the duplex oligonucleotide complex also includes a detectable label, such as a dye molecule or a radiolabel. Suitable dye molecules include, but are not limited to, fluorescent dye molecules and phosphorescent dye molecules. Suitable fluorescent dyes include TAMRA, BODIPY, Cyanine derivatives such as Cy3 or Cy5 Dabsyl, fluoroscein, or any other suitable fluorophore known in the art. A detectable label may be attached at any position in the duplex oligonucleotide complex, preferably at the 5' or 3' end of one or more of the strands. Most preferably, the detectable label is a fluorescent dye molecule which is attached to the 5' end of the sense strand. The detectable label may be attached using any method known in the art. In addition, the detectable label may be attached using any of the aforementioned linkers. The use of dye molecules allows one skilled in the art to monitor the transfection efficiency of the duplex oligonucleotide complexes.

The position of the conjugate-linker on the duplex oligonucleotide complex can vary with respect to the strand or strands that are conjugated (e.g. the sense strand, the antisense strand, or both the sense and antisense strands), the position or positions within the strand that are modified (i.e. the nucleotide positions within the strand or strands), and the position on the nucleotide(s) that are modified (e.g. the sugar, the base). Conjugate-linkers can be placed on the 5' and/or 3' terminus of one or more of the strands of the disclosure. For example, a conjugate-linker can be placed on the 5' end of the sense strand and/or the 3' end of the sense strand and/or the 5' end of the antisense strand and/or the 3' end of the antisense strand. A conjugate-linker can be attached the 5' and/or 3' end of a strand via a phosphodiester bond. In preferred embodiments, a conjugate-linker is attached to the one or both ends of the sense strand via a phosphodiester bond, more preferably to the 3' end of the sense strand.

A conjugate-linker can also be attached to internal positions of the sense strand and/or antisense strand. In addition, multiple positions on the nucleotides including the 5-position of uridine, 5-position of cytidine, 4-position of cytidine, 7-position of guanosine, 7-position of adenosine, 8-position of guanosine, 8-position of adenosine, 6-position of adenosine, 2'-position of ribose, 5'-position of ribose, 3'-position of ribose, can be employed for attachment of the conjugate to the nucleic acid.

A list of additional potential conjugates, linkers, and labels, and the positions at which they can be attached is described in U.S. patent application Ser. No. 11/858,829, published as United States Patent Application Publication No: 2008/00085869, incorporated herein by reference in its entirety.

Mismatches

The inventors have now discovered that chemical modifications added to the sense strand can, in some cases, have a negative effect on duplexes entering the RNAi pathway (either as siRNAs, piRNA mimics, or miRNA mimics). The present application discloses that the introduction of one or more mismatches at distinct positions within the duplex oligonucleotide is capable of minimizing these negative effects. Specifically, the present disclosure teaches that a sense strand that is chemically modified and contains at least one mismatch with the antisense strand at certain unique positions has minimal ability to inhibit the action of the antisense strand, thus eliminating the negative effects associated with incorporating the chemical modifications.

More specifically, in embodiments where the antisense strand of the siRNA or miRNA mimic is 19 nucleotides in length (not counting any overhang(s)) mismatches can be introduced into the sense strand so that antisense nucleotides A) 1 and/or 2, B) 6, 7 and/or 8, and/or C) 13 and/or 14 (counting from the 5' end of the antisense strand of the molecule and, again, not counting any overhang which may be present at the 5' end) do not form a Watson-Crick basepair with the opposing nucleotide on the sense strand. That is, the mismatch is between the specified antisense strand nucleotide position and the opposite nucleotide on the sense strand. The mismatches can be introduced singly or in any combination, for example, 1, 1 plus 7, or 1 plus 7 plus 14. All of the mismatches result from nucleotide changes in the sense strand and therefore do not alter the properties of the antisense strand binding to the target. Most preferably, the mismatches are found between the nucleotide at positions 1, and/or 7, and/or 14 of the antisense strand and the opposite nucleotide on the sense strand.

It will be understood by the skilled person that while the position of the mismatches have been described with reference to the antisense strand, mismatch positions can also be described with reference to the sense strand, counting from the 5' end of that oligonucleotide (and not including any overhangs that may be present). In the case of a 19 base pair duplex, position 14 of the antisense strand is opposite position 6 of the sense strand; position 13 of the antisense strand is opposite position 7 of the sense strand; position 8 of the antisense strand is opposite position 12 of the sense strand; position 7 of the antisense strand is opposite position 13 of the sense strand; position 6 of the antisense strand is opposite position 14 of the sense strand; position 2 of the antisense strand is opposite position 18 of the sense strand; and position 1 of the antisense strand is opposite position 19 of the sense strand. Thus, a change in the nucleotide at position 7 of the sense strand results in a mismatch with position 13 of the antisense strand. A change in the nucleotide at position 12 of the sense strand results in a mismatch with position 8 of the antisense strand. A change in the nucleotide at position 13 of the sense strand results in a mismatch with position 7 of the antisense strand. A change in the nucleotide at position 14 of the sense strand results in a mismatch with position 6 of the antisense strand. And a change in the nucleotide at position 19 of the sense strand results in a mismatch with position 1 of the antisense strand. See FIG. 1B.

The described base pair mismatches are between the sense strand and the antisense strand of the targeting duplex (siRNA, miRNA, piRNA) and result from changes in the sequence of the sense strand. In this way, the alteration does not affect the ability of the antisense strand (also referred to as the targeting strand) to anneal to the target sequence. Mismatches can occur in a variety of forms. For instance for A-U base pairing, A-A, A-C, A-G, U-U, U-C, and U-G mismatches are all acceptable. Similarly for G-C pairings, G-G, G-A, C-C, C-U, and C-A mismatches are also acceptable.

Figure 1B:
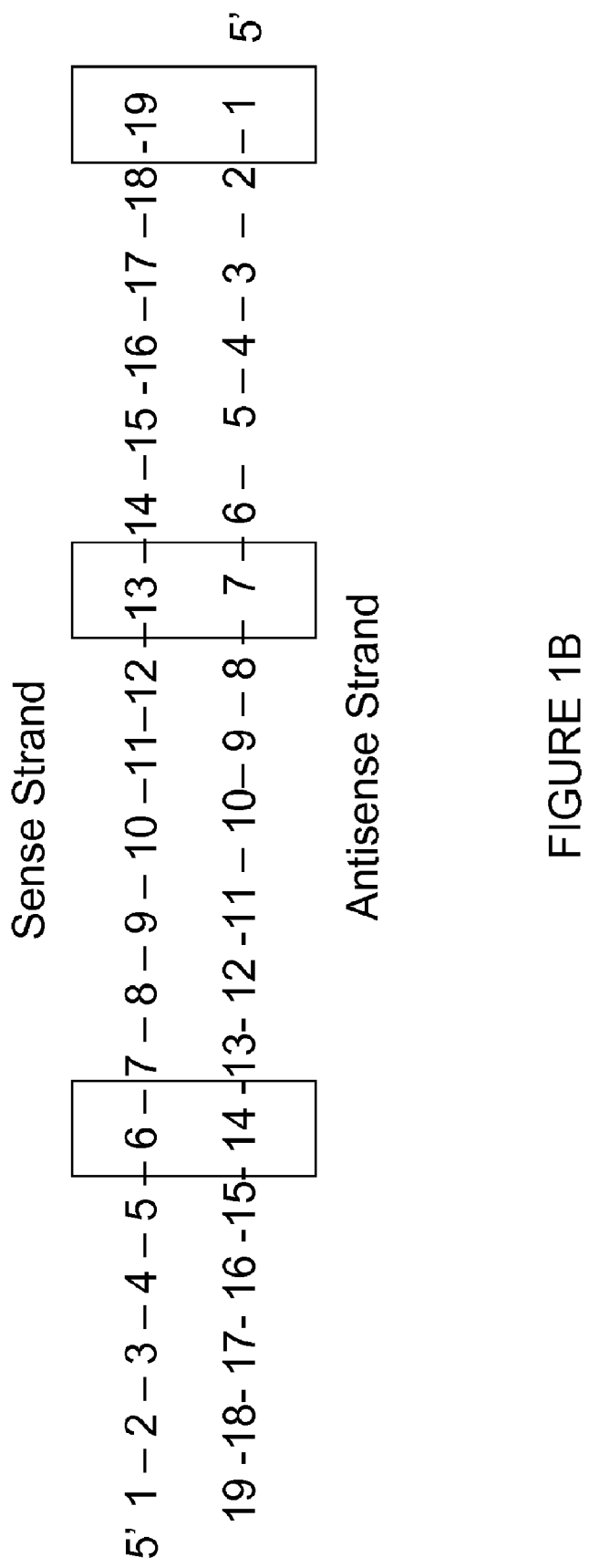
FIG. 1B provides a numerical representation showing preferred positions of mismatches in a miRNA mimic. Boxes show the position of mismatches and include (1) mismatch between position 6 of the sense strand and position 14 of the antisense strand (also referred to as mature strand), (2) mismatch between position 13 of the sense strand and position 7 of the antisense strand, and (3) mismatch between position 19 of the sense strand and position 1 of the antisense strand.

A schematic diagram of one preferred design of the disclosure is shown in FIG. 1A. In this non-limiting example, which depicts a siRNA molecule, the sense strand is 1) 19 nucleotides in length, 2) contains 2'-O-methyl modifications at positions 1 and 2 (counting from the 5' terminus of the molecule; see black circles), 3) contains 2'-O-methyl modifications of some or all of the Cs and Us (white circles), 4) contains a C5 linker on the 3' terminus of the oligonucleotide, and 5) has a cholesterol conjugate (Ch1) associated with the distal end of the linker which allows the duplex to be introduced into cells with employing transfection agents. In this embodiment, the C5 linker and the Ch1 conjugate have the following structure (where "Oligo" represents the sense strand):

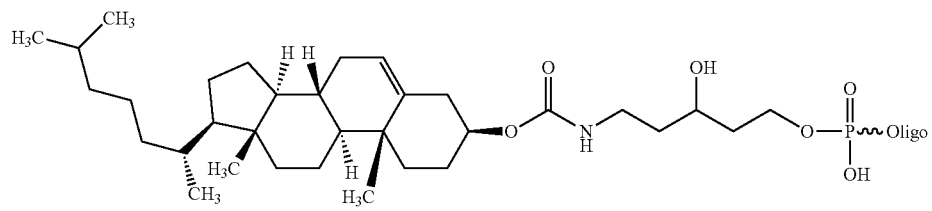

The antisense (mature) strand in the preferred siRNA design of FIG. 1A is similarly 19 nucleotides in length (not including the overhang), contains a 5' phosphate group (P04), has 2' F groups on some or all Cs and Us (striped circles), and has a 2 nucleotide 3' overhang (A-G) with stabilized phosphorothioate internucleotide linkages (*). In addition, mismatches (dashed lines) have been introduced into the duplex by modifying the sequence of the sense strand at sense strand positions 6, 13, and 19 so that the specified sense strand nucleotides do not base pair with the opposite nucleotides on the antisense strand namely positions 14, 7, and 1 respectively.

Duplexes that are longer than 19 base pairs have additional nucleotides added to the 5' end and 3' end of the sense and antisense strands, respectively (see FIG. 1C). As such, the positions of the mismatches with respect to the 5' end of the antisense strand remain the same. We prefer to refer to mismatch positions by disclosing the nucleotide positions on the antisense strand (starting from the 5' end, and not including overhangs) that are mismatched with the opposite nucleotide position on the sense strand. Thus, mismatches between antisense nucleotides 1 and/or 7 and/or 14 and the opposite nucleotide position on the sense strand are specifically contemplated. It is understood that such mismatches are created by changing the sense strand nucleotide position that is opposite, for example, nucleotide 1, 7, or 14 of the antisense strand.

WIPO application PCT/US2007/079051, published as WO/2008/036825 and incorporated herein by reference in its entirety, provides additional duplex oligonucleotide complexes (including the "G4" complex) having a variety of linkers and conjugates to facilitate intracellular delivery. The mismatch positions identified in the instant disclosure may be used with any of the complexes of PCT/US2007/079051.

Although FIG. 1 depicts siRNA-based embodiments of the disclosure, it is to be understood that the disclosure is not limited to providing siRNA molecules. As described above and in the Examples below, piRNA mimics and miRNA mimics having the features disclosed above, including the modified nucleotides, the specific mismatches, and the conjugate-linker, are also provided by the disclosure.

Utility

The mismatch-containing duplexes of the disclosure may be employed in methods related to RNAi. As stated previously, methods related to RNAi include, but are not limited to targeting a gene or genes with siRNA, shRNA, miRNAs, or piRNAs. In addition, the targeting of miRNAs, siRNAs, shRNAs, or piRNAs with inhibitors are included as methods related to RNAi.

The mismatch-containing duplexes of the disclosure are particularly potent in silencing genes by the RNAi pathway. Mismatch-containing duplexes of the disclosure (including siRNA, piRNA mimics, and miRNA mimics) which comprise cholesterol (CHOL), cholestanol (CHLN), cholanic acid (CHLA), stigmasterol (STIG), or ergosterol (ERGO) as a conjugate, especially when linked to the 3' end of a sense strand via a C5 linker (such as the siRNA depicted in FIG. 1), are particularly useful because they can be used to passively deliver (i.e., deliver without additional transfection reagents) their attached duplex oligonucleotide to cells in culture or other environments in order to silence or knockdown genes. In some embodiments, such molecules are passively delivered to cells in culture (e.g., in culture plates, culture dishes, multiwell plates etc without limitation). The molecules may be delivered to cells in culture under a range of serum conditions, including but not limited to culture media having 10-20% serum, as well as culture media having reduced serum levels, for example, less than 10% serum or less than 5% serum, or less than 1% serum. The use of serum free media and media having modified serum is also contemplated. In one embodiment, cells are cultured in standard, art-tested reduced-serum media that are commercially available from numerous companies including Invitrogen, and HyClone. For example, cells are first plated in serum medium, then the serum medium is replaced with reduced serum medium comprising a mismatch-containing duplex of the disclosure for 24 hours, then the reduced serum medium is replaced with serum medium.

Mismatch-containing duplexes that comprise cholesterol linked to the 3' end of a sense strand via a C5 linker (such as the siRNA depicted in FIG. 1A), may be conveniently supplied to end-users premixed in reduced serum media (including serum-free media). Such duplex molecules can be stored in such media at 4° C. for extended periods of time without significant loss of gene silencing activity. Thus, in one aspect, the disclosure provides a kit comprising one or more containers, each container comprising reduced serum media and a mismatch-containing duplex(es) of the disclosure. The kit may also comprise instructions that instruct one skilled in the art how to passively-deliver the duplex to cells in accordance with the teachings of the disclosure. In this way, the mismatch-containing duplexes of the disclosure may be purchased by a consumer in a stable and ready-to-use formulation. Gene silencing may then be carried out by simply culturing cells in the supplied formulation without additional transfection steps. In addition, if the supplied formulation comprises a plurality of mismatch-containing duplexes (e.g., siRNAs), each specific for a particular gene, then a single supplied formulation may be used for the simultaneous silencing of a plurality of genes. If a single gene is to be silenced, then the supplied formulation may comprise a single duplex of the disclosure, or it may comprise a pool of duplexes, each targeting a different region of, for example, a single target mRNA of interest.

In another embodiment, mismatch-containing duplex molecules that comprise cholesterol linked to the 3' end of a sense strand via a C5 linker (such as the siRNA depicted in FIG. 1A) are used to silence genes in cultured cells in a "reverse transfection" format. In this format, the duplexes of the disclosure are first dispensed onto a solid support (such as a glass slide) and then cells are grown on the solid support. Cells that grow on the solid support take up the duplex through passive delivery. In preferred embodiments, a plurality of different duplexes are attached at a plurality of spatially defined addresses on a solid support (for example, by printing or pipetting spots of the duplexes on the support), thus forming a microarray of the duplexes e.g. a microarray of siRNAs and/or miRNA mimics and/or piRNA mimics. Cells that are grown on the solid support thereby come into contact with different duplex oligonucleotide complexes in a position-dependent manner. The support can be modified or can be unmodified (e.g., with one or more polymers) that enhance retention or delivery of the duplex, or enhance adhesion of the cell population to the solid support.

Mismatch-containing duplexes of the disclosure which comprise cholesterol (CHOL), cholestanol (CHLN), cholanic acid (CHLA), stigmasterol (STIG), or ergosterol (ERGO) as a conjugate, especially when linked to the 3' end of a sense strand via a C5 linker (such as the siRNA of FIG. 1), are also particularly useful for continuous dosing of cells. Continuous dosing with the duplexes of the disclosure is useful for achieving long term knockdown of a gene target. Moreover, cells continuously dosed with the duplexes of the disclosure remain amenable to conventional lipid-mediated transfection. Thus, it is possible to use the duplexes of the disclosure to knockdown a specific gene and then to use conventional lipid-mediated delivery of additional reagents that mediate RNAi (e.g., additional siRNAs) in order simultaneously to knockdown additional genes. In this way, it is possible to screen a panel of different siRNAs for a phenotype of interest in a "background" of a continuous knockdown of one specific gene.

In one embodiment, the compositions of the disclosure are used in basic research settings, in drug discovery settings, in ADME-tox applications, and in therapeutic/prophylactic applications.

In yet another embodiment, a method by which different combinations of linkers, conjugates, and delivery payloads are combined to screen for functional arrangement is described.

In yet another embodiment, a combi-chem approach to screen for conjugate structures that enhance nucleic acid delivery, preferably delivery of siRNAs, miRNAs, miRNA mimics, piRNAs, miRNA and piRNA inhibitors, is described.

In yet another embodiment, one or more compositions of the disclosure are used to perform small molecule screening.

In yet another embodiment, one or more compositions and/or methods of the disclosure are used to identify molecules that are capable of blocking the interaction of the molecules of the disclosure with another entity, such as a serum protein.

In yet another embodiment, one or more compositions and/or methods of the disclosure are used to optimize the backbone for universal attachment of ligands.

In yet another embodiment, one or more compositions of the disclosure are used in kits developed for transfection procedures. Such procedures can include 1) plating cells in e.g. a well and adding one or more compositions of the disclosure to the well for passive delivery or 2) depositing one or more compositions of the disclosure in a well or on a slide and adding cells to initiate passive delivery of the molecules of the disclosure. In both cases, such methods can be employed to introduce a homogeneous population of molecules into cells, or can be arrayed in such a way as to introduce larger collections (e.g. a genome wide collection of siRNA, miRNA mimics, or piRNA mimics) into cells.

In another embodiment, the compositions of the disclosure are applied in high throughput screening methods.

In yet another embodiment, the compositions of the disclosure are employed to introduce nucleic acids e.g. siRNA into hard-to-transfect cells such as Jurkat cells, stem cells, cells of neuronal origin, and cells of a myeloid origin.

In another embodiment, the compositions of the disclosure are employed to introduce nucleic acids, e.g. siRNA into primary cells.

In another embodiment, the compositions of the disclosure are employed to introduce nucleic acids, e.g. siRNA into non-adherent, suspension cells.

In another embodiment, the compositions of the disclosure are employed to deliver a wide array of nucleic acids including but not limited to siRNA, miRNAs, miRNA mimics and inhibitors, piRNAs, piRNA inhibitors, plasmids, antisense molecules, modified and unmodified nucleic acids, hybrid nucleic acids (e.g. DNA-RNA hybrids), and more. Importantly, the present disclosure can be used to deliver miRNAs, siRNAs, and piRNAs of the human genome implicated in diseases such as diabetes, Alzheimer's, and cancer, as well as those associated with the genomes of pathogens (e.g. pathogenic viruses), or host-encoded genes that play a role in pathogen entry, replication, packaging, release, or any other critical step in pathogen replication.

In another embodiment, the compositions of the disclosure are used to deliver collections of nucleic acids such as pools of siRNA targeting multiple sites on a single gene, pools of siRNA targeting multiple genes, pools of miRNA or piRNA mimics, pools of miRNA or piRNA inhibitors, and more. Alternatively, pools of miRNA mimics or miRNA inhibitors, particularly those that are related to a particular disease, can be simultaneously delivered using the compositions of the disclosure.

In another embodiment, the compositions of the disclosure are used to deliver one or more randomly selected nucleic acids e.g. siRNA.

In another embodiment, the compositions of the disclosure are used to deliver one or more nucleic acids that have been selected by rational design methods.

In another embodiment, the compositions of the disclosure are control molecules that, for instance, are incapable of entering RISC, or can cause toxicity, or are labeled and can be used to assess transfection efficiency.

In another embodiment, the compositions of the disclosure are used to deliver molecules that target a specific gene or set of genes for RNAi. For instance, the set of genes might include a set of siRNA that target e.g. the kinome, or GPCRs, or genes associated with membrane remodelling, or the druggable genome set, or an entire genome.

In another embodiment, the compositions of the disclosure and related methods are used for diagnostic applications, prophylactics, therapeutics, agricultural applications, veterinary applications, research tools, cosmetic applications, and more. In the case of therapeutics and prophylactics, the compositions of the disclosure can be used in the manufacture of a medicament in animals, preferably mammals, more preferably humans in the treatment of diseases. Dosages of medicaments manufactured in accordance with the present disclosure may vary from micrograms per kilogram to hundreds of milligrams per kilogram of a subject. As is known in the art, dosage will vary according to the mass of the mammal receiving the dose, the nature of the mammal receiving the dose, the severity of the disease or disorder, and the stability of the medicament in the serum of the subject, among other factors well known to persons of ordinary skill in the art. For these applications, an organism suspected of having a disease or disorder that is amenable to modulation by manipulation of a particular target nucleic acid of interest is treated by administering compositions of the disclosure. Results of the treatment may be ameliorative, palliative, prophylactic, and/or diagnostic of a particular disease or disorder.

Furthermore, in the case of therapeutic or prophylactic applications, the compositions of the disclosure can be combined with a variety of therapeutic compositions, delivery agents, and methods of administration. Pharmaceutically acceptable carriers, excipients, and diluents are known to persons skilled in the art. Methods of administration to cells and organisms are also known to persons skilled in the art. Dosing regimens, for example, are known to depend on the severity and degree of responsiveness of the disease or disorder to be treated, with a course of treatment spanning from days to months, or until the desired effect on the disorder or disease state is achieved. Chronic administration of molecules of the disclosure may be required for lasting desired effects with some diseases or disorders. Suitable dosing regimens can be determined by, for example, administering varying amounts of one or more molecules of the disclosure in a pharmaceutically acceptable carrier or diluent, by a pharmaceutically acceptable delivery route, and amount of drug accumulated in the body of the recipient organism can be determined at various times following administration. Similarly, the desired effect can be measured at various times following administration of the molecule(s) of the disclosure, and this data can be correlated with other pharmacokinetic data, such as body or organ accumulation. Those of ordinary skill can determine optimum dosages, dosing regimens, and the like. Those of ordinary skill may employ $EC_{50}$ data from in vivo and in vitro animal models as guides for human studies.

In another embodiment, the compositions and methods of the disclosure are used in combinational therapies, in particular, combinational therapies directed toward alleviating or minimizing the effects of human diseases including cancer, Alzheimer's and other neural diseases such as epilepsy, and more.

In another embodiment, the compositions and methods of the disclosure are employed in structure/function studies to design and test alternative targeting scaffolds.

In another embodiment, the compositions of the present disclosure are used to deliver nucleic acids to a broad range of organisms, including but not limited to plants, animals, protozoa, bacteria, viruses and fungi. The present disclosure is particularly advantageous for use in mammals such as cattle, horse, goats, pigs, sheep, canines, rodents such as hamsters, mice, and rats, and primates such as, gorillas, bush babies, chimpanzees, and humans.

In another embodiment, the compositions and methods of the disclosure can be used to target specific tissues, particularly diseased tissues including heart tissues, neural tissues, tissues of the gastrointestinal tract, muscle tissues, pulmonary tissues, cancerous tissues, tissues infected with pathogens, and more. The present disclosure may be used advantageously with diverse cell types, including but not limited to primary cells, germ cell lines and somatic cells. For example, the cell types may be embryonic cells, oocytes, sperm cells, adipocytes, fibroblasts, myocytes, cardiomyocytes, endothelium, neurons, glia, blood cells, megakaryocytes, lymphocytes, macrophages, neutrophils, eosinophils, basophils, mast cells, leukocytes, granulocytes, keratinocytes, chondrocytes, osteoblasts, osteoclasts, hepatocytes and cells of the endocrine or exocrine glands.

In another embodiment, the compositions of the disclosure are delivered to e.g. a subject by intravenous, inhalation, intramuscular, dermal, sub-dermal, cutaneous, subcutaneous, intranasal, oral, rectal, by eye drops, by tissue implantation of a device that releases the molecule(s) at an advantageous location, such as near an organ or tissue or cell type harboring e.g. a target nucleic acid of interest, or other art recognized methods for introducing nucleic acids to a subject. The molecules of the disclosure can be administered in a cream or ointment topically, an oral preparation such as a capsule or tablet or suspension or solution, and the like.

EXAMPLES SECTION

The following non-limiting examples are provided solely to aid in the understanding of the disclosure.

Example 1

Identification of miRNA Inhibitory Activity Associated with the Sense Strand of miRNA Mimics Our previous studies have demonstrated that chemical modifications can stabilize nucleic acids. In particular, 2'-O methyl modification of some or all of the nucleotides in a strand can stabilize that molecule against endonuclease degradation and greatly enhance the functionality of the molecule. While addition of 2'-O-methyl modifications to the sense strand of a double stranded miRNA mimic can enhance the stability (and therefore the functionality) of the molecule, it was suspected that a stabilized sense strand might also be acting as a miRNA inhibitor, thereby limiting the function of miRNA mimics. To test the whether the 2'-O-methyl modified sense strand of a mimic molecule could also act as an inhibitor, the following materials were first generated.

miRNA Mimics: miR-141 and miR-122 were synthesized using standard 2'-O-ACE chemistry. These molecules all contained the following modifications: the sense strand contains 2'-O-methyl modifications of (1) nucleotides 1 and 2 (counting from the 5' end of the sense oligonucleotide), and (2) all of the Cs and Us. In addition, a cholesterol conjugate is linked to the 3' end of the sense oligonucleotide using a C5 linker described previously (U.S. patent application Ser. No. 11/858,829, published as United States Patent Application Publication No: 2008/0085869, incorporated herein by reference in its entirety). The antisense strand modifications comprise: 2' F modifications all of the Cs and Us and phosphorylation of the 5' end of the oligonucleotide. In addition, a two nucleotide 3' overhang, having stabilized internucleotide linkages, is also associated with the antisense strand. This modification pattern is referred to herein as "the G4 modification pattern"; in this disclosure, oligonucleotides modified in this way contain the signifier "G4" in their annotation. Sense and antisense strand sequences are provided in Table 1.

TABLE 1

| miR | Antisense strand Sequence | Sense Strand Sequence |
|---|---|---|
| 122 | 5'-UGGAGUGUGACAAUGGUG U*U*U (SEQ ID NO: 1) | 5'-ACACCAUUGUCACACUCCA (SEQ ID NO: 2) |
| 141 | 5'-UAACACUGUCUGGUAAAG A*U*U (SEQ ID NO: 3) | 5'-UCUUUACCAGACAGUGUUA (SEQ ID NO: 4) |

Modified Sense Strands: In addition to synthesizing each of the mimics, each sense strand was synthesized individually with the exact modifications incorporated into the mimic.

Reporter Constructs: The dual-luciferase plasmid, psiCHECK™-2 Vector, containing both the synthetic firefly luciferase gene (hfluc+) and the synthetic *Renilla* luciferase gene (hRluc), each with its own promoter and poly(A)-addition sites, was obtained from Promega (Cat.# C8021). miRNA target sequences were inserted between the XhoI-Not I restriction sites in the multiple cloning region in the 3' UTR of the hRluc gene using standard molecular biological techniques. Target sites are reverse complements of their respective predicted mature miRNAs (Sanger Institute miR-Base::Sequences, http://microrna.sanger.ac.uk).

To assess the effects of modified sense strands on miRNA function, the ratio of hRluc to hfluc activity by the appropriate dual luciferase reporter construct was determined in the presence of (1) the miRNA mimic, or (2) the sense strand alone. To achieve this, the following experiment was performed:
1. On the first day, 10,000 MCF-7 or Huh7 cells were plated in complete media (DMEM+10% fetal calf serum, FCS) in each well of a 96 well plate.
2. On day 2 the complete media (containing fetal calf serum) was replaced with serum deficient media (RS media) containing the modified miR-122 (for Huh-7 cells) or miR-141 (for MCF-7 cells) mimics or the modified sense strand of miR-122 or miR-141 (0-1 ug/ml). Cells were "passively" transfected for 24 hours,
3. On day 3 the reporter construct for miR-122, miR-141, or the psiCHECK-2 control reporter was transfected into the same MCF-7 cells using DharmaFECTduo (0.2 ug per well) according to manufacturer's instructions
4. Two days after transfection of the reporter, the ratio of *Renilla* to firefly luciferase was measured under each test condition and compared with cells that had been transfected with the psiCheck reporter alone.

Figure 2A:
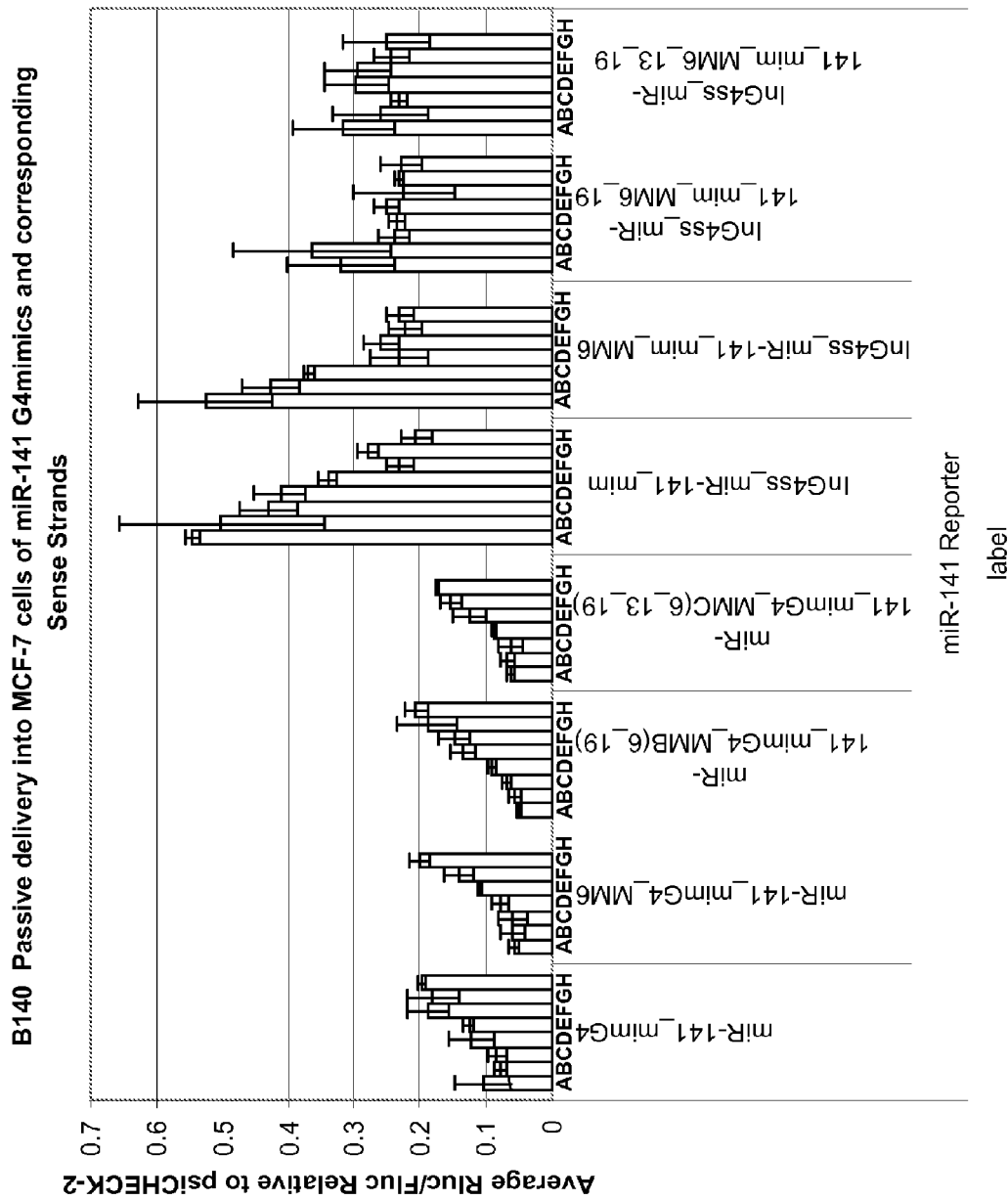
FIG. 2A graphically demonstrates the effects of miR-141 mimics and sense strands on the ratio of *Renilla* luciferase to firefly luciferase in MCF-7 cells. The experimental protocol used in these studies requires that cells passively transfected with mimics are subsequently transfected with reporter constructs using lipid delivery reagents. In cells transfected with miRNA mimics (e.g. miR-141_mim G4) the Rluc/fluc ratio is low (0.1-0.3 at all concentrations) demonstrating that the mimic is silencing the reporter. Transfection of cells with the modified sense strand of miR 141 repress the ability of endogenous miR-141 to silence the reporter construct (see lnG4 ss_miR141_mim), demonstrating that the sense strand with this modification pattern can act as an inhibitor.
Figure 2B:
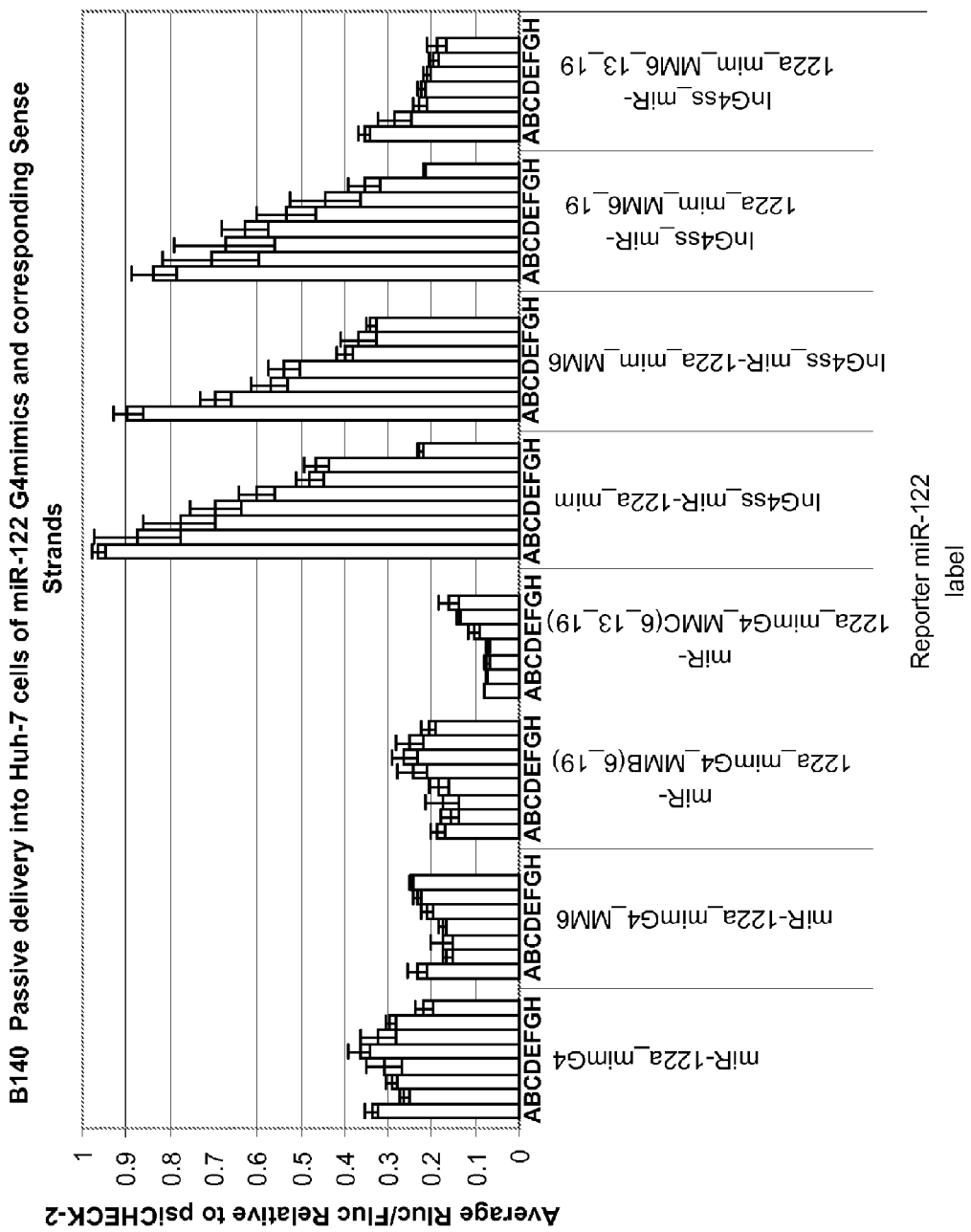
FIG. 2B graphically demonstrates the effects of transfecting miR-122 mimics and sense strands on the ratio of *Renilla* luciferase to firefly luciferase in Huh-7 cells. Cells passively transfected with miRNA-122 mimics (e.g. miR-122_mim G4) exhibit a low Rluc/fluc ratio low (0.1-0.3 at all concentrations). As was observed with miR-141 in MCF-7 cells, transfection of Huh-7 cells with the modified sense strand of miR-122 repressed the ability of endogenous miR-122 to silence the reporter construct (see lnG4 ss_miR141_mim). These findings (again) demonstrate the negative effects that modified sense strands can have on overall miRNA mimic or siRNA activity.

Results of these experiments are presented in FIGS. 2A and 2B and demonstrate the negative effects of having 2'-O-methyl modified sense strands in miRNA mimic design. In FIGS. 2A-2B, the letters A-E under each column of the bar graph indicate the mimic concentration, with A=1 uM; B=0.5 uM, C=0.25 uM, D=0.13 uM, E=0.06 uM, F=0.03 uM, G=0.02 uM, and H=0 uM. In cells transfected with the reporter constructs alone (see miR-141 mim_G4 and miR-122a mim_G4, 0 nM) reporter expression is low due to the relatively high expression of endogenous miR-141 and miR-122a in MCF-7 and Huh-7, respectively. Under these conditions, further addition of mimics has only minor effects on reporter expression (Rluc/Fluc ratios of 0.1-0.3 at all concentrations of mimics). Addition of the modified sense strand of miR 141 at concentrations as low as 0.06 uM repressed the ability of endogenous miR-141 to silence hRluc reporter in MCF-7 cells (see lnG4 ss_miR141_min, FIG. 2A). Similarly, low concentrations of the modified sense strand of miR-122 greatly enhanced hRluc reporter expression (i.e., repressed endogenous miR-122 function) in Huh7 (see lnG4ss_miR122-min in FIG. 2B). These experiments strongly suggest that addition of 2'-O-methyl modification patterns that enhance stability of the sense strand of miRNA mimics can be detrimental to overall activity, possibly due to conversion of the sense strand into a miR inhibitor.

Example 2

Identification of Mismatches that Prevent Sense Strand Inhibitory Activity

Results generated from Example 1 experiments demonstrated that the modified sense strand of miRNA mimics negatively affected the functionality of the molecule (by acting like an inhibitor). One or more mismatches were introduced into the duplex to determine whether mismatches could eliminate the negative effects of modified miRNA sense strands.

miRNA inhibitors often have 2'-O-methyl modifications at all nucleotides across the strand. The sense strand of a mimic with the G4 modification pattern contains 2'-O-methyl modifications at some or all Cs and Us. Given the similarity between the sense strand of a mimic and an miRNA inhibitor molecule, the inventors reasoned that inhibitors could be used to identify mimics mismatch positions that would eliminate the negative affects associated with modified sense strands.

Figure 3A:
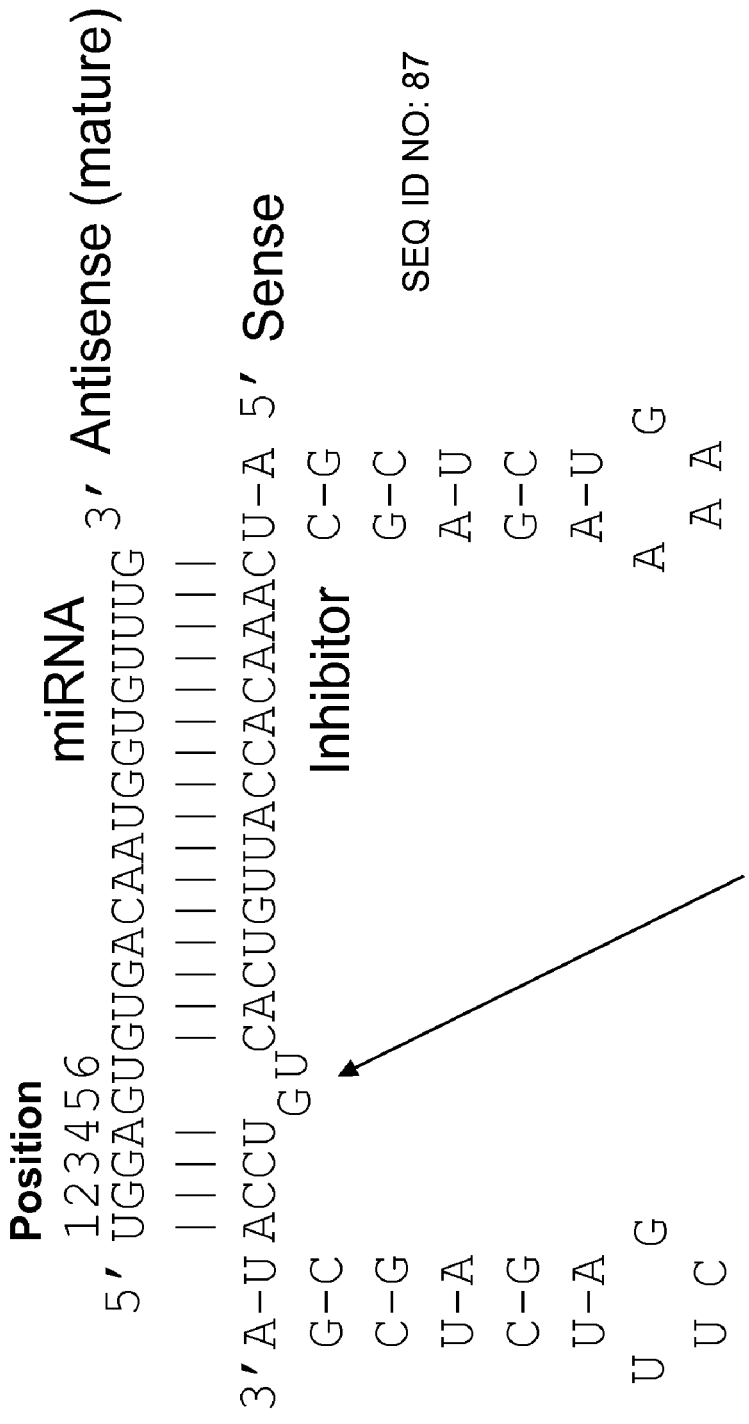
FIG. 3A shows a schematic representation of inhibitor molecules used to identify sense strand mismatch positions that affected overall activity. The top strand (referred to as the antisense/mature strand of a miRNA mimic) represents the mature miRNA strand of miR-21 to which an inhibitor is paired. The bottom strand (labeled inhibitor or sense) contains (1) paired 2 nucleotide mismatches (side-by-side) at various positions across the molecule, and (2) hairpin structures at both termini to enhance functionality.

Experimental design for these studies included synthesis of a collection of inhibitors to the miR-21 miRNA. These inhibitors contain a central 22 nucleotide region that is complementary to the mature (antisense) strand of the miRNA, flanked by hairpin regions on both the 5' and 3' side. The molecules are 54 nt in length, fully 2'-O-methylated (as indicated by the "m" preceeding each nucleotide in Table 2 below), and single stranded (see FIG. 3A). To study the importance of mismatches, each member of the collection contained a different two nucleotide mismatch (e.g., at antisense positions 1 and 2, 3 and 4, 5 and 6, see FIG. 3A (which shows a mismatch and positions 5 and 6) and Table 2 below) within the 22 nucleotide central region. In addition, as previous studies have shown that addition of hairpin structures to the termini of inhibitors can greatly enhance the potency of the molecules (see Vermeulen et al, RNA 13(5):723-730 (2007), incorporated herein by reference in its entirety), each sequence was modified with a hairpin to better assess positions that were critical for potency. (Note: in this experiment, the mature strand of the endogenous miRNA can also be referred to as the antisense strand and the inhibitor is synonymous with the sense strand).

TABLE 2

| Oligo Number | Sequence (5'-3') | SEQ ID NO: |
|---|---|---|
| Inmir21_mm12_hpRChp | mA.mG.mC.mU.mC.mU.mG.mA.mA.mA.mA.m G.mA.mG.mC.mU.mU.mC.mA.mA.mC.mA.mU. mC.mA.mG.mU.mC.mU.mG.mA.mU.mA.mA.m G.mC.mA.mU.mU.mC.mG.mA.mG.mA.mU.mU. mC.mG.mU.mC.mU.mC.mG.mA | 5 |
| Inmir21_mm34_hpRChp | mA.mG.mC.mU.mC.mU.mG.mA.mA.mA.mA.m G.mA.mG.mC.mU.mU.mC.mA.mA.mC.mA.mU. mC.mA.mG.mU.mC.mU.mG.mA.mU.mA.mA.m C.mG.mU.mA.mU.mC.mG.mA.mG.mA.mU.mU. mC.mG.mU.mC.mU.mC.mG.mA | 6 |
| Inmir21_mm56_hpRChp | mA.mG.mC.mU.mC.mU.mG.mA.mA.mA.mA.m G.mA.mG.mC.mU.mU.mC.mA.mA.mC.mA.mU. mC.mA.mG.mU.mC.mU.mG.mA.mU.mU.mU.m G.mC.mU.mA.mU.mC.mG.mA.mG.mA.mU.mU. mC.mG.mU.mC.mU.mC.mG.mA | 7 |
| Inmir21_mm78_hpRChp | mA.mG.mC.mU.mC.mU.mG.mA.mA.mA.mA.m G.mA.mG.mC.mU.mU.mC.mA.mA.mC.mA.mU. mC.mA.mG.mU.mC.mU.mG.mU.mA.mA.mA.m G.mC.mU.mA.mU.mC.mG.mA.mG.mA.mU.mU. mC.mG.mU.mC.mU.mC.mG.mA | 8 |
| Inmir21_mm910_hpRChp | mA.mG.mC.mU.mC.mU.mG.mA.mA.mA.mA.m G.mA.mG.mC.mU.mU.mC.mA.mA.mC.mA.mU. mC.mA.mG.mU.mC.mA.mC.mA.mU.mA.mA.m G.mC.mU.mA.mU.mC.mG.mA.mG.mA.mU.mU. mC.mG.mU.mC.mU.mC.mG.mA | 9 |
| Inmir21_mm1112_hpRChp | mA.mG.mC.mU.mC.mU.mG.mA.mA.mA.mA.m G.mA.mG.mC.mU.mU.mC.mA.mA.mC.mA.mU. mC.mA.mG.mA.mG.mU.mG.mA.mU.mA.mA.m G.mC.mU.mA.mU.mC.mG.mA.mG.mA.mU.mU. mC.mG.mU.mC.mU.mC.mG.mA | 10 |
| Inmir21_mm1314_hpRChp | mA.mG.mC.mU.mC.mU.mG.mA.mA.mA.mA.m G.mA.mG.mC.mU.mU.mC.mA.mA.mC.mA.mU. mC.mU.mC.mU.mC.mU.mG.mA.mU.mA.mA.m G.mC.mU.mA.mU.mC.mG.mA.mG.mA.mU.mU. mC.mG.mU.mC.mU.mC.mG.mA | 11 |
| Inmir21_mm1516_hpRChp | mA.mG.mC.mU.mC.mU.mG.mA.mA.mA.mA.m G.mA.mG.mC.mU.mU.mC.mA.mA.mA.mC.mA.mA. mG.mA.mG.mU.mC.mU.mG.mA.mU.mA.mA.m G.mC.mU.mA.mU.mC.mG.mA.mG.mA.mU.mU. mC.mG.mU.mC.mU.mC.mG.mA | 12 |
| Inmir21_mm1718_hpRChp | mA.mG.mC.mU.mC.mU.mG.mA.mA.mA.mA.m G.mA.mG.mC.mU.mU.mC.mA.mA.mG.mU.mU. mC.mA.mG.mU.mC.mU.mG.mA.mU.mA.mA.m G.mC.mU.mA.mU.mC.mG.mA.mG.mA.mU.mU. mC.mG.mU.mC.mU.mC.mG.mA | 13 |
| Inmir21_mm1920_hpRChp | mA.mG.mC.mU.mC.mU.mG.mA.mA.mA.mA.m G.mA.mG.mC.mU.mU.mC.mU.mU.mC.mA.mU. mC.mA.mG.mU.mC.mU.mG.mA.mU.mA.mA.m G.mC.mU.mA.mU.mC.mG.mA.mG.mA.mU.mU. mC.mG.mU.mC.mU.mC.mG.mA | 14 |
| Inmir21_mm2122_hpRChp | mA.mG.mC.mU.mC.mU.mG.mA.mA.mA.mA.m G.mA.mG.mC.mU.mA.mG.mA.mA.mC.mA.mU. mC.mA.mG.mU.mC.mU.mG.mA.mU.mA.mA.m G.mC.mU.mA.mU.mC.mG.mA.mG.mA.mU.mU. mC.mG.mU.mC.mU.mC.mG.mA | 15 |

The collection of mismatched inhibitors were transfected into HeLa cells (10,000 cells per well, DharmFECTduo) along with a dual luciferase reporter construct containing a 3' UTR target sequence that is complementary to the mature miR-21 sequence inserted in the 3' UTR multiple cloning site of the hRluc gene. HeLa cells express miR-21, therefore in the absence of inhibitor activity one would expect the ratio of *Renilla* luciferase to firefly luciferase to be low. Addition of an active inhibitor should diminish the effects of the endogenous miR-21, and thus increase the ratio of *Renilla* to firefly luciferase. In contrast, addition of a mismatch inhibitor that is less functional due to incorporation of a mismatch at a critical position should weaken the effects of the inhibitor and therefore decrease in the ratio of *Renilla* to firefly luciferase. Concentrations of the mismatched inhibitors during the transfection varied between 0.03 and 21 nM. Luciferase readings were then assessed at 48 hours post-transfection and compared with those of a match control (i.e. an inhibitor having 100% identity to miR-21) to identify positions where sense strand mismatches affected the ability of inhibitors to act.

Figure 3B:
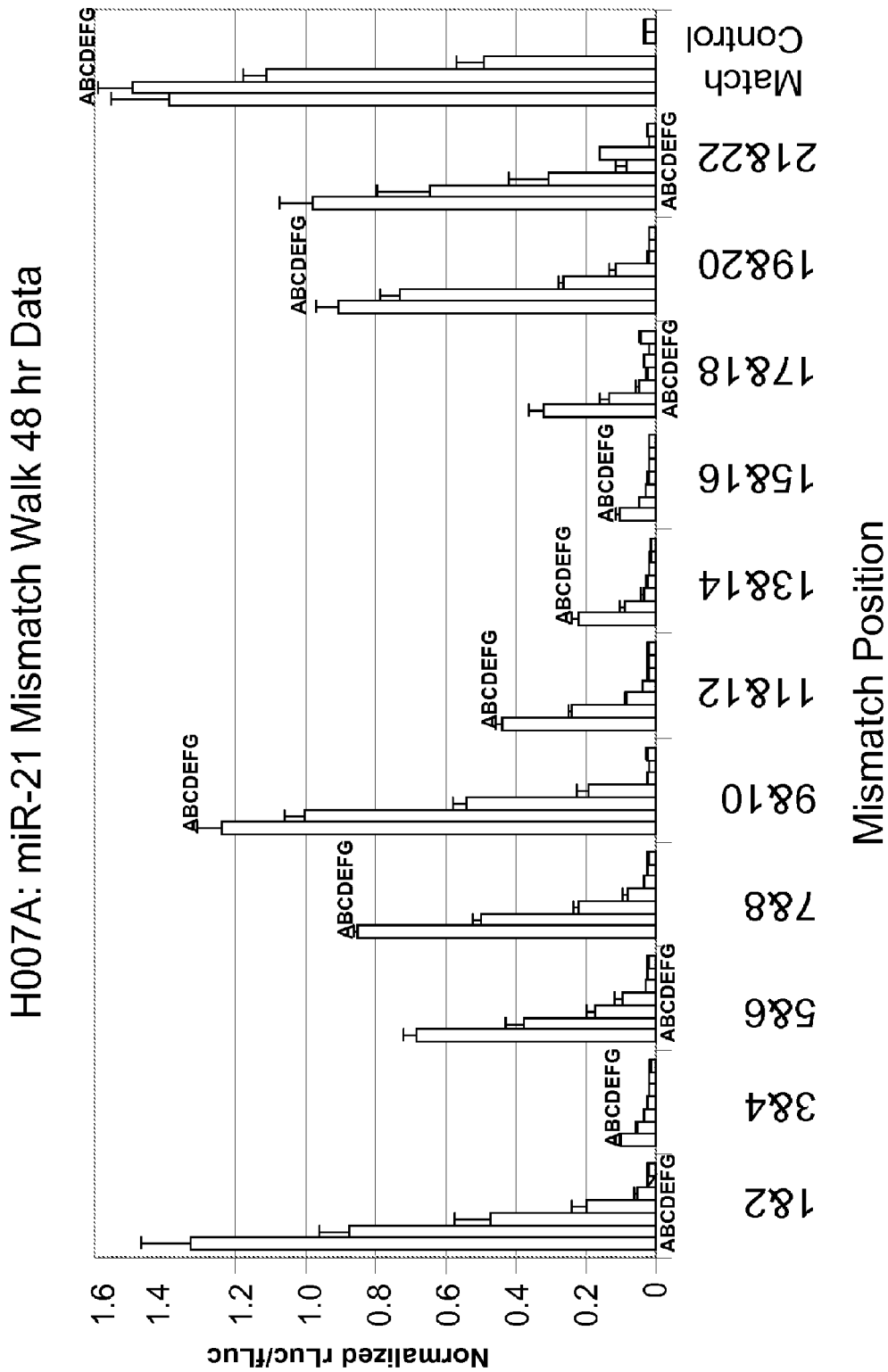
FIG. 3B is a graphical representation of the effects of introducing 2 nucleotide mismatches at different positions in the inhibitor on the ratio of *Renilla* luciferase to firefly luciferase in HeLa cells. The numbers on the X-axis represent the positions along the antisense strand (counting from the 5' end of the molecule). Thus positions 2-8 represent the seed region of the antisense molecule. Experiments were run at a range of concentrations (0.03-21 nM). "Match Control" represents an inhibitor molecule without mismatches.

The results of these experiments identified multiple positions where addition of sense strand mismatches greatly affected the ability of the molecules to silence endogenous miRNAs (FIG. 3B). In FIG. 3B, the inhibitor concentrations are indicated by the letters A-G under each column of the bar graph: A=21 nM; B=7 nM, C=2 nM, D=0.8 nM, E=0.3 nM, F=0.08 nM, G=0.03 nM. As incorporation of mismatches in the inhibitor greatly affected the functionality of these molecules, the inventors reasoned that it is likely that mismatches in the equivalent positions of sense strands of miRNA mimics would prevent the mimics from having any inhibitory activity. As incorporation of side-by-side mismatches could greatly affect the annealing of short, partially modified oligonucleotides, the effects of single mismatches at positions distributed across the molecule (e.g. position 1, 7, and 14 of the antisense) were tested.

Example 3

Enhancing Functionality of miRNA Mimics by Incorporating Mismatches in the Sense Strand Studies were performed to test whether mismatches identified in the inhibitor studies (Example 2) could significantly enhance the functionality of miRNA mimics. To achieve this, mimics were synthesized in a variety of forms including 1) miRIDIAN (2'-O-methyl modifications on positions 1 and 2 of the sense strand (counting from the 5' terminus of the molecule), a two nucleotide UU overhang on the 3' end of the sense strand, a 5' phosphate group on the antisense strand, a two nucleotide overhang on the 3' end of the antisense strand that is complementary to the nucleotides found in natural pre-miRNA), 2) siSTABLE (2'-O-methyl modification on positions 1 and 2 of the sense strand (counting from the 5' terminus of the molecule), 2'-O-methyl modification of all Cs and Us of the sense strand, 2' F modification of all Cs and Us of the antisense strand, 5' phosphorylation of the antisense strand, and a two nucleotide overhang on the 3' end of the antisense strand having phosphorothioate internucleotide modifications, 3) G4 modification pattern: (2'-O-methyl modification on positions 1 and 2 of the sense strand (counting from the 5' terminus of the molecule), 2'-O-methyl modification of all Cs and Us on the sense strand, 2' F modification of all Cs and Us of the antisense strand, a two nucleotide overhang containing phosphorothioate internucleotide linkages on the 3' end of the antisense strand, 5' phosphorylation of the antisense strand, and a cholesterol conjugate attached via a C5 linker on the 3' terminus of the sense strand). G4 modified miRNAs were also synthesized with a mismatch at position 6 of the sense strand, with a mismatch at position 6 and 19 of the sense strand, and with a mismatch at positions 6, 13, and 19 of the sense strand (positions 6, 13, and 19 of the sense strand are opposite positions 14, 7, and 1, respectively, of the antisense strand). Sequences employed in these experiments are reported in Table 3. The G4 modified miRNAs in this example also contained a cholesterol molecule linked the 3' end of the sense strand via a C5 linker.

To study the effects of each design on functionality, the mimic was introduced into cells along with an appropriate dual luciferase reporter construct containing a target sequence (that is fully complementary to the mature strand of the modified miRNA) inserted in the 3' UTR of the *Renilla* gene of a dual luciferase reporter.

The method of introducing mimic and reporter into target cells depended on the modification pattern applied to the mimic. In cases where molecules did not have a cholesterol modification (e.g., miRIDIAN and siSTABLE) molecules were co-transfected into cells using a lipid delivery reagent (DharmaFECT Duo, 1 nM mimic, 100 ng/well of reporter). Where cholesterol conjugates were included in the design (i.e., in the G4 modified molecules) the mimic was introduced first (passive delivery, 25 nM, 24 hours) followed by lipid mediated delivery of the reporter construct using DharmaFECT duo. To get a thorough understanding of the performance of these designs, molecules of each class were synthesized to mimic miRNAs with very low or no (miR-122a, miR133a, miR141, miR-205, miE-206, miR-375), low (miR-1, miR-107, miR181c, miR-196a1, and miR-210), and moderate (miR18a, miR-92-1, miR-98, miR-130a, and miR320) expression.

TABLE 3

Sequences used in experiments presented in Example 4.
Modification patterns associated with each strand
(AS = antisense; S = sense) are described in text.
Lowercase letters represent positions of mismatches.

| miRNA | S/AS | Sequence (5'-3') | Seq Id No: |
|---|---|---|---|
| miR-1 | AS | UGGAAUGUAAAGAAGUAUG*U*U | 16 |
| miR-1_mimG4 | SS | CAUACUUCUUUACAUUCCA | 17 |
| miR-1_mimG4_MM6 | SS | CAUACaUCUUUACAUUCCA | 18 |
| miR-1_mimG4_MMB(_6_19) | SS | CAUACaUCUUUACAUUCCu | 19 |
| miR-1_mimG4_MMC(_6_13_19) | SS | CAUACaUCUUUAgAUUCCu | 20 |
| miR-18a | AS | UAAGGUGCAUCUAGUGCAG*U*U | 21 |
| miR-18a_mimG4 | SS | CUGCACUAGAUGCACCUUA | 22 |
| miR-18a_mimG4_MM6 | SS | CUGCAgUAGAUGCACCUUA | 23 |
| miR-18a_mimG4_MMB(_6_19) | SS | CUGCAgUAGAUGCACCUUu | 24 |
| miR-18a_mimG4_MMC(_6_13_19) | SS | CUGCAgUAGAUGgACCUUu | 25 |

TABLE 3 -continued

Sequences used in experiments presented in Example 4.
Modification patterns associated with each strand
(AS = antisense; S = sense) are described in text.
Lowercase letters represent positions of mismatches.

| miRNA | S/AS | Sequence (5'-3') | Seq Id No: |
|---|---|---|---|
| miR-92-1 | AS | UAUUGCACUUGUCCCGGCC*U*U | 26 |
| miR-92-1_mimG4 | SS | GGCCGGGACAAGUGCAAUA | 27 |
| miR-92-1_mimG4_MM6 | SS | GGCCGcGACAAGUGCAAUA | 28 |
| miR-92-1_mimG4_MMB(_6_19) | SS | GGCCGcGACAAGUGCAAUu | 29 |
| miR-92-1_mimG4_MMC(_6_13_19) | SS | GGCCGcGACAAGaGCAAUu | 30 |
| miR-98 | AS | UGAGGUAGUAAGUUGUAUU*U*U | 31 |
| miR-98_mimG4 | SS | AAUACAACUUACUACCUCA | 32 |
| miR-98_mimG4_MM6 | SS | AAUACuACUUACUACCUCA | 33 |
| miR-98_mimG4_MMB(_6_19) | SS | AAUACuACUUACUACCUCu | 34 |
| miR-98_mimG4_MMC(_6_13_19) | SS | AAUACuACUUACaACCUCu | 35 |
| miR-107 | AS | AGCAGCAUUGUACAGGGCU*U*U | 36 |
| miR-107_mimG4 | SS | AGCCCUGUACAAUGCUGCU | 37 |
| miR-107_mimG4_MM6 | SS | AGCCCaGUACAAUGCUGCU | 38 |
| miR-107_mimG4_MMB(_6_19) | SS | AGCCCaGUACAAUGCUGCa | 39 |
| miR-107_mimG4_MMC(_6_13_19) | SS | AGCCCaGUACAAaGCUGCa | 40 |
| miR-130a | AS | CAGUGCAAUGUUAAAAGGG*U*U | 41 |
| miR-130a_mimG4 | SS | CCCUUUUAACAUUGCACUG | 42 |
| miR-130a_mimG4_MM6 | SS | CCCUUaUAACAUUGCACUG | 43 |
| miR-130a_mimG4_MMB(_6_19) | SS | CCCUUaUAACAUUGCACUc | 44 |
| miR-130a_mimG4_MMC(_6_13_19) | SS | CCCUUaUAACAUaGCACUc | 45 |
| miR-133a | AS | UUGGUCCCCUUCAACCAGC*U*U | 46 |
| miR-133a_mimG4 | SS | GCUGGUUGAAGGGGACCAA | 47 |
| miR-133a_mimG4_MM6 | SS | GCUGGaUGAAGGGGACCAA | 48 |
| miR-133a_mimG4_MMB(_6_19) | SS | GCUGGaUGAAGGGGACCAu | 49 |
| miR-133a_mimG4_MMC(_6_13_19) | SS | GCUGGaUGAAGGCGACCAu | 50 |
| miR-181c | AS | AACAUUCAACCUGUCGGUG*U*U | 51 |
| miR-181c_mimG4 | SS | CACCGACAGGUUGAAUGUU | 52 |
| miR-181c_mimG4_MM6 | SS | CACCGuCAGGUUGAAUGUU | 53 |
| miR-181c_mimG4_MMB(_6_19) | SS | CACCGuCAGGUUGAAUGUa | 54 |
| miR-181C(_6_13_19)_mimG4_MMC(_6_13_19) | SS | CACCGuCAGGUUcAAUGUa | 55 |
| miR-196a1 | AS | UAGGUAGUUUCAUGUUGUU*U*U | 56 |
| miR-196a1_mimG4 | SS | AACAACAUGAAACUACCUA | 57 |
| miR-196a1_mimG4_MM6 | SS | AACAAgAUGAAACUACCUA | 58 |
| miR-196a1_mimG4_MMB(_6_19) | SS | AACAAgAUGAAACUACCUu | 59 |
| miR-196a1_mimG4_MMC(_6_13_19) | SS | AACAAgAUGAAAgUACCUu | 60 |
| miR-205 | AS | UCCUUCAUUCCACCGGAGU*U*U | 61 |

TABLE 3 -continued

Sequences used in experiments presented in Example 4.
Modification patterns associated with each strand
(AS = antisense; S = sense) are described in text.
Lowercase letters represent positions of mismatches.

| miRNA | S/AS | Sequence (5'-3') | Seq Id No: |
|---|---|---|---|
| miR-205_mimG4 | SS | ACUCCGGUGGAAUGAAGGA | 62 |
| miR-205_mimG4_MM6 | SS | ACUCCcGUGGAAUGAAGGA | 63 |
| miR-205_mimG4_MMB(_6_19) | SS | ACUCCcGUGGAAUGAAGGu | 64 |
| miR-205_mimG4_MMC(_6_13_19) | SS | ACUCCcGUGGAAaGAAGGu | 65 |
| miR-206 | AS | UGGAAUGUAAGGAAGUGUG*U*U | 66 |
| miR-206_mimG4 | SS | CACACUUCCUUACAUUCCA | 67 |
| miR-206_mimG4_MM6 | SS | CACACaUCCUUACAUUCCA | 68 |
| miR-206_mimG4_MMB(_6_19) | SS | CACACaUCCUUACAUUCCu | 69 |
| miR-206_mimG4_MMC(_6_13_19) | SS | CACACaUCCUUAgAUUCCu | 70 |
| miR-210 | AS | CUGUGCGUGUGACAGCGGC*U*U | 71 |
| miR-210_mimG4 | SS | GCCGCUGUCACACGCACAG | 72 |
| miR-210_mimG4_MM6 | SS | GCCGCaGUCACACGCACAG | 73 |
| miR-210_mimG4_MMB(_6_19) | SS | GCCGCaGUCACACGCACAc | 74 |
| miR-210_mimG4_MMC(_6_13_19) | SS | GCCGCaGUCACAgGCACAc | 75 |
| miR-320 | AS | AAAAGCUGGGUUGAGAGGG*U*U | 76 |
| miR-320_mimG4 | SS | CCCUCUCAACCCAGCUUUU | 77 |
| miR-320_mimG4_MM6 | SS | CCCUCaCAACCCAGCUUUU | 78 |
| miR-320_mimG4_MMB(_6_19) | SS | CCCUCaCAACCCAGCUUUa | 79 |
| miR-320_mimG4_MMC(_6_13_19) | SS | CCCUCaCAACCCuGCUUUa | 80 |
| miR-375 | AS | UUUGUUCGUUCGGCUCGCG*U*U | 81 |
| miR-375_mimG4 | SS | CGCGAGCCGAACGAACAAA | 82 |
| miR-375_mimG4_MM6 | SS | CGCGAcCCGAACGAACAAA | 83 |
| miR-375_mimG4_MMB(_6_19) | SS | CGCGAcCCGAACGAACAAu | 84 |
| miR-375_mimG4_MMC(_6_13_19) | SS | CGCGAcCCGAACcAACAAu | 85 |

Figure 4A:
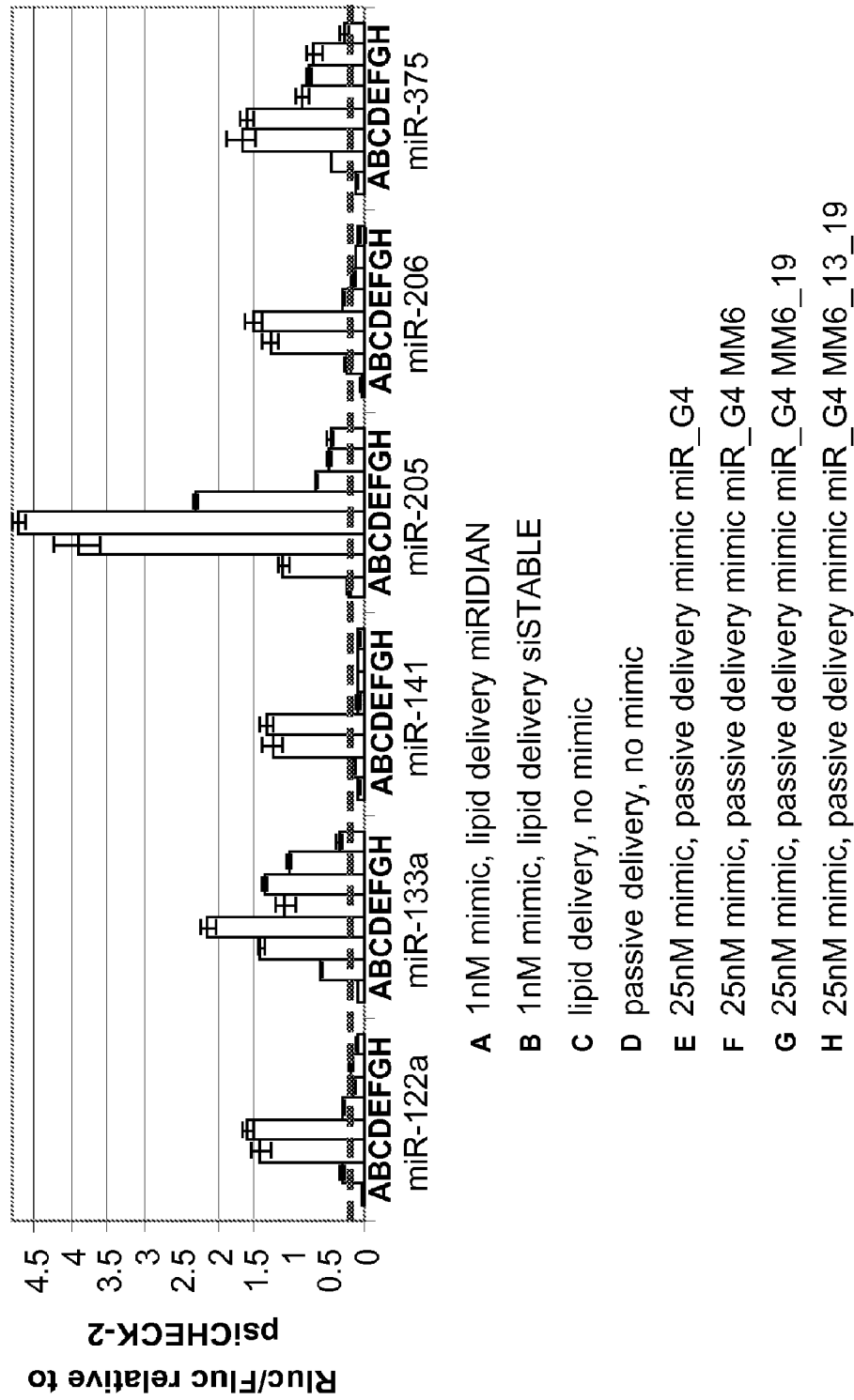
FIG. 4A provides a graphical representation demonstrating the performance of miRNA mimics (miR-122a, miR-133a, miR-141, miR-205, miR-206, and miR-375) containing different modification patterns (miRIDIAN, siSTABLE, G4, and G4 plus mismatches at position 6, 6 and 19, or 6, 13, and 19 of the sense strand). All of the mimics tested in FIG. 4A are either not expressed or expressed at very low levels in the HeLa test cell line.
Figure 4B:
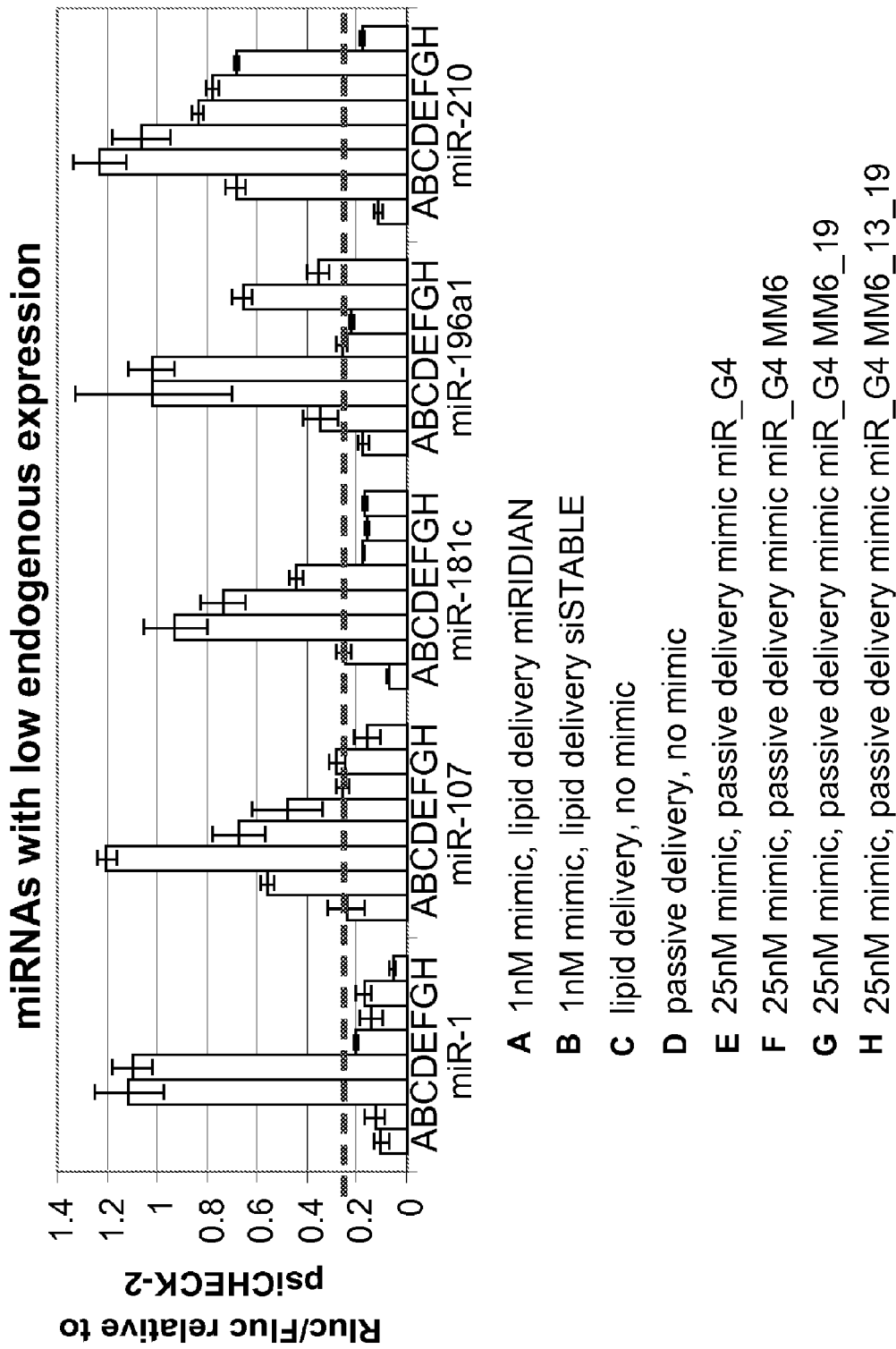
FIG. 4B provides a graphical representation demonstrating the performance of miR-1, miR-107, miR-141, miR-181c, miR-196a1, and miR-210 mimics containing the miRIDIAN, siSTABLE, G4, and G4 plus mismatches at position 6, 6 and 19, or 6, 13, and 19 modification patterns. All of the mimics tested in FIG. 4B are expressed at low levels in the HeLa test cell line.
Figure 4C:
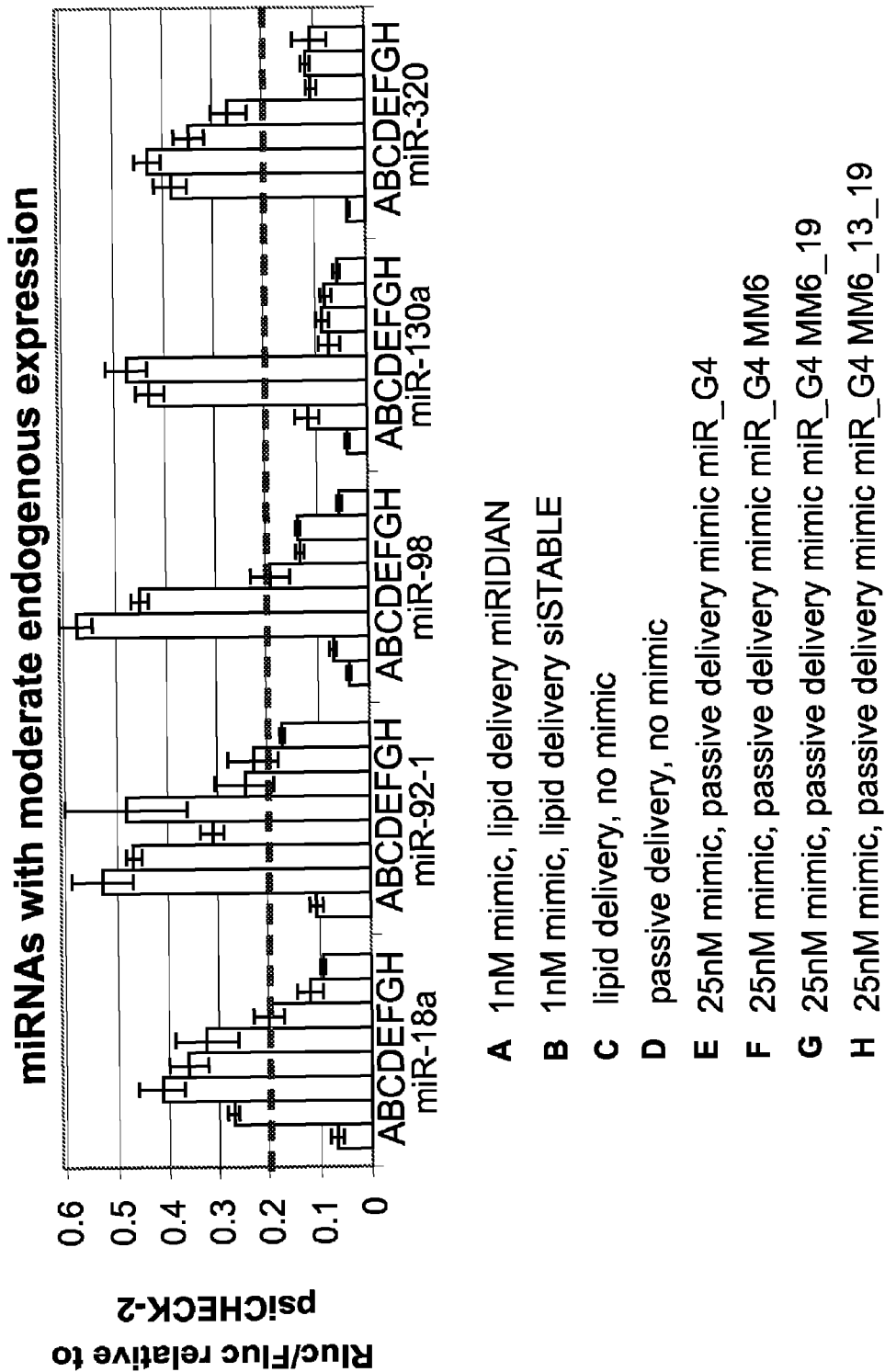
FIG. 4C provides a graphical representation demonstrating the performance of miR-18a, miR-92-1, miR-98, miR-130a, and miR-320 mimics containing the miRIDIAN, siSTABLE, G4, and G4 plus mismatches at position 6, 6 and 19, or 6, 13, and 19 modification patterns. All of the mimics tested in FIG. 4C are moderately expressed in the HeLa test cell line.

Results of these experiments are provided in FIGS. 4A-4C. In each of FIGS. 4A-4C, the individual columns of the bar graph are labeled with the letters A-H to indicate the identity of the mimic and the transfection conditions. Specifically:

A=1 nM mimic, lipid delivery miRIDIAN;
B=1 nM mimic, lipid delivery siSTABLE;
C=lipid delivery, no mimic;
D=passive delivery, no mimic;
E=25 nM mimic, passive delivery mimic miR_G4;
F=25 nM mimic, passive delivery mimic miR_G4 MM6;
G=25 nM mimic, passive delivery mimic miR_G4 MM6_19; and
H=25 nM mimic, passive delivery mimic miR_G4 MM6_13_19

For miRNAs with very low or no endogenous expression, mimics having mismatches performed as well or better than mimics without mismatches delivered by lipid-mediated delivery or passive cholesterol-mediated delivery. For miR-205, addition of a mismatch at positions 6, positions 6 and 19, or positions 6, 13, and 19 greatly enhanced the ability of the molecule to target the reporter construct. In the cases of miR-133a and miRNA-375, while addition of one (position 6) or two (positions 6 and 19) mismatches did not significantly enhance performance, molecules with mismatches at all three positions (6, 13, and 19) greatly enhanced the ability of the molecule to target the reporter gene.

Similar patterns were observed with miRNAs of low and moderate expression (FIGS. 4B and 4C). In the case of miR-181c and miR-320, addition of a single base pair mismatch at position 6 greatly enhanced the performance of G4 modified molecules. In other cases, including miR-18a, miR-92-1, miR-98, miR-107, and miR-210, incorporation of additional mismatches at positions 19 and 13 led to progressively increases in the levels of performance. In most cases, addition of one or more mismatches enabled passively delivered molecules to perform as well or nearly as well as mimics that were delivered by lipid mediated transfection.

What is claimed:

1. A duplex oligonucleotide complex comprising:
   (a) a sense strand that is nineteen nucleotides in length, wherein nucleotides 1 and 2 and all C and all U nucleotides on said sense strand are 2'O-methyl modified;
   (b) an antisense strand that is twenty-one nucleotides in length, wherein
      (i) all C nucleotides and all U nucleotides on said antisense strand are 2' F modified; and
      (ii) the sense strand and the antisense strand form a duplex having a two nucleotide overhang at the 3' end of the antisense strand, said two nucleotide overhang comprising phosphorothioate linkages;
   (c) a cholesterol molecule attached to the 3' end of the sense strand via a C5 linker molecule thereby forming a cholesterol-linker-sense strand structure of:

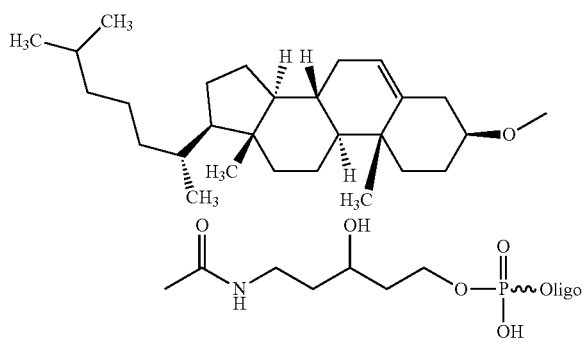

(d) a phosphate group at the 5' end of the antisense strand; and
   (e) three mismatches on the sense strand with the corresponding nucleotides on the antisense strand, wherein the mismatches are between nucleotide 6 on the sense strand and opposite nucleotide 14 on the antisense strand, nucleotide 13 on the sense strand and opposite nucleotide 7 on the antisense strand, and nucleotide 19 on the sense strand and opposite nucleotide 1 on the antisense strand,
   wherein each nucleotide number refers to the nucleotide's position in an identified strand as counted from the identified strand's 5' end, and at all positions other than positions 6, 13 and 19 on the sense strand, there is a nucleotide that is complementary to the nucleotide on the opposite strand.

2. The duplex oligonucleotide complex of claim 1, wherein at least one of the mismatches is a G across from an A.

3. The duplex oligonucleotide complex of claim 1, wherein at least one of the mismatches is an A across from a C.

4. The duplex oligonucleotide complex of claim 1, wherein at least one of the mismatches is an A across from an A.

5. The duplex oligonucleotide of claim 1, wherein at least one of the mismatches is a G across from a G.

6. The duplex oligonucleotide of claim 1, wherein at least one of the mismatches is a C across from a C.

7. The duplex oligonucleotide of claim 1, wherein at least one of the mismatches is a U across from a U.

8. The duplex oligonucleotide complex of claim 1, wherein the antisense strand is 100% complementary to a target.

9. The duplex oligonucleotide complex of claim 1, wherein the overhang is UU.

10. A pharmaceutical composition comprising the duplex oligonucleotide complex of claim 1 and at least one pharmaceutically acceptable carrier or diluent.

* * * * *